(12) United States Patent
Wang et al.

(10) Patent No.: US 11,306,362 B2
(45) Date of Patent: Apr. 19, 2022

(54) GENE SIGNATURE PREDICTIVE OF HEPATOCELLULAR CARCINOMA RESPONSE TO TRANSCATHETER ARTERIAL CHEMOEMBOLIZATION (TACE)

(71) Applicant: The U.S.A., as represented by the Secretary, Department of Health and Human Services, Bethesda, MD (US)

(72) Inventors: Xin Wei Wang, Rockville, MD (US); Valerie Fako Miller, Washington, DC (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 730 days.

(21) Appl. No.: 16/076,239

(22) PCT Filed: Feb. 7, 2017

(86) PCT No.: PCT/US2017/016851
§ 371 (c)(1),
(2) Date: Aug. 7, 2018

(87) PCT Pub. No.: WO2017/139276
PCT Pub. Date: Aug. 17, 2017

(65) Prior Publication Data
US 2020/0032345 A1    Jan. 30, 2020

Related U.S. Application Data

(60) Provisional application No. 62/292,789, filed on Feb. 8, 2016.

(51) Int. Cl.
C12Q 1/68    (2018.01)
C12Q 1/6886  (2018.01)

(52) U.S. Cl.
CPC ..... *C12Q 1/6886* (2013.01); *C12Q 2600/106* (2013.01); *C12Q 2600/112* (2013.01); *C12Q 2600/158* (2013.01)

(58) Field of Classification Search
None
See application file for complete search history.

(56) References Cited

FOREIGN PATENT DOCUMENTS

CN    103852585    9/2015

OTHER PUBLICATIONS

Roessler et al; Cancer Research, vol. 70, pp. 10202-10212; 2010.*
Cheung et al (Nature Genetics, vol. 33, pp. 422-425; (2003).*
Lee (Clinical Chemistry, 47:8, 1350-1352 (2001).*
Michiels et al. Lancet, 2005; 365:488-492.*
Slonin, Nature Genetics Supplement, vol. 32, Dec. 2002, pp. 502-508.*
"23rd Annual Conference of APASL Mar. 12-15, 2014, Brisbane, Australia," *Hepatol. Int.*, vol. 8:S1-S405, 2014.
Budhu et al., "Prediction of Venous Metastases, Recurrence, and Prognosis in Hepatocellular Carcinoma Based on a Unique Immune Response Signature of the Liver Microenvironment," *Cancer Cell*, vol. 10:99-111, 2006.
Jian et al., "Involvement of Discoidin Domain 1 Receptor in Recurrence of Hepatocellular Carcinoma by Genome-Wide Analysis," *Med. Onocol.*, vol. 29:3077-3082, 2012.
Miller et al., "Identification of a gene signature predictive of HCC patient response to adjuvant transcatheter arterial chemoembolization (TACE)," Keystone Symposia on Molecular and Cellular Biology, Genomics and Personalized Medicine (Q2), Banff, Alberta, Canada, Feb. 7-11, 2016, Abstract, published Jan. 7, 2016.
Villanueva, et al., "Combining Clinical, Pathology, and Gene Expression Data to Predict Recurrence of Hepatocellular Carcinoma," *Gastroenterology*, vol. 140:1501-1512, 2011.
El-Halawany et al., "Investigating the Pretreatment miRNA Expression Patterns of Advanced Hepatocellular Carcinoma Patients in Associated with Response to TACE Treatment," *Biomed Res Int* 2015:649450, 12 pages, 2015.

* cited by examiner

*Primary Examiner* — Jehanne S Sitton
(74) *Attorney, Agent, or Firm* — Klarquist Sparkman, LLP

(57) ABSTRACT

This disclosure provides methods for predicting the likelihood that a hepatocellular carcinoma (HCC) will respond to transcatheter arterial chemoembolization (TACE) using a gene signature of 14 or 15 genes. Also provided are nucleic acid probes and kits for detecting the gene signature.

19 Claims, 13 Drawing Sheets

Specification includes a Sequence Listing.

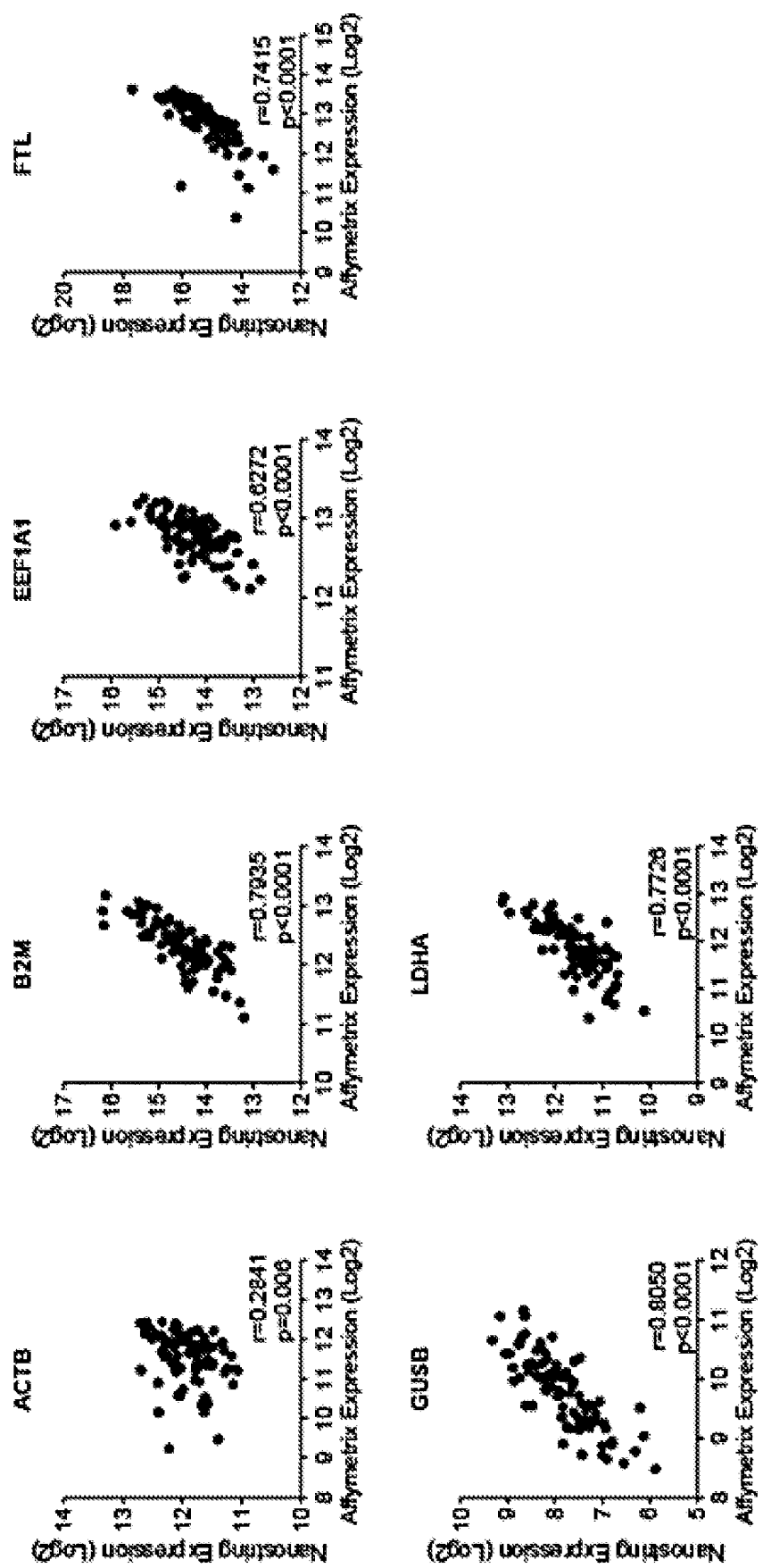

GENE SIGNATURE PREDICTIVE OF HEPATOCELLULAR CARCINOMA RESPONSE TO TRANSCATHETER ARTERIAL CHEMOEMBOLIZATION (TACE)

CROSS REFERENCE TO RELATED APPLICATIONS

This application is the U.S. National Stage of International Application No. PCT/US2017/016851, filed Feb. 7, 2017, published in English under PCT Article 21(2), which claims the benefit of U.S. Provisional Application No. 62/292,789, filed Feb. 8, 2016, which is herein incorporated by reference in its entirety.

FIELD

This disclosure relates to methods for predicting response of hepatocellular carcinoma to transcatheter arterial chemoembolization using a gene signature of 14 or 15 genes, as well as probes and kits for detecting the gene signature.

BACKGROUND

Hepatocellular carcinoma (HCC) is one of the most common cancers worldwide, and outcome is poor, due to tumor heterogeneity and a lack of effective treatment options for patients with later stage disease. Transcatheter arterial chemoembolization (TACE) is considered to be the gold standard of therapy for patients with intermediate to locally advanced tumors. Several randomized control trials have demonstrated a survival benefit following TACE, but only when strict selection criteria are employed. TACE is also commonly used as adjuvant therapy following surgical resection in Asia, yet randomized control trials evaluating the benefit of adjuvant TACE have shown conflicting results, likely due to patient selection and stratification.

SUMMARY

The disclosure provides methods of selecting patients who are most likely to respond to TACE. The methods are based on a 14-gene signature, which is predictive of response to TACE, independent of other clinical variables. This module is predictive of response regardless of whether patients received adjuvant TACE or TACE following tumor relapse. In addition, provided is a TACE Navigator Gene Signature Assay, which includes probes specific for each of the 14 TACE signature genes and 6 housekeeping control genes, which can be used with the prognostic assay.

Provided herein is a method of detecting expression of a plurality of genes that indicate whether a HCC will respond to TACE. In some embodiments, the method includes detecting or measuring expression of ASNS, CDK1, DNASE1L3, FBXL5, GOT2, GRHPR, IARS, LGALS3, LHFPL2, MFGE8, MKI67, PEBP1, TNFSF10, and UBB in an HCC sample obtained from a subject diagnosed with HCC, relative to a control. For example, nucleic acid probes specific for each of these genes can be incubated with the sample, and hybridization between the probe and the gene measured, for example measuring fluorescence from a fluorophore on the probe. A modulation (increase or decrease) in expression of ASNS, CDK1, DNASE1L3, FBXL5, GABARAPL3, GOT2, GRHPR, IARS, LGALS3, LHFPL2, MFGE8, MKI67, PEBP1, TNFSF10 and UBB relative to the control (such as ACTB, B2M, EEF1A1, FTL, GUSB, and LDHA) indicates the HCC will respond to TACE. In some embodiments, the method further includes detecting expression of GABARAPL3 in an HCC sample obtained from a subject diagnosed with HCC, relative to a control. A modulation (increase or decrease) in expression of GABARAPL3 relative to the control indicates the HCC will respond to TACE. In some embodiments, the method further includes performing TACE on the subject, for example if modulated ASNS, CDK1, DNASE1L3, FBXL5, GABARAPL3, GOT2, GRHPR, IARS, LGALS3, LHFPL2, MFGE8, MKI67, PEBP1, TNFSF10 and UBB (and in some examples also GABARAPL3) expression relative to the control is measured.

Further provided is a probe set that includes a nucleic acid probe specific for each of ASNS, CDK1, DNASE1L3, FBXL5, GOT2, GRHPR, IARS, LGALS3, LHFPL2, MFGE8, MKI67, PEBP1, TNFSF10, and UBB. In some embodiments, the probe set further includes a nucleic acid probe specific for GABARAPL3. In some embodiments, the probe set further includes a nucleic acid probe specific for each of ACTB, B2M, EEF1A1, FTL, GUSB, and LDHA. Also provided are kits comprising the probe sets disclosed herein.

Also provided is a method of detecting expression of a plurality of genes that indicate whether a HCC will respond to TACE. In some embodiments, the method includes detecting expression of ASNS, CDK1, DNASE1L3, FBXL5, GOT2, GRHPR, IARS, LGALS3, LHFPL2, MFGE8, MKI67, PEBP1, TNFSF10, and UBB in an HCC sample obtained from a subject diagnosed with HCC, relative to a control, using a probe set disclosed herein. In some embodiments, the method further includes detecting expression of GABARAPL3 in an HCC sample obtained from a subject diagnosed with HCC, relative to a control, using a probe set disclosed herein.

The foregoing and other objects and features of the disclosure will become more apparent from the following detailed description, which proceeds with reference to the accompanying figures.

BRIEF DESCRIPTION OF THE DRAWINGS

FIG. 1A shows differential overall survival in the TACE patient cohort when patients were assigned to clusters by hierarchical clustering of the 1,292 most variable genes. FIG. 1B shows there was no difference in overall survival when patients receiving other adjuvant therapy were assigned to clusters by hierarchical clustering (FIG. 1B). P values were calculated by log rank test.

FIGS. 7A-7B show correlation between gene expression (Log 2), as measured by AFFYMETRIX™ chip and NANOSTRING™, for TACE Navigator signature genes (FIG. 7A) and accompanying housekeeping genes (FIG. 7B). P and R values shown in each panel were calculated by Pearson Correlation, with a P value of less than 0.05 indicating statistical significance.

SEQUENCE LISTING

Figure 1B:
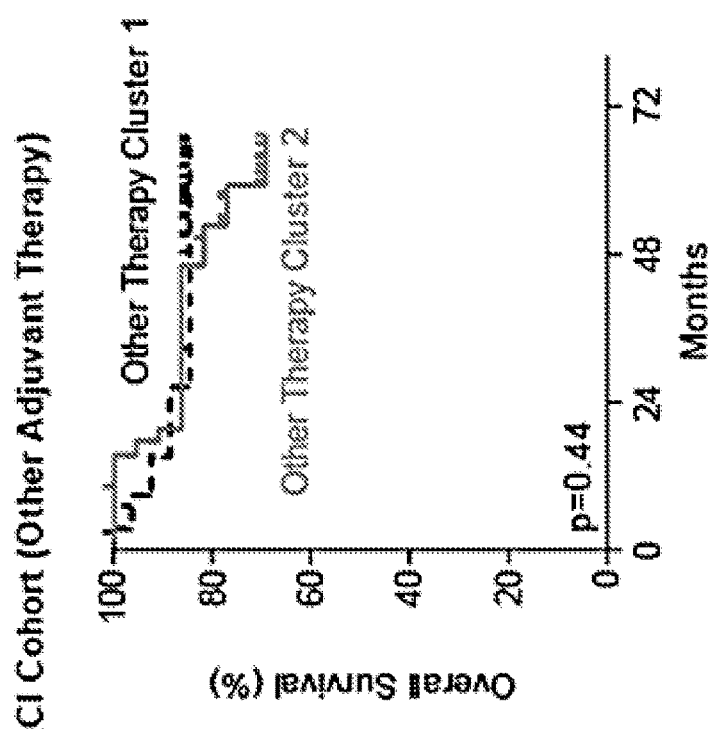
FIGS. 1A-1B are graphs showing hierarchical clustering of the TACE patient cohort.

The nucleic sequences listed in the accompanying sequence listing are shown using standard letter abbreviations for nucleotide bases, as defined in 37 C.F.R. 1.822. Only one strand of each nucleic acid sequence is shown, but the complementary strand is understood as included by any reference to the displayed strand. The Sequence Listing is submitted as an ASCII text file, created on Jul. 17, 2018, 5.09 KB, which is incorporated by reference herein. In the accompanying sequence listing:

SEQ ID NOs: 1-21 are target nucleic acid sequences of the nCounter® CodeSet.

DETAILED DESCRIPTION

I. Abbreviations

ACTB beta-actin
ASNS asparagine synthetase
B2M beta-2-microglobulin
CDK1 cyclin-dependent kinase 1
CGH comparative genomic hybridization
DNASE1L3 deoxyribonuclease I-like 3
EEF1A1 elongation factor 1-alpha 1
FBXL5 F-box and leucine-rich repeat protein 5
FTL ferritin light chain
GABARAPL3 GABA(A) receptors associated protein like 3, pseudogene
GOT2 glutamic-oxaloacetic transaminase 2, mitochondrial
GRHPR glyoxylate-reductase/hydroxypyruvate reductase
GUSB beta-glucuronidase
HBV hepatitis B virus
HCC hepatocellular carcinoma
HCV hepatitis C virus
HIF-1α hypoxia-inducible factor 1-alpha
IARS isoleucyl-tRNA synthetase
LDHA lactate dehydrogenase A
LGALS3 lectin, galactoside-binding, soluble 3
LHFPL2 lipoma HMGIC fusion partner-like 2 protein
MFGE8 milk fat globule-EGF factor 8 protein
MK167 antigen Ki-67
PEBP1 phosphatidylethanolamine binding protein 1
QC quality control
SAGE Serial Analysis of Gene Expression
TACE transcatheter arterial chemoembolization
$T_m$ melting temperature
TNFSF10 tumor necrosis factor superfamily, member 10
TNM tumor-node-metastasis
UBB ubiquitin B
VEGF vascular endothelial growth factor II. Terms and Methods Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics*, 2nd Edition, 2003 (ISBN: 0-471-26821-6).

The singular forms "a," "an," and "the" refer to one or more than one, unless the context clearly dictates otherwise. For example, the term "comprising a probe" includes single or plural probes and is considered equivalent to the phrase "comprising at least one probe." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank® Accession numbers (for the sequence present on Feb. 8, 2016). In case of conflict, the present specification, including explanations of terms, will control. In addition, the materials, methods, and examples are illustrative only and not intended to be limiting.

Except as otherwise noted, the methods and techniques of the present disclosure are generally performed according to conventional methods well known in the art and as described in various general and more specific references that are cited and discussed throughout the present specification. See, e.g., Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

In order to facilitate review of the various embodiments of the disclosure, the following explanations of specific terms are provided:

Adjunctive therapy: A treatment used in combination with a primary treatment to improve the effects of the primary treatment. For example, adjunctive therapy can include chemotherapy that is administered following surgical resection of cancerous tissue. In example, adjunctive therapy can include surgery following TACE.

Administration: To provide or give a subject an agent, such as a chemotherapeutic agent, by any effective route. Exemplary routes of administration include, but are not limited to, injection (such as subcutaneous, intramuscular, intradermal, intraperitoneal, intratumoral, transarterial, and intravenous), oral, sublingual, rectal, transdermal, intranasal, vaginal and inhalation routes.

Antibody: A polypeptide including at least a light chain or heavy chain immunoglobulin variable region which specifically recognizes and binds an epitope of an antigen, such as ASNS, CDK1, DNASE1L3, FBXL5, GABARAPL3, GOT2, GRHPR, IARS, LGALS3, LHFPL2, MFGE8, MKI67, PEBP1, TNFSF10, UBB, ACTB, B2M, EEF1A1, FTL, GUSB, LDHA, or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Antibodies of the present disclosure include those that are specific for ASNS, CDK1, DNASE1L3, FBXL5, GABARAPL3, GOT2, GRHPR, IARS, LGALS3, LHFPL2, MFGE8, MKI67, PEBP1, TNFSF10, UBB, ACTB, B2M, EEF1A1, FTL, GUSB, or LDHA.

The term antibody includes intact immunoglobulins, as well the variants and portions thereof, such as Fab' fragments, F(ab)'$_2$ fragments, single chain Fv proteins ("scFv"), and disulfide stabilized Fv proteins ("dsFv"). The term also includes genetically engineered forms such as chimeric antibodies (for example, humanized murine antibodies), and heteroconjugate antibodies (such as, bispecific antibodies). Also includes monoclonal antibodies and polyclonal antibodies.

Antigen Ki-67 (MKI67): e.g., OMIM 176741. Includes mammalian (such as human) MKI67 nucleic acid molecules (e.g., gene, cDNA, and mRNA) and proteins. MKI67 is a nuclear protein that is associated with cellular proliferation. Furthermore, it is associated with ribosomal RNA transcription. Inactivation of MKI67 leads to inhibition of ribosomal RNA synthesis. In particular examples, MKI67 expression, with the other 14 genes in Table 3 (but in some examples not including GABARAPL3), is correlated with HCC responsiveness to TACE.

MKI67 sequences are publically available. For example, GenBank Accession Nos. NM_002417.4, NM_001271366.1 and NM_001081117.2 disclose exemplary human, rat, and mouse MKI67 coding sequences, respectively. GenBank Accession Nos. P46013.2, P_001258295.1, and AAH53453.1 disclose exemplary human, rat, and mouse MKI67 protein sequences, respectively. One skilled in the art will appreciate that MKI67 nucleic acid and protein molecules analyzed using the disclosed methods can vary from those publicly available, while still being an MKI67 (e.g., the ability to generate asparagine from aspartate, and whose expression, with the other 14 genes in Table 3 (but in some examples not including GABARAPL3), is correlated with HCC responsiveness to TACE).

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe or antibody) will occur on the array a plurality of times (such as twice), for instance to provide internal controls. The number of addressable locations on the array can vary, for example from at least four, to at least 9, at least 10, at least 14, at least 15, at least 20, at least 30, at least 50, at least 75, at least 100, at least 150, at least 200, at least 300, at least 500, least 550, at least 600, at least 800, at least 1000, at least 10,000, or more. In a particular example, an array includes 5-100 addressable locations, such as 5-50 addressable locations. In particular examples, an array consists essentially of probes or primers or antibodies (such as those that permit amplification or detection) specific for ASNS, CDK1, DNASE1L3, FBXL5, GOT2, GRHPR, IARS, LGALS3, LHFPL2, MFGE8, MKI67, PEBP1, TNFSF10, and UBB, and in some examples, also GABARAPL3 and/or 1 to 10 or 1 to 6 control molecules (such as housekeeping genes, such as 1, 2, 3, 4, 5, or all of ACTB, B2M, EEF1A1, FTL, GUSB, and LDHA).

In particular examples, an array includes nucleic acid molecules, such as oligonucleotides that are at least 15 nucleotides in length, at least 30 nucleotides, at least 40 nucleotides, or at least 50 nucleotides in length.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including nucleic acids to which proteins are bound, or vice versa. In some examples, an array contains antibodies to 14 different TACE-associated molecules (ASNS, CDK1, DNASE1L3, FBXL5, GOT2, GRHPR, IARS, LGALS3, LHFPL2, MFGE8, MKI67, PEBP1, TNFSF10, and UBB), or 15 different TACE-associated molecules (GABARAPL3, ASNS, CDK1, DNASE1L3, FBXL5, GOT2, GRHPR, IARS, LGALS3, LHFPL2, MFGE8, MKI67, PEBP1, TNFSF10, and UBB) and in some examples also 1 to 10 housekeeping genes (such as antibodies specific for ACTB, B2M, EEF1A1, FTL, GUSB, and LDHA). In some examples, such antibodies are covalently attached to the array.

Asparagine synthetase (ASNS): e.g., OMIM 108370. Includes mammalian (such as human) ASNS nucleic acid molecules (e.g., gene, cDNA, and mRNA) and proteins. ASNS is an enzyme (EC 6.3.5.4) that generates asparagine from aspartate. In particular examples, ASNS expression, with the other 14 genes in Table 3 (but in some examples not including GABARAPL3), is correlated with HCC responsiveness to TACE.

ASNS sequences are publically available. For example, GenBank Accession Nos. M27396.1, M27838.1, and U38940.1 disclose exemplary human, hamster, and mouse ASNS coding sequences, respectively. GenBank Accession No. NM_183356.2 also discloses an exemplary human ASNS coding sequence. GenBank Accession Nos. AAA52756.1, AAA36977.1, and AAH05552.1 disclose exemplary human, hamster, and mouse ASNS protein sequences, respectively. One skilled in the art will appreciate that ASNS nucleic acid and protein molecules analyzed using the disclosed methods can vary from those publicly available, while still being an ASNS (e.g., the ability to generate asparagine from aspartate, and whose expression, with the other 14 genes in Table 3 (but in some examples not including GABARAPL3), is correlated with HCC responsiveness to TACE).

Beta-actin (ACTB): e.g., OMIM 102630. Includes mammalian (such as human) ACTB nucleic acid molecules (e.g., gene, cDNA, and mRNA) and proteins. ACTB is an isoform of cytoskeletal actin involved in cell motility, structure and integrity. In particular examples, ACTB expression can be used as a control with the disclosed methods, for example as a housekeeping gene with high expression which is similar in HCC tumor and non-tumor tissues.

ACTB sequences are publically available. For example, GenBank Accession Nos. NM_001101.3, NM_031144.3, and NM_007393.5 disclose exemplary human, rat, and mouse ACTB mRNA sequences, respectively. GenBank Accession Nos. NP_001092.1, NP_112406.1, and NP_031419.1 disclose exemplary human, rat, and mouse ACTB protein sequences, respectively. One skilled in the art will appreciate that ACTB nucleic acid and protein molecules analyzed using the disclosed methods can vary from those publicly available, while still being an ACTB (e.g., a housekeeping gene with high expression which is similar in HCC tumor and non-tumor tissues).

Beta-glucuronidase (GUSB): e.g., OMIM 61499. Includes mammalian (such as human) GUSB nucleic acid molecules (e.g., gene, cDNA, and mRNA) and proteins. GUSB is a lysosomal enzyme (EC 3.2.1.31) that digests glycosaminoglycans. In particular examples, GUSB expression can be used as a control with the disclosed methods, for example as a housekeeping gene with high expression which is similar in HCC tumor and non-tumor tissues.

GUSB sequences are publically available. For example, GenBank Accession Nos. NM_000181.3, NM_017015.2, and NM_010368.1 disclose exemplary human, rat, and mouse GUSB mRNA sequences, respectively. GenBank Accession Nos. NP_000172.2, NP_058711.2, and NP_034498.1 disclose exemplary human, rat, and mouse GUSB protein sequences, respectively. One skilled in the art will appreciate that GUSB nucleic acid and protein molecules analyzed using the disclosed methods can vary from those publicly available, while still being an GUSB (e.g., a housekeeping gene with high expression which is similar in HCC tumor and non-tumor tissues).

Beta-2-microglobulin (B2M): e.g., OMIM 109700. Includes mammalian (such as human) B2M nucleic acid molecules (e.g., gene, cDNA, and mRNA) and proteins. B2M is a serum protein found in association with the major histocompatibility complex (MHC) class I heavy chain on the surface of nearly all nucleated cells. In particular examples, B2M expression can be used as a control with the disclosed methods, for example as a housekeeping gene with high expression which is similar in HCC tumor and non-tumor tissues.

B2M sequences are publically available. For example, GenBank Accession Nos. NM_004048.2, NM_012512.2, and NM_009735.3 disclose exemplary human, rat, and mouse B2M mRNA sequences, respectively. GenBank Accession Nos. NP_004039.1, NP_036644.1, and NP_033865.2 disclose exemplary human, rat, and mouse B2M protein sequences, respectively. One skilled in the art will appreciate that B2M nucleic acid and protein molecules analyzed using the disclosed methods can vary from those publicly available, while still being an B2M (e.g., a housekeeping gene with high expression which is similar in HCC tumor and non-tumor tissues).

Binding or stable binding: An association between two substances or molecules, such as the hybridization of one nucleic acid molecule to another (or itself), the association of an antibody with a peptide, or the association of a protein with another protein or nucleic acid molecule. An oligonucleotide molecule binds or stably binds to a target nucleic acid molecule if a sufficient amount of the oligonucleotide molecule forms base pairs or is hybridized to its target nucleic acid molecule, to permit detection of that binding. "Preferentially binds" indicates that one molecule binds to another with high affinity, and binds to heterologous molecules at a low affinity.

Binding can be detected by any procedure known to one skilled in the art, such as by physical or functional properties of the target:oligonucleotide complex. For example, binding can be detected functionally by determining whether binding has an observable effect upon a biosynthetic process such as expression of a gene, DNA replication, transcription, translation, and the like.

Physical methods of detecting the binding of complementary strands of nucleic acid molecules, include but are not limited to, such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is a rapid increase in absorption at a characteristic temperature as the oligonucleotide (or analog) and target disassociate from each other, or melt. In another example, the method involves detecting a signal, such as one or more detectable labels, present on one or both nucleic acid molecules (or antibody or protein as appropriate). Methods of detecting binding of an antibody to a protein are routine, such as Western blotting.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Chronic viral infection: A viral infection of long duration or that recurs over a long period of time. Many cases of HCC are secondary to chronic hepatitis virus infection, such as chronic hepatitis infection, such as hepatitis B virus (HBV) or hepatitis C virus (HCV) infection.

Cirrhosis: A chronic progressive disease of the liver characterized by, the replacement of healthy cells with scar tissue. Many cases of HCC are secondary to cirrhosis of the liver. Cirrhosis can be caused by a variety of factors, such as alcoholism (chronic alcohol consumption), exposure to (e.g. ingestion of) aflatoxin (such as aflatoxin B1), or genetic disorders, such as inherited hemochromatosis. In some examples, a subject with cirrhosis and HCC is analyzed using the methods provided herein.

Clinical outcome: Refers to the health status of a patient following treatment for a disease or disorder, or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy (such as TACE).

Comparative genomic hybridization (CGH): A molecular-cytogenetic method for the analysis of copy number changes (gains/losses) in the DNA content of cells, such as tumor cells. The method is based on the hybridization of fluorescently labeled tumor DNA (such as, Fluorescein—FITC) and normal DNA (such as, Rhodamine or Texas Red) to normal human metaphase preparations. Using methods known in the art, such as epifluorescence microscopy and quantitative image analysis, regional differences in the fluorescence ratio of tumor versus control DNA can be detected and used for identifying abnormal regions in the tumor cell genome. CGH detects unbalanced chromosomes changes. Structural chromosome aberrations, such as balanced reciprocal translocations or inversions, are not detected, as they do not change the copy number. In one example, CGH includes the following steps. DNA from tumor tissue and from normal control tissue (reference) is labeled with different detectable labels, such as two different fluorophores. After mixing tumor and reference DNA along with unlabeled human cot 1 DNA to suppress repetitive DNA sequences, the mix is hybridized to normal metaphase chromosomes or, for array- or matrix-CGH, to a slide containing hundreds or thousands of defined DNA probes. The (fluorescence) color ratio along the chromosomes is used to evaluate regions of DNA gain or loss in the tumor sample.

Complementarity and percentage complementarity: Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide molecule remains detectably bound to a target nucleic acid sequence under the required conditions.

Complementarity is the degree to which bases in one nucleic acid strand base pair with the bases in a second nucleic acid strand. Complementarity is conveniently described by percentage, that is, the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

In the present disclosure, "sufficient complementarity" means that a sufficient number of base pairs exist between an oligonucleotide molecule and a target nucleic acid sequence to achieve detectable binding. When expressed or measured by percentage of base pairs formed, the percentage complementarity that fulfills this goal can range from as little as about 50% complementarity to full (100%) complementary. In general, sufficient complementarity is at least about 50%, for example at least about 75% complementarity, at least about 90% complementarity, at least about 95% complementarity, at least about 98% complementarity, or even at least about 100% complementarity.

A thorough treatment of the qualitative and quantitative considerations involved in establishing binding conditions that allow one skilled in the art to design appropriate oligonucleotides for use under the desired conditions is provided by Beltz et al. *Methods Enzymol.* 100:266-285, 1983, and by Sambrook et al. (ed.), *Molecular Cloning: A Laboratory Manual,* 2nd ed., vol. 1-3, Cold Spring Harbor Laboratory Press, Cold Spring Harbor, N.Y., 1989.

Consists essentially of: In the context of the present disclosure, "consists essentially of" indicates that the expression of additional TACE-associated genes can be evaluated, but not more than ten additional TACE-associated genes. In some examples, "consist essentially of" indicates that no more than 5 other molecules are evaluated, such as no more than 4, 3, 2, or 1 other molecules. In some examples, fewer than the recited molecules are evaluated, but not less than 5, 4, 3, 2 or 1 fewer molecules. In some examples, the expression of one or more controls is evaluated, such as a housekeeping gene/protein (such as ACTB, B2M, EEF1A1, FTL, GUSB, and/or LDHA). In this context "consist of" indicates that only the expression of the stated molecules are evaluated; the expression of additional molecules is not evaluated.

Contacting: Placement in direct physical association, including both solid and liquid forms. Contacting an agent with a cell can occur in vitro by adding the agent to isolated cells or in vivo by administering the agent to a subject.

Control: A "control" refers to a sample or standard used for comparison with an experimental sample, such as a tumor sample obtained from a patient with HCC. In some embodiments, the control is a sample obtained from a healthy patient or a non-tumor tissue sample obtained from a patient diagnosed with HCC (such as a normal non-tumor liver sample). In some embodiments, the control is a historical control or standard reference value or range of values (e.g., a previously tested control sample, such as a group of HCC patients who did or did not respond to TACE, or group of samples that represent baseline or normal values, such as the level of TACE-associated gene expression in non-tumor tissue).

Cyclin-dependent kinase 1 (CDK1): e.g., OMIM 116940. Also known as cell division cycle protein 2 homolog (CDC2). Includes mammalian (such as human) CDK1 nucleic acid molecules (e.g., gene, cDNA, and mRNA) and proteins. CDK1 forms complexes that phosphorylate a variety of target substrates, and phosphorylation of these proteins leads to cell cycle progression. In particular examples, CDK1 expression, with the other 14 genes in Table 3 (but in some examples not including GABARAPL3), is correlated with HCC responsiveness to TACE.

CDK1 sequences are publically available. For example, GenBank Accession Nos. NM_001786.4, NM_019296.1, and NM_007659.3 disclose exemplary human, rat, and mouse CDK1 coding sequences, respectively. GenBank Accession Nos. NP_001163877.1, NP_062169.1, and NP_031685.2 disclose exemplary human, rat, and mouse CDK1 protein sequences, respectively. One skilled in the art will appreciate that CDK1 nucleic acid and protein molecules analyzed using the disclosed methods can vary from those publicly available, while still being an CDK1 (e.g., the ability to phosphorylate a target substrate, and whose expression, with the other 14 genes in Table 3 (but in some examples not including GABARAPL3), is correlated with HCC responsiveness to TACE).

Decrease: To reduce the quality, amount, or strength of something. In one example, a therapy decreases a tumor (such as the size of a tumor, volume of a tumor, the number of tumors, the metastasis of a tumor, or combinations thereof), or one or more symptoms associated with a tumor, for example as compared to the response in the absence of the therapy. In a particular example, a therapy decreases the size of a tumor, volume of a tumor, the number of tumors, the metastasis of a tumor, or combinations thereof, subsequent to the therapy, such as a decrease of at least 10%, at least 20%, at least 50%, or even at least 90%. Such decreases can be measured using the methods disclosed herein.

Deoxyribonuclease I-like 3 (DNASE1L3): e.g., OMIM 602244. A member of the DNAse family Includes mammalian (such as human) DNASE1L3 nucleic acid molecules (e.g., gene, cDNA, and mRNA) and proteins. DNASE1L3 hydrolyzes DNA, and mediates the breakdown of DNA during apoptosis. In particular examples, DNASE1L3 expression, with the other 14 genes in Table 3 (but in some examples not including GABARAPL3), is correlated with HCC responsiveness to TACE.

DNASE1L3 sequences are publically available. For example, GenBank Accession Nos. NM_004944.3, NM_053907.1, and NM_007870.3 disclose exemplary human, rat, and mouse DNASE1L3 mRNA sequences, respectively. GenBank Accession No. NM_001256560 also discloses an exemplary human mRNA sequence. GenBank Accession Nos. AAH15831.1, EDL94170.1, and EDL20577.1 disclose exemplary human, rat, and mouse DNASE1L3 protein sequences, respectively. One skilled in the art will appreciate that DNASE1L3 nucleic acid and protein molecules analyzed using the disclosed methods can vary from those publicly available, while still being an DNASE1L3 (e.g., the ability to hydrolyze DNA, and whose expression, with the other 14 genes in Table 3 (but in some examples not including GABARAPL3), is correlated with HCC responsiveness to TACE).

Detecting or measuring expression: Determining the level expression in either a qualitative or quantitative manner by detection of nucleic acid molecules (e.g., at the genomic or mRNA level) or proteins. Exemplary methods include microarray analysis, PCR (such as RT-PCR), Northern blot, Western blot, ELISA, and mass spectrometry. In one example, the nCounter® method is used.

Diagnosis: The process of identifying a disease by its signs, symptoms and results of various tests. The conclusion reached through that process is also called "a diagnosis." Forms of testing commonly performed include blood tests, medical imaging, and biopsy.

Differential expression or altered expression: A difference, such as an increase or decrease, in the conversion of the information encoded in a gene (such as a TACE-associated gene) into messenger RNA, the conversion of mRNA to a protein, or both. In some examples, the difference is relative to a control or reference value (or range of values), such as the average expression value of a group of subjects, such as a HCCs that do not respond to TACE. The difference can also be relative to non-tumor tissue from the same subject or a healthy subject. Detecting differential expression can include measuring a change in gene or protein expression, such as a change in expression of one or more TACE-associated genes, such as an increase of at least 20%, at least 50%, at least 75%, at least 90%, at least 100%, at least 200%, at least 300% at least 400%, or at least 500%, or a decrease of at least 20%, at least 50%, at least 75%, at least 90%, or at least 95%.

Downregulated or decreased: When used in reference to the expression of a nucleic acid molecule, refers to any process which results in a decrease in production of a gene product. A gene product can be RNA (such as microRNA, mRNA, rRNA, tRNA, and structural RNA) or protein. Therefore, gene downregulation or deactivation includes processes that decrease transcription of a gene or translation of mRNA.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability.

Gene downregulation includes any detectable decrease in the production of a gene product. In certain examples, production of a gene product decreases by at least 2-fold, for example at least 3-fold or at least 4-fold, as compared to a control (such an amount of gene expression in a normal cell or in comparison to a reference value).

Elongation factor 1-alpha 1 (EEF1A1): e.g., OMIM 130590. Includes mammalian (such as human) EEF1A1 nucleic acid molecules (e.g., gene, cDNA, and mRNA) and proteins. EEF1A1 is an isoform of the alpha subunit of the elongation factor-1 complex, which is responsible for the enzymatic delivery of aminoacyl tRNAs to the ribosome. In particular examples, EEF1A1 expression can be used as a control with the disclosed methods, for example as a housekeeping gene with high expression which is similar in HCC tumor and non-tumor tissues.

EEF1A1 sequences are publically available. For example, GenBank Accession Nos. NM_001402.5, NM_175838.1, and NM_010106.2 disclose exemplary human, rat, and mouse EEF1A1 mRNA sequences, respectively. GenBank Accession Nos. NP_001393.1, NP_787032.1, and NP_034236.2 disclose exemplary human, rat, and mouse EEF1A1 protein sequences, respectively. One skilled in the art will appreciate that EEF1A1 nucleic acid and protein molecules analyzed using the disclosed methods can vary from those publicly available, while still being an EEF1A1 (e.g., a housekeeping gene with high expression which is similar in HCC tumor and non-tumor tissues).

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced. In an example, gene expression can be monitored to diagnose and/or prognose a subject with HCC, such as predict a subject's ability to respond to TACE.

The expression of a nucleic acid molecule can be altered relative to a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or subdomain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard. Controls or standards for comparison to a sample, for the determination of differential expression, include samples believed to be normal (in that they are not altered for the desired characteristic, for example a sample from a subject who does not have cancer, such as HCC) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

F-box and leucine-rich repeat protein 5 (FBXL5): e.g., OMIM 605655. Includes mammalian (such as human) FBXL5 nucleic acid molecules (e.g., gene, cDNA, and mRNA) and proteins. FBXL5 is an iron sensor that promotes iron-responsive element binding protein ubiquitination and degradation. In particular examples, FBXL5 expression, with the other 14 genes in Table 3 (but in some examples not including GABARAPL3), is correlated with HCC responsiveness to TACE.

FBXL5 sequences are publically available. For example, GenBank Accession Nos. NM_012161.3, NM_001193534.1, and NM_001159963.1 disclose exemplary human isoform 1, human isoform 3, rat, and mouse FBXL5 mRNA sequences, respectively. GenBank Accession Nos. NP_036293.1, NP 001180463.1, NP_001100692.1, and AAH47214.1 disclose exemplary human isoform 1, human isoform 3, rat, and mouse FBXL5 protein sequences, respectively. One skilled in the art will appreciate that FBXL5 nucleic acid and protein molecules analyzed using the disclosed methods can vary from those publicly available, while still being an FBXL5 (e.g., the ability to function as an iron sensor, and whose expression, with the other 14 genes in Table 3 (but in some examples not including GABARAPL3), is correlated with HCC responsiveness to TACE).

Ferritin light chain (FTL): e.g., OMIM 134790. Includes mammalian (such as human) FTL nucleic acid molecules (e.g., gene, cDNA, and mRNA) and proteins. FTL is the light subunit of the ferritin protein. Ferritin is the major intracellular iron storage protein. In particular examples, FTL expression can be used as a control with the disclosed methods, for example as a housekeeping gene with high expression which is similar in HCC tumor and non-tumor tissues.

FTL sequences are publically available. For example, GenBank Accession Nos. NM_000146.3, J02741.1, and J04716.1 disclose exemplary human, rat, and mouse FTL mRNA sequences, respectively. GenBank Accession Nos. NP_000137.2, AAA41155.1, and AAA37614.1 disclose exemplary human, rat, and mouse FTL protein sequences, respectively. One skilled in the art will appreciate that FTL nucleic acid and protein molecules analyzed using the disclosed methods can vary from those publicly available, while still being an FTL (e.g., a housekeeping gene with high expression which is similar in HCC tumor and non-tumor tissues).

GABA(A) receptors associated protein like 3, pseudogene (GABARAPL3): e.g., NCBI Gene ID 23766. Includes mammalian (such as human) GABARAPL3 nucleic acid molecules (e.g., gene, cDNA, and mRNA). GABARAPL3 is a non-coding RNA. In particular examples, GABARAPL3 expression, with the other 14 genes in Table 3, is correlated with HCC responsiveness to TACE.

GABARAPL3 sequences are publically available. For example, GenBank Accession No. NR_028287.1 discloses an exemplary human GABARAPL3 RNA sequence. One skilled in the art will appreciate that GABARAPL3 nucleic acid molecules analyzed using the disclosed methods can vary from those publicly available, while still being an GABARAPL3 (e.g., whose expression, with the other 14 genes in Table 3, is correlated with HCC responsiveness to TACE).

Gene expression profile (or fingerprint): Differential or altered gene expression can be detected by changes in the detectable amount of gene expression (such as cDNA or mRNA) or by changes in the detectable amount of proteins expressed by those genes. A distinct or identifiable pattern of gene expression, for instance a pattern of high and/or low expression of a defined set of genes or gene-indicative nucleic acids such as ESTs; in some examples, the TACE profile in Table 3 (but in some examples not including GABARAPL3). A gene expression profile (also referred to as a fingerprint) can be linked to a tissue or cell type (such as HCC), to a response to a therapy (such as TACE), or to any other distinct or identifiable condition that influences gene expression. Gene expression profiles can include relative as well as absolute expression levels of specific genes, and can be viewed in the context of a test sample compared to a baseline or control sample profile (such as a sample from a subject who does not have HCC). In one example, a gene expression profile in a subject is read on an array (such as a nucleic acid or protein array).

Hepatocellular carcinoma (HCC): HCC is a primary malignancy of the liver, which in some cases occurs in patients with inflammatory livers resulting from viral hepatitis, liver toxins or hepatic cirrhosis (often caused by alcoholism). Exemplary therapies for HCC include but are not limited to: one or more of surgery, transarterial chemoembolization (TACE), ablative therapies (including both thermal and cryoablation), radio embolization, and percutaneous alcohol injection.

Glutamic-oxaloacetic transaminase 2, mitochondrial (GOT2): e.g., OMIM 138150. Includes mammalian (such as human) GOT2 nucleic acid molecules (e.g., gene, cDNA, and mRNA) and proteins. GOT2 (EC 2.6.1.1) is a pyridoxal phosphate-dependent enzyme, participating in the malate-aspartate shuttle, which is a passage from the cytosol to the mitochondria. GOT2 may have a role in cell proliferation, such as tumor growth. In particular examples, GOT2 expression, with the other 14 genes in Table 3 (but in some examples not including GABARAPL3), is correlated with HCC responsiveness to TACE.

GOT2 sequences are publically available. For example, GenBank Accession Nos. NM_002080.3, NM_001286220.1, NM_174806.2 and NM_010325.2 disclose exemplary human isoform 1, human isoform 2, cow, and mouse GOT2 mRNA sequences, respectively. GenBank Accession Nos. NP_002071.2, NP_001273149.1, NP_777231.1, and NP_034455.1 disclose exemplary human isoform 1, human isoform 3, rat, and mouse GOT2 protein sequences, respectively. One skilled in the art will appreciate that GOT2 nucleic acid and protein molecules analyzed using the disclosed methods can vary from those publicly available, while still being an GOT2 (e.g., the ability to participate in the malate-aspartate shuttle, and whose expression, with the other 14 genes in Table 3 (but in some examples not including GABARAPL3), is correlated with HCC responsiveness to TACE).

Glyoxylate-reductase/hydroxypyruvate reductase (GRHPR): e.g., OMIM 604296. Includes mammalian (such as human) GRHPR nucleic acid molecules (e.g., gene, cDNA, and mRNA) and proteins. GRHPR (EC 1.1.1.79) is an enzyme with hydroxypyruvate reductase, glyoxylate reductase, and D-glycerate dehydrogenase enzymatic activities. In particular examples, GRHPR expression, with the other 14 genes in Table 3 (but in some examples not including GABARAPL3), is correlated with HCC responsiveness to TACE.

GRHPR sequences are publically available. For example, GenBank Accession Nos. NM_012203.1, NM_001113754.1, and AY113690.1 disclose exemplary human, rat, and mouse GRHPR mRNA sequences, respectively. GenBank Accession Nos. NP_036335.1, AAI586881.1, and NP_525028.1 disclose exemplary human, rat, and mouse GRHPR protein sequences, respectively. One skilled in the art will appreciate that GRHPR nucleic acid and protein molecules analyzed using the disclosed methods can vary from those publicly available, while still being an GRHPR (e.g., having hydroxypyruvate reductase, glyoxylate reductase, and D-glycerate dehydrogenase enzymatic activities, and whose expression, with the other 14 genes in Table 3 (but in some examples not including GABARAPL3), is correlated with HCC responsiveness to TACE).

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (detects sequences that share at least 90% identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (detects sequences that share at least 80% identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (detects sequences that share at least 60% identity)
Hybridization: 6×SSC at RT to 55° C. for 16-20 hours
Wash at least twice: 2×-3×SSC at RT to 55° C. for 20-30 minutes each Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

Isoleucyl-tRNA synthetase (IARS): e.g., OMIM 600709. Includes mammalian (such as human) IARS nucleic acid molecules (e.g., gene, cDNA, and mRNA) and proteins. IARS (EC 6.1.1.5) is an enzyme that catalyzes the aminoacylation of tRNA by their cognate amino acid. In particular examples, IARS expression, with the other 14 genes in Table 3 (but in some examples not including GABARAPL3), is correlated with HCC responsiveness to TACE.

IARS sequences are publically available. For example, GenBank Accession Nos. U04953.1, NM_001100572.1 and NM_172015.3 disclose exemplary human, rat, and mouse IARS coding sequences, respectively. GenBank Accession No. NM_002161.3 also encodes an exemplary human coding sequence. GenBank Accession Nos. AAA80153.1, NP_001094042.1, and NP_742012.2 disclose exemplary human, rat, and mouse IARS protein sequences, respectively. One skilled in the art will appreciate that IARS nucleic acid and protein molecules analyzed using the disclosed methods can vary from those publicly available, while still being an IARS (e.g., the ability to catalyze the aminoacylation of tRNA by their cognate amino acid, and whose expression, with the other 14 genes in Table 3 (but in some examples not including GABARAPL3), is correlated with HCC responsiveness to TACE).

Label: An agent capable of detection, for example by ELISA, spectrophotometry, flow cytometry, or microscopy. For example, a label can be attached (such as covalently attached) to a nucleic acid molecule (such as a nucleic acid probe) or protein, thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In particular examples, a label is conjugated to a binding agent that specifically binds to one or more of the TACE-associated molecules.

Lactate dehydrogenase A (LDHA): e.g., OMIM 150000. Includes mammalian (such as human) LDHA nucleic acid molecules (e.g., gene, cDNA, and mRNA) and proteins. LDHA is an enzyme (EC 1.1.1.27) that catalyzes the inter-conversion of pyruvate and L-lactate with concomitant inter-conversion of NADH and NAD+. In particular examples, LDHA expression can be used as a control with the disclosed methods, for example as a housekeeping gene with high expression which is similar in HCC tumor and non-tumor tissues.

LDHA sequences are publically available. For example, GenBank Accession Nos. AY581313.1, NM_001135239.1, NM_012595.2, and M17516.1 disclose exemplary human, human rat, and mouse LDHA mRNA sequences, respectively. GenBank Accession No. NM_001165414.1 also discloses an exemplary human coding sequence. GenBank Accession Nos. NP_001128711.1, AAH67223.1, AAI68737.1, and NP_001129541.2 disclose exemplary human isoform 2, human, rat, and mouse LDHA protein sequences, respectively. One skilled in the art will appreciate that LDHA nucleic acid and protein molecules analyzed using the disclosed methods can vary from those publicly available, while still being an LDHA (e.g., a housekeeping gene with high expression which is similar in HCC tumor and non-tumor tissues).

Lectin, galactoside-binding, soluble 3 (LGALS3): e.g., OMIM 153619. Also known as galectin-3. Includes mammalian (such as human) LGALS3 nucleic acid molecules (e.g., gene, cDNA, and mRNA) and proteins. LGALS3 is a galectin that binds to beta-galactosides, that plays a role in cell-cell adhesion, cell-matrix interactions, macrophage activation, angiogenesis, metastasis, and apoptosis. In particular examples, LGALS3 expression, with the other 14 genes in Table 3 (but in some examples not including GABARAPL3), is correlated with HCC responsiveness to TACE.

LGALS3 sequences are publically available. For example, GenBank Accession Nos. CR542097.1, NM_031832.1 and NM_001145953.1 disclose exemplary human, rat, and mouse LGALS3 coding sequences, respectively. GenBank Accession No. NM_001177388.1 also discloses an exemplary human coding sequence. GenBank Accession Nos. CAG33178.1, NP_114020.1, and NP_001139425.1 disclose exemplary human, rat, and mouse LGALS3 protein sequences, respectively. One skilled in the art will appreciate that LGALS3 nucleic acid and protein molecules analyzed using the disclosed methods can vary from those publicly available, while still being an LGALS3 (e.g., the ability to bind to beta-galactosides, and whose expression, with the other 14 genes in Table 3 (but in some examples not including GABARAPL3), is correlated with HCC responsiveness to TACE).

Lipoma HMGIC fusion partner-like 2 protein (LHFPL2): e.g., OMIM 609718. Includes mammalian (such as human) LHFPL2 nucleic acid molecules (e.g., gene, cDNA, and mRNA) and proteins. LHFPL2 is a member of the superfamily of tetraspan transmembrane protein encoding genes. In particular examples, LHFPL2 expression, with the other 14 genes in Table 3 (but in some examples not including GABARAPL3), is correlated with HCC responsiveness to TACE.

LHFPL2 sequences are publically available. For example, GenBank Accession Nos. NM_005779.2, NM_001106402.1 and NM_172589.2 disclose exemplary human, rat, and mouse LHFPL2 coding sequences, respectively. GenBank Accession Nos. NP_005770.1, NP_001099872.1, and NP_766177.1 disclose exemplary human, rat, and mouse LHFPL2 protein sequences, respectively. One skilled in the art will appreciate that LHFPL2 nucleic acid and protein molecules analyzed using the disclosed methods can vary from those publicly available, while still being an LHFPL2 (e.g., the ability to function as a transmembrane protein, and whose expression, with the other 14 genes in Table 3 (but in some examples not including GABARAPL3), is correlated with HCC responsiveness to TACE).

Malignant: Cells that have the properties of anaplasia, invasion and metastasis.

Mammal: This term includes both human and non-human mammals Examples of mammals include, but are not limited to: humans, pigs, cows, goats, cats, dogs, rabbits and mice.

Milk fat globule-EGF factor 8 protein (MFGE8): e.g., OMIM 602281. Also known as lactadherin. Includes mammalian (such as human) MFGE8 nucleic acid molecules (e.g., gene, cDNA, and mRNA) and proteins. MFGE8 may function as a cell adhesion protein to connect smooth muscle to elastic fiber in arteries. In particular examples, MFGE8 expression, with the other 14 genes in Table 3 (but in some examples not including GABARAPL3), is correlated with HCC responsiveness to TACE.

MFGE8 sequences are publically available. For example, GenBank Accession Nos. NM_005928.3, NM_001114614.2, NM_001040186.2 and NM_001045489.1 disclose exemplary human transcript 1, human transcript 2, rat, and mouse MFGE8 coding sequences, respectively. GenBank Accession Nos. AAH03610.1, P70490.1, and NP_001038954.1 disclose exemplary human, rat, and mouse MFGE8 protein sequences, respectively. One skilled in the art will appreciate that MFGE8 nucleic acid and protein molecules analyzed using the disclosed methods can vary from those publicly available, while still being an MFGE8 (e.g., the ability to function as a cell adhesion protein, and whose expression, with the other 14 genes in Table 3 (but in some examples not including GABARAPL3), is correlated with HCC responsiveness to TACE).

Nucleic acid array: An arrangement of nucleic acids (such as DNA or RNA) in assigned locations on a matrix, such as that found in cDNA arrays, mRNA arrays, or oligonucleotide arrays. In some examples, the nucleic acid molecules are attached covalently to the array.

Oligonucleotide: A plurality of joined nucleotides joined by native phosphodiester bonds, for example between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide.

Figure 8B:
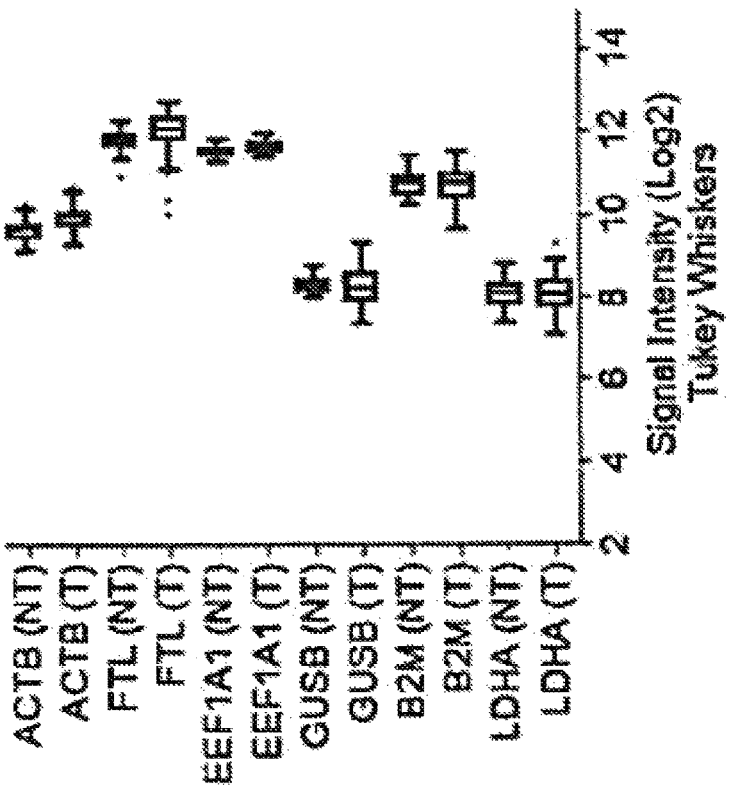
FIG. 8B is a graph showing expression of six different housekeeping genes in tumor (T) and non-tumor (NT) samples from an TIGER cohort.
Figure 8A:
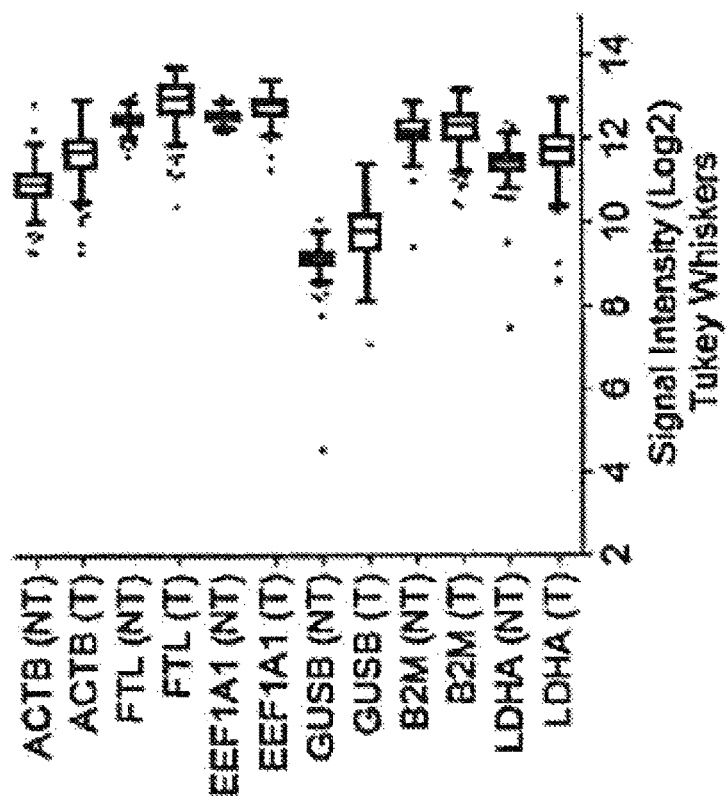
FIG. 8A is a graph showing expression of six different housekeeping genes in tumor (T) and non-tumor (NT) samples from an LCI cohort.

Particular oligonucleotides and oligonucleotide analogs can include linear sequences up to about 200 nucleotides in length, for example a sequence (such as DNA or RNA) that is at least 6 nucleotides, for example at least 8, at least 10, at least 15, at least 20, at least 21, at least 25, at least 30, at least 35, at least 40, at least 45, at least 50, at least 100 or even at least 200 nucleotides long, or from about 6 to about 50 nucleotides, for example about 10-25 nucleotides, such as 12, 15 or 20 nucleotides. In one example, an oligonucleotide is a short sequence of nucleotides of at least one of the disclosed TACE-associated genes, such as ASNS, CDK1, DNASE1L3, FBXL5, GABARAPL3, GOT2, GRHPR, IARS, LGALS3, LHFPL2, MFGE8, MKI67, PEBP1, TNFSF10, and UBB, or one of the housekeeping genes shown in FIG. 8A.

Oligonucleotide probe: A sequence of nucleotides, such as at least 8, at least 10, at least 15, at least 20, at least 21, at least 25, at least 30, at least 40, at least 50, or at least 55 nucleotides in length, used to detect the presence of a complementary sequence by molecular hybridization. In particular examples, oligonucleotide probes include one or more labels that permits detection of oligonucleotide probe: target sequence hybridization complexes. In one example, an oligonucleotide probe is used to detect the presence of the disclosed TACE-associated genes, such as ASNS, CDK1, DNASE1L3, FBXL5, GABARAPL3, GOT2, GRHPR, IARS, LGALS3, LHFPL2, MFGE8, MKI67, PEBP1, TNFSF10, and/or UBB, as well as the housekeeping genes shown in FIG. 8A.

Phosphatidylethanolamine binding protein 1 (PEBP1): e.g., OMIM 604591. Includes mammalian (such as human) PEBP1 nucleic acid molecules (e.g., gene, cDNA, and mRNA) and proteins. PEBP1 encodes a member of the phosphatidylethanolamine-binding family of proteins and has been shown to modulate multiple signaling pathways, including the MAP kinase (MAPK), NF-κB, and glycogen synthase kinase-3 (GSK-3) signaling pathways. In particular examples, PEBP1 expression, with the other 14 genes in Table 3 (but in some examples not including GABARAPL3), is correlated with HCC responsiveness to TACE.

PEBP1 sequences are publically available. For example, GenBank Accession Nos. NM_002567.3, NM_017236.1, and NM_018858.2 disclose exemplary human, rat, and mouse PEBP1 coding sequences, respectively. GenBank Accession Nos. NP_002558.1, P31044.3, and NP_061346.2 disclose exemplary human, rat, and mouse PEBP1 protein sequences, respectively. One skilled in the art will appreciate that PEBP1 nucleic acid and protein molecules analyzed using the disclosed methods can vary from those publicly available, while still being an PEBP1 (e.g., the ability to modulate the MAPK, NF-κB, and/or GSK-3 signaling pathways, and whose expression, with the other 14 genes in Table 3 (but in some examples not including GABARAPL3), is correlated with HCC responsiveness to TACE).

Polymerase Chain Reaction (PCR): An in vitro amplification technique that increases the number of copies of a nucleic acid molecule (for example, a nucleic acid molecule in a sample or specimen). In an example, a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of a PCR can be characterized by electrophoresis, restriction endonuclease cleavage patterns, oligonucleotide hybridization or ligation, and/or nucleic acid sequencing, using standard techniques or other standard techniques known in the art.

Primers: Short nucleic acid molecules, for instance DNA oligonucleotides 10 to 100 nucleotides in length, such as about 15, 20, 25, 30 or 50 nucleotides or more in length. Primers can be annealed to a complementary target DNA strand by nucleic acid hybridization to form a hybrid between the primer and the target DNA strand. Primer pairs can be used for amplification of a nucleic acid sequence, such as by PCR or other nucleic acid amplification methods known in the art.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length. Thus, in order to obtain greater specificity, primers can be selected that include at least 20, at least 25, at least 30, at least 35, at least 40, at least 45, at least 50 or more consecutive nucleotides of target nucleic acid sequence (such as a TACE-associated molecule).

Prognosis: A prediction of the course of a disease, such as HCC. The prediction can include determining the likelihood of a subject to develop aggressive, recurrent disease, to survive a particular amount of time (e.g. determine the likelihood that a subject will survive 1, 2, 3 or 5 years), to respond to a particular therapy (e.g., TACE), or combinations thereof.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified mRNA preparation is one in which the mRNA is more pure than in an environment including a complex mixture of nucleic acid molecules.

Sample (or biological sample): A biological specimen containing genomic DNA, RNA (including mRNA), protein, or combinations thereof, obtained from a subject. Examples include, but are not limited to, peripheral blood, urine, saliva, tissue biopsy, fine needle aspirate, punch biopsy surgical specimen, and autopsy material. In one example, a sample includes a HCC biopsy.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Queries searched with the blastn program are filtered with DUST (Hancock and Armstrong, 1994, *Comput. Appl. Biosci.* 10:67-70). Other programs may use SEG. In addition, a manual alignment can be performed. Proteins with even greater similarity will show increasing percentage identities when assessed by this method. Thus, in some examples, expression of an ASNS, CDK1, DNASE1L3, FBXL5, GABARAPL3, GOT2, GRHPR, IARS, LGALS3, LHFPL2, MFGE8, MKI67, PEBP1, TNFSF10, UBB, ACTB, B2M, EEF1A1, FTL, GUSB, or LDHA protein having at least 80%, at least 85%, at least 90%, at least 95%, at least 98%, or at least 99% sequence identity to a native ASNS, CDK1, DNASE1L3, FBXL5, GABARAPL3, GOT2, GRHPR, IARS, LGALS3, LHFPL2, MFGE8, MKI67, PEBP1, TNFSF10, UBB, ACTB, B2M, EEF1A1, FTL, GUSB, or LDHA protein sequence, while retaining the biological function of the protein, can be examined using the disclosed methods.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. An alternative (and not necessarily cumulative) indication that two nucleic acid sequences are substantially identical is that the polypeptide which the first nucleic acid encodes is immunologically cross reactive with the polypeptide encoded by the second nucleic acid. Thus, in some examples, expression of an ASNS, CDK1, DNASE1L3, FBXL5, GABARAPL3, GOT2, GRHPR, IARS, LGALS3, LHFPL2, MFGE8, MKI67, PEBP1, TNFSF10, UBB, ACTB, B2M, EEF1A1, FTL, GUSB, or LDHA nucleic acid (such as mRNA, cDNA, or gene) having at least 80%, at least 85%, at least 90%, at least 95%, at least 98%, or at least 99% sequence identity to a native ASNS, CDK1, DNASE1L3, FBXL5, GABARAPL3, GOT2, GRHPR, IARS, LGALS3, LHFPL2, MFGE8, MKI67, PEBP1, TNFSF10, UBB, ACTB, B2M, EEF1A1, FTL, GUSB, or LDHA nucleic acid (such as mRNA, cDNA, or gene) sequence can be examined using the disclosed methods. One of skill in the art will appreciate that the particular sequence identity ranges are provided for guidance only.

Specific binding agent: An agent that binds substantially or preferentially only to a defined target such as a protein, enzyme, polysaccharide, oligonucleotide, DNA, RNA, recombinant vector or a small molecule. In an example, a "specific binding agent" is capable of binding to at least one of ASNS, CDK1, DNASE1L3, FBXL5, GABARAPL3, GOT2, GRHPR, IARS, LGALS3, LHFPL2, MFGE8, MKI67, PEBP1, TNFSF10, UBB, ACTB, B2M, EEF1A1, FTL, GUSB, and LDHA.

Thus, a nucleic acid-specific binding agent binds substantially only to the defined nucleic acid, such as mRNA or a gene sequence, or to a specific region within the nucleic acid. A protein-specific binding agent binds substantially only the defined protein, or to a specific region within the protein. For example, a "specific binding agent" includes antibodies and other agents that bind substantially to a specified polypeptide. Antibodies include monoclonal or polyclonal antibodies that are specific for the polypeptide, as well as immunologically effective portions ("fragments") thereof. The determination that a particular agent binds substantially only to a specific target may readily be made by using routine procedures. Exemplary suitable in vitro assays include Western blotting and nucleic acid hybridization procedures.

Subject: Living multi-cellular vertebrate organisms, a category that includes human and non-human mammals. In one example, a subject has HCC.

Target sequence: A sequence of nucleotides located in a particular region in the human genome that corresponds to a desired sequence, such as a TACE-associated gene, for example, ASNS, CDK1, DNASE1L3, FBXL5, GABARAPL3, GOT2, GRHPR, IARS, LGALS3, LHFPL2, MFGE8, MKI67, PEBP1, TNFSF10, or UBB. Target sequences can encode target proteins, or can be a non-coding RNA. The target can be for instance a coding sequence; it can also be the non-coding strand that corresponds to a coding sequence. Examples of target sequences include those sequences associated with responsiveness of HCC to TACE.

Therapeutically effective amount: An amount of a composition that alone, or together with an additional therapeutic agent(s) (for example a chemotherapeutic agent), induces the desired response (e.g., treatment of a tumor). The preparations disclosed herein are administered in therapeutically effective amounts. In one example, a desired response is to decrease tumor size or volume or metastasis in a subject to whom the therapy is administered. The tumor or metastasis thereof does not need to be completely eliminated for the composition to be effective. For example, a composition can decrease the size or volume of a tumor or the metastasis of the tumor by at least 20%, at least 50%, at least 60%, at least 70%, at least 80%, at least 90%, at least 95%, at least 98%, or even at least 100% (elimination of the tumor), as compared to the size or volume of the tumor or metastasis in the absence of the therapy.

In particular examples, it is an amount of the therapeutic agent effective to decrease the number of tumor cells, such as the number of tumor cells in a patient with HCC. The tumor cells do not need to be completely eliminated for the composition to be effective. For example, a composition can decrease the number of tumor cells by a desired amount, for example by at least 20%, at least 50%, at least 60%, at least 70%, at least 80%, at least 90%, at least 95%, at least 98%, or even at least 100% (elimination of detectable tumor cells), as compared to the number of tumor cells in the absence of the composition.

A therapeutically effective amount of a therapeutic agent can be administered in a single dose, or in several doses, for example daily, during a course of treatment. However, the therapeutically effective amount can depend on the subject being treated, the severity and type of the condition being treated, the manner of administration and the type of therapeutic agent being administered.

Tissue: A plurality of functionally related cells. A tissue can be a suspension, a semi-solid, or solid. Tissue includes cells collected from a subject, such as from the liver.

Transarterial catheter chemoembolization (TACE): A procedure used to treat a tumor, such as HCC, for example by restricting tumor's blood supply. In such treatment, small embolic particles coated with chemotherapeutic agents are injected selectively into an artery supplying the tumor (such as the hepatic artery). In some examples, such methods allow for a higher dose of chemotherapy to be administered. Examples of such particles and chemotherapeutic agents that can be used, include but are not limited to: polyvinyl alcohol microspheres (e.g., loaded with doxorubicin), superabsorbent polymer microspheres (e.g., loaded with doxorubicin), and gelatin microspheres (e.g., loaded with cisplatin). Additional information can be found in Van Ha (*Semin Intervent Radiol.* 2009 September; 26(3): 270-275). In some examples, TACE uses one or more of cisplatin, Adriamycin, mitomycin, and doxorubicin. In one example, TACE uses cisplatin, adriamycin and mitomycin (CAM).

TACE-associated molecule: As used herein, a "TACE-associated molecule" is a gene or protein whose expression or activity is altered in HCC tumors that are responsive to TACE therapy relative to a control or reference standard (such as HCC tumors that are not responsive to TACE therapy). In the context of the present disclosure, TACE-associated molecules include and in some examples consist essentially of or consist of the ASNS, CDK1, DNASE1L3, FBXL5, GOT2, GRHPR, IARS, LGALS3, LHFPL2, MFGE8, MKI67, PEBP1, TNFSF10, and UBB genes, or the proteins encoded by these genes. In some examples, TACE-associated molecules include and in some examples consist essentially of or consist of the ASNS, CDK1, DNASE1L3, FBXL5, GABARAPL3, GOT2, GRHPR, IARS, LGALS3, LHFPL2, MFGE8, MKI67, PEBP1, TNFSF10, and UBB genes, or the proteins encoded by these genes. Accordingly, "TACE-associated genes" refers to ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3) and "TACE-associated proteins" refers to the proteins encoded by ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3).

Treating a disease: "Treatment" refers to a therapeutic intervention that ameliorates a sign or symptom of a disease or pathological condition, such as a sign or symptom of HCC. Treatment can also induce remission or cure of a condition, such as HCC. Treatment of a disease does not require a total absence of disease. For example, reduction in tumor size and/or volume, and/or decreases in the number metastases, size and/or volume of a metastasis, such as a decrease of at least 20%, at least 50%, at least 75%, or at least 90% can be sufficient. In some examples, treating a disease improves the prognosis of the HCC patient, for example by increasing the predicted survival time of the HCC patient.

Tumor: All neoplastic cell growth and proliferation, whether malignant or benign, and all pre-cancerous and cancerous cells and tissues. In an example, a tumor is a HCC tumor.

Tumor necrosis factor superfamily, member 10 (TNFSF10): e.g., OMIM 603598. Also known as tumor necrosis factor-related apoptosis-inducing ligand (TRAIL). Includes mammalian (such as human) TNFSF10 nucleic acid molecules (e.g., gene, cDNA, and mRNA) and proteins. TNFSF10 is a cytokine that induces the apoptosis. In particular examples, TNFSF10 expression, with the other 14 genes in Table 3 (but in some examples not including GABARAPL3), is correlated with HCC responsiveness to TACE.

TNFSF10 sequences are publically available. For example, GenBank Accession Nos. CR456895.1, NM_145681.2, NM_009425.2 disclose exemplary human, rat, and mouse TNFSF10 coding sequences, respectively. GenBank Accession No. NM_003810.2 also discloses an exemplary human coding sequence. GenBank Accession Nos. CAG33176.1, NP_663714.2, and NP_033451.1 disclose exemplary human, rat, and mouse TNFSF10 protein sequences, respectively. One skilled in the art will appreciate that TNFSF10 nucleic acid and protein molecules analyzed using the disclosed methods can vary from those publicly available, while still being an TNFSF10 (e.g., the ability to induce apoptosis, and whose expression, with the other 14 genes in Table 3 (but in some examples not including GABARAPL3), is correlated with HCC responsiveness to TACE).

Ubiquitin B (UBB): e.g., OMIM 191339. Includes mammalian (such as human) UBB nucleic acid molecules (e.g., gene, cDNA, and mRNA) and proteins. UBB is required for ATP-dependent, non-lysosomal intracellular protein degradation of abnormal proteins and normal proteins with a rapid turnover. In particular examples, UBB expression, with the other 14 genes in Table 3 (but in some examples not including GABARAPL3), is correlated with HCC responsiveness to TACE.

UBB sequences are publically available. For example, GenBank Accession Nos. BC038999.1, BC060312.1, and BC100341.1 disclose exemplary human, rat, and mouse UBB coding sequences, respectively. GenBank Accession No. NM_018955.2 also discloses an exemplary human coding sequence. GenBank Accession Nos. AAH38999.1, AAH60312.1, and AAI00342.1 disclose exemplary human, rat, and mouse UBB protein sequences, respectively. One skilled in the art will appreciate that UBB nucleic acid and protein molecules analyzed using the disclosed methods can vary from those publicly available, while still being an UBB (e.g., the ability to degrade proteins, and whose expression, with the other 14 genes in Table 3 (but in some examples not including GABARAPL3), is correlated with HCC responsiveness to TACE).

Under conditions sufficient for: A phrase that is used to describe any environment that permits the desired activity. In one example, includes administering one or more chemotherapeutic agent to a subject with HCC sufficient to allow the desired activity, such as treatment of the HCC.

Upregulated, activated or increased: When used in reference to the expression of a nucleic acid molecule, such as a gene, refers to any process which results in an increase in production of a gene product. A gene product can be RNA (such as mRNA, rRNA, tRNA, and structural RNA) or protein. Therefore, gene upregulation or activation includes processes that increase transcription of a gene or translation of mRNA.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). *Gene* upregulation can include inhibition of repression as well as stimulation of expression above an existing level. Examples of processes that increase translation include those that increase translational initiation, those that increase translational elongation and those that increase mRNA stability.

Gene upregulation includes any detectable increase in the production of a gene product. In certain examples, production of a gene product increases by at least 2-fold, for example at least 3-fold or at least 4-fold, as compared to a control (such an amount of gene expression in a normal cell). In one example, a control is a relative amount of gene expression in a biological sample, such as in a liver tissue biopsy obtained from a subject that does not have HCC.

III. Overview

This disclosure provides the first unique genetic signature module that predicts the response of patients with hepatocellular carcinoma (HCC) to transarterial catheter chemoembolization (TACE) treatment.

Disclosed herein are methods of detecting expression of a plurality of genes, for example which indicate whether a hepatocellular carcinoma (HCC) will respond to transarterial chemoembolization (TACE). In some embodiments, the method includes or consists of detecting expression of ASNS, CDK1, DNASE1L3, FBXL5, GOT2, GRHPR, JARS, LGALS3, LHFPL2, MFGE8, MKI67, PEBP1, TNFSF10, and UBB (and optionally GABARAPL3) in an HCC sample obtained from a subject diagnosed with HCC, relative to a control. In some examples, a modulation (increase or decrease) in expression of ASNS, CDK1, DNASE1L3, FBXL5, GOT2, GRHPR, JARS, LGALS3, LHFPL2, MFGE8, MKI67, PEBP1, TNFSF10 and UBB (and optionally GABARAPL3), relative to the control indicates the HCC will respond to TACE. In specific non-limiting examples, an increase in expression of ASNS, CDK1, FBXL5, JARS, LGALS3, LHFPL2, MKI67, and UBB and a decrease in expression of DNASE1L3, GOT2, GRHPR, MFGE8, PEBP1, and TNFSF10 (and optionally GABARAPL3) relative to the control indicates the HCC will respond to TACE.

In some examples, methods are provided that include detecting or measuring increased expression of ASNS, CDK1, FBXL5, JARS, LGALS3, LHFPL2, MKI67, and UBB in the sample relative to the control; detecting or measuring decreased expression of DNASE1L3, GOT2, GRHPR, MFGE8, PEBP1, and TNFSF10 (and optionally GABARAPL3) relative to the control; and administering TACE treatment to the subject from whom the sample was obtained and in some examples also surgically removing all or part of the HCC in the subject.

Any of the disclosed methods can further include measuring or determining the AFP concentration in the blood of the test subject (e.g., whether the subject is AFP positive or negative).

In some examples of the disclosed methods, the modulation in expression (the increase or decrease) is at least about 1.5-fold, at least about 2-fold, at least about 2.5-fold, at least about 3-fold, at least about 4-fold or at least about 5-fold relative to the control.

In some embodiments, the method further includes detecting expression of at least 1, 2, 3, 4, 5, 6, 7, 8, 9 or 10, such as about 1 to about 10, or about 1 to about 6, housekeeping genes or proteins. In some examples, the housekeeping genes or proteins include 1, 2, 3, 4, 5 or 6 of ACTB, B2M, EEF1A1, FTL, GUSB and LDHA.

In some embodiments of the method, the control is a reference value or a non-tumor tissue sample. In some examples, the non-tumor tissue sample is non-tumor liver tissue from the subject with HCC or liver tissue from a healthy subject.

In some embodiments, the subject diagnosed with HCC has a chronic viral infection. In some embodiments, the subject diagnosed with HCC has cirrhosis of the liver.

In some embodiments of the disclosed methods, detecting gene expression includes detecting a level of ASNS, CDK1, DNASE1L3, FBXL5, GOT2, GRHPR, IARS, LGALS3, LHFPL2, MFGE8, MKI67, PEBP1, TNFSF10, and UBB mRNA using a microscope device. In some examples, detecting gene expression further includes detecting a level of GABARAPL3 using a microscope device.

In some embodiments, the method further includes converting gene expression values to a z-score. In some examples, the method further includes applying a prognostic index equation to predict whether the HCC will respond to TACE (see FIG. 3A and Examples 1 and 2).

Also disclosed herein are probe sets. In some embodiments, the probe set includes at least one nucleic acid probe specific for each of ASNS, CDK1, DNASE1L3, FBXL5, GOT2, GRHPR, IARS, LGALS3, LHFPL2, MFGE8, MKI67, PEBP1, TNFSF10, and UBB. In some examples, the probe set further includes one or more nucleic acid probes specific for GABARAPL3. In some examples, the probe set further includes nucleic acid probes specific for at least 1, 2, 3, 4, 5, 6, 7, 8, 9 or 10, such as about 1 to about 10, or about 1 to about 6, housekeeping genes. In specific non-limiting examples, the housekeeping genes include 1, 2, 3, 4, 5 or 6 of ACTB, B2M, EEF1A1, FTL, GUSB and LDHA. In one specific example, the probe set includes a nucleic acid probe specific for each of ASNS, CDK1, DNASE1L3, FBXL5, GOT2, GRHPR, IARS, LGALS3, LHFPL2, MFGE8, MKI67, PEBP1, TNFSF10, UBB, ACTB, B2M, EEF1A1, FTL, GUSB, and LDHA. In another specific example, the probe set includes a nucleic acid probe specific for each of ASNS, CDK1, DNASE1L3, FBXL5, GABARAPL3, GOT2, GRHPR, IARS, LGALS3, LHFPL2, MFGE8, MKI67, PEBP1, TNFSF10, UBB, ACTB, B2M, EEF1A1, FTL, GUSB, and LDHA.

In some embodiments, the nucleic acid probe comprises a capture probe and a reporter probe, wherein the reporter probe comprises one or more detectable labels. In some examples, the capture probe includes a molecule that allows immobilization of target:probe complexes. In some examples, the nucleic acid probe is at least 30, at least 35, at least 40, at least 45, at least 50, at least 55 or at least 60 nucleotides in length. In specific non-limiting examples, the probe is about 20 to about 60, about 30 to about 55, or about 40 to about 50 nucleotides in length. In particular examples, the capture probe and the reporter probe are each about 50 nucleotides in length. In specific non-limiting examples, the capture probe and reporter probe each hybridize to a portion of a target sequence set forth herein as any one of SEQ ID NOs: 1-21.

Further provided herein are kits that include a probe set disclosed herein, such as a probe set that includes a nucleic acid probe specific for each of ASNS, CDK1, DNASE1L3, FBXL5, GOT2, GRHPR, IARS, LGALS3, LHFPL2, MFGE8, MKI67, PEBP1, TNFSF10, and UBB; for each of ASNS, CDK1, DNASE1L3, FBXL5, GABARAPL3, GOT2, GRHPR, IARS, LGALS3, LHFPL2, MFGE8, MKI67, PEBP1, TNFSF10, and UBB; or for each of ASNS, CDK1, DNASE1L3, FBXL5, GABARAPL3, GOT2, GRHPR, IARS, LGALS3, LHFPL2, MFGE8, MKI67, PEBP1, TNFSF10, UBB, ACTB, B2M, EEF1A1, FTL, GUSB, and LDHA. In some examples, the kit further includes a buffer, such as a hybridization buffer. In some examples, the kit further includes reagents for performing PCR, such as a polymerase, dNTPs, and/or $MgCl_2$.

The present disclosure further provides a device for carrying out the TACE Navigator *Gene* Signature Assay. In some embodiments, the device includes a probe set disclosed herein, such as a probe set that includes a nucleic acid probe specific for each of ASNS, CDK1, DNASE1L3, FBXL5, GOT2, GRHPR, IARS, LGALS3, LHFPL2, MFGE8, MKI67, PEBP1, TNFSF10, and UBB; for each of ASNS, CDK1, DNASE1L3, FBXL5, GABARAPL3, GOT2, GRHPR, IARS, LGALS3, LHFPL2, MFGE8, MKI67, PEBP1, TNFSF10, and UBB; or for each of ASNS, CDK1, DNASE1L3, FBXL5, GABARAPL3, GOT2, GRHPR, IARS, LGALS3, LHFPL2, MFGE8, MKI67, PEBP1, TNFSF10, UBB, ACTB, B2M, EEF1A1, FTL, GUSB, and LDHA.

Further provided herein are methods of detecting expression of a plurality of genes that indicate whether a HCC will respond to TACE by detecting expression of ASNS, CDK1, DNASE1L3, FBXL5, GOT2, GRHPR, IARS, LGALS3, LHFPL2, MFGE8, MKI67, PEBP1, TNFSF10, and UBB in an HCC sample obtained from a subject diagnosed with HCC, relative to a control using a probe set disclosed herein. In some embodiments, the method further includes detecting expression of GABARAPL3 in an HCC sample obtained from a subject diagnosed with HCC, relative to a control using a probe set disclosed herein.

Also provided herein is method of treating a hepatocellular carcinoma (HCC) in a subject. In some embodiments, the method includes determining that the HCC will respond to transarterial chemoembolization (TACE) by detecting a modulation (increase or decrease) in expression of ASNS, CDK1, DNASE1L3, FBXL5, GOT2, GRHPR, IARS, LGALS3, LHFPL2, MFGE8, MKI67, PEBP1, TNFSF10 and UBB relative to a control; and administering TACE to the subject. In some examples, the method further includes detecting a modulation (increase or decrease) in expression of GABARAPL3 relative to a control. In some examples, the subject further receives one or more additional therapies and/or surgery. In some examples, detecting a modulation in expression of the TACE-response genes is carried out by the same party that treats the subject. In other examples, detecting a modulation in expression of the TACE-response genes is performed by a third party, such as a clinical laboratory.

In some embodiments of the methods disclosed herein, the TACE includes one or more of cisplatin, adriamycin, mitomycin and doxorubicin.

IV. TACE Gene Signature

Described herein is the identification of a gene signature for the prediction of HCC responsiveness to TACE. The 14-gene signature includes ASNS, CDK1, DNASE1L3, FBXL5, GOT2, GRHPR, IARS, LGALS3, LHFPL2, MFGE8, MKI67, PEBP1, TNFSF10, and UBB. Correlation analysis of gene expression in subjects who did and did not respond to TACE led to the identification of the 14-gene signature. In some examples, the gene signature is a 15-gene signature that further includes GABARAPL3.

Thus, provided herein is a method, which can be used to predict whether a subject diagnosed with HCC will respond to TACE; to treat a subject diagnosed with HCC (for example with TACE, surgery, or both; or combinations thereof. The method includes detecting expression of the TACE-associated genes ASNS, CDK1, DNASE1L3, FBXL5, GOT2, GRHPR, IARS, LGALS3, LHFPL2, MFGE8, MKI67, PEBP1, TNFSF10, and/or UBB (and optionally GABARAPL3), and comparing expression of the TACE-associated genes in the tumor sample to a control. In one example, the method includes detecting expression of a plurality of HCC-associated genes in a tumor sample obtained from the subject, wherein the plurality of TACE-associated genes consists essentially of or consists of ASNS, CDK1, DNASE1L3, FBXL5, GOT2, GRHPR, IARS, LGALS3, LHFPL2, MFGE8, MKI67, PEBP1, TNFSF10, and UBB. In another example, the plurality of TACE-associated genes consists essentially of or consists of ASNS, CDK1, DNASE1L3, FBXL5, GABARAPL3, GOT2, GRHPR, IARS, LGALS3, LHFPL2, MFGE8, MKI67, PEBP1, TNFSF10, and UBB. In some examples, housekeeping gene expression is also detected, such as 1, 2, 3, 4, 5, 6, 7, 8, 9 or 10 housekeeping genes (such as 1, 2, 3, 4, 5 or 6 of ACTB, B2M, EEF1A1, FTL, GUSB, and LDHA).

In some embodiments of the method, modulation in expression of the 14 TACE-associated genes in the tumor sample relative to the control indicates that the tumor will likely respond to TACE. In particular non-limiting examples, an increase in expression of ASNS, CDK1, FBXL5, IARS, LGALS3, LHFPL2, MKI67, and UBB and a decrease in expression of DNASE1L3, GOT2, GRHPR, MFGE8, PEBP1, and TNFSF10 (and optionally GABARAPL3) relative to the control indicates the tumor will respond to TACE. Thus, in some examples, subjects in whom such expression is detected are treated with TACE, for example alone or in combination with surgery.

In some embodiments, the method further includes converting gene expression values to a z-score. In some examples, the method further includes applying a prognostic index equation to predict whether the HCC will respond to TACE (see FIG. 3A and Examples 1 and 2).

Expression of the TACE-associated genes (and housekeeping genes) can be detected using any suitable means known in the art. For example, detection of gene expression can be accomplished using RT-PCR, array, or nCounter® analysis. Additional methods of detecting gene expression are well known in the art and are described in greater detail below.

The altered expression of the TACE-associated genes can be any measurable increase or decrease in expression that is correlated with likely responsiveness to TACE. In some embodiments, the increase or decrease in expression is about 1.5-fold, about 2-fold, about 2.5-fold, about 3-fold, about 4-fold, about 5-fold, about 7-fold or about 10-fold. The relative increase or decrease in expression level amongst the TACE-associated genes can vary within a tumor and can also vary between tumor samples.

In an alternative embodiment, responsiveness of the HCC to TACE is determined or predicted by detecting DNA copy number of the disclosed 14 TACE-associated genes in an HCC sample. For example, genomic DNA can be amplified, such as by PCR, to detect the presence or absence of gene deletions of one or more of ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3). A change (e.g., increase or decrease) in DNA copy number of ASNS, CDK1, DNASE1L3, FBXL5, GABARAPL3, GOT2, GRHPR, IARS, LGALS3, LHFPL2, MFGE8, MKI67, PEBP1, TNFSF10, and UBB (and optionally GABARAPL3) in a HCC sample, relative to a control, indicates the HCC will likely respond to TACE.

The control can be any suitable control against which to compare expression of a TACE-associated gene in a tumor sample. In some embodiments, the control sample is non-tumor tissue. In some examples, the non-tumor tissue is obtained from the same subject, such as non-tumor liver tissue that is adjacent to the HCC tumor. In other examples, the non-tumor tissue is obtained from a healthy control subject (such as a subject who has not had and does not have cancer). In some embodiments, the control is a reference value. For example, the reference value can be derived from the average expression values obtained from a group of healthy control subjects or non-tumor tissue from a group of HCC patients.

The methods described herein can be used to predict the responsiveness of a HCC patient to TACE with any type of disease etiology. In some embodiments, the subject diagnosed with HCC has a chronic viral infection. In one example, the chronic infection is a HBV infection. In another example, the chronic infection is a HCV infection. In other embodiments, the subject diagnosed with HCC has cirrhosis of the liver. In one example, cirrhosis of the liver is caused by chronic alcohol consumption. In another example, cirrhosis of the liver is caused by inherited hemochromatosis. In another example, cirrhosis of the liver is caused by exposure to aflatoxin, such as by ingestion of aflatoxin-contaminated food.

A. Detecting Expression of TACE-Associated Genes

As described below, expression of the 14 TACE-associated genes (or in some cases,) 15 TACE-associated genes) can be detected using any one of a number of methods. Expression of either mRNA or protein is contemplated herein.

1. Methods for Detection of mRNA

Gene expression can be evaluated by detecting mRNA encoding the gene of interest. Thus, the disclosed methods can include evaluating mRNA encoding ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3), and in some examples also ACTB, B2M, EEF1A1, FTL, GUSB, and LDHA. In some examples, the mRNA is quantified.

RNA can be isolated from a sample of an HCC tumor from a subject, a sample of adjacent non-tumor tissue from the subject, from tumor-free tissue from a normal (healthy) subject, or combinations thereof, using methods well known to one skilled in the art, including commercially available kits. General methods for mRNA extraction are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., *BioTechniques* 18:42044 (1995). In one example, RNA isolation can be performed using a purification kit, buffer set and protease from commercial manufacturers, such as QIAGEN®, according to the manufacturer's instructions. For example, total RNA from cells in culture (such as those obtained from a subject) can be isolated using QIAGIN® RNeasy mini-columns. Other commercially available RNA isolation kits include MASTERPURE®. Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared from tumor or other biological sample can be isolated, for example, by cesium chloride density gradient centrifugation.

Methods of gene expression profiling include methods based on hybridization analysis of polynucleotides, methods based on sequencing of polynucleotides, and proteomics-based methods. In some examples, mRNA expression in a sample is quantified using northern blotting or in situ hybridization (Parker & Barnes, *Methods in Molecular Biology* 106:247-283, 1999); RNAse protection assays (Hod, *Biotechniques* 13:852-4, 1992); and PCR-based methods, such as reverse transcription polymerase chain reaction (RT-PCR) (Weis et al., *Trends in Genetics* 8:263-4, 1992). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). In one example, RT-PCR can be used to compare mRNA levels in different samples, in normal and tumor tissues, with or without drug treatment, to characterize patterns of gene expression, to discriminate between closely related mRNAs, and to analyze RNA structure.

Methods for quantifying mRNA are well known in the art. In some examples, the method utilizes RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV- RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase. TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

To minimize errors and the effect of sample-to-sample variation, RT-PCR can be performed using an internal standard. The ideal internal standard is expressed at a constant level among different tissues, and is unaffected by the experimental treatment. RNAs commonly used to normalize patterns of gene expression are mRNAs for the housekeeping genes glyceraldehyde-3-phosphate-dehydrogenase (GAPDH), beta-actin, and 18S ribosomal RNA.

A variation of RT-PCR is real time quantitative RT-PCR, which measures PCR product accumulation through a dual-labeled fluorogenic probe (e.g., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Held et al., *Genome Research* 6:986 994, 1996). Quantitative PCR is also described in U.S. Pat. No. 5,538,848. Related probes and quantitative amplification procedures are described in U.S. Pat. Nos. 5,716,784 and 5,723,591. Instruments for carrying out quantitative PCR in microtiter plates are available from PE Applied Biosystems, 850 Lincoln Centre Drive, Foster City, Calif. 94404 under the trademark ABI PRISM® 7700.

The steps of a representative protocol for quantifying gene expression using fixed, paraffin-embedded tissues as the RNA source, including mRNA isolation, purification, primer extension and amplification are given in various publications (see Godfrey et al., *J. Mol. Diag.* 2:84 91, 2000; Specht et al., *Am. J. Pathol.* 158:419-29, 2001). Briefly, a representative process starts with cutting about 10 µm thick sections of paraffin-embedded tumor tissue samples or adjacent non-cancerous tissue. The RNA is then extracted, and protein and DNA are removed. Alternatively, RNA is located directly from a tumor sample or other tissue sample. After analysis of the RNA concentration, RNA repair and/or amplification steps can be included, if necessary, and RNA is reverse transcribed using gene specific promoters followed by RT-PCR. The primers used for the amplification are selected so as to amplify a unique segment of the gene of interest, such as mRNA encoding ASNS, CDK1, DNASE1L3, FBXL5, GABARAPL3, GOT2, GRHPR, IARS, LGALS3, LHFPL2, MFGE8, MKI67, PEBP1, TNFSF10, or UBB. In some embodiments, expression of other genes is also detected. Primers that can be used to amplify ASNS, CDK1, DNASE1L3, FBXL5, GABARAPL3, GOT2, GRHPR, IARS, LGALS3, LHFPL2, MFGE8, MKI67, PEBP1, TNFSF10, or UBB are commercially available or can be designed and synthesized.

An alternative quantitative nucleic acid amplification procedure is described in U.S. Pat. No. 5,219,727. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some embodiments of this method, the expression of a "housekeeping" gene or "internal control" can also be evaluated. These terms include any constitutively or globally expressed gene whose presence enables an assessment of HCC-associated gene mRNA levels. Such an assessment includes a determination of the overall constitutive level of gene transcription and a control for variations in RNA recovery. Exemplary housekeeping genes include ACTB, B2M, EEF1A1, FTL, GUSB, and LDHA.

In some examples, gene expression is identified or confirmed using the microarray technique. Thus, the expression profile can be measured in either fresh or paraffin-embedded tumor tissue, using microarray technology. In this method, TACE-associated gene nucleic acid sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors, and optionally from corresponding noncancerous tissue and normal tissues or cell lines.

In a specific embodiment of the microarray technique, PCR amplified inserts of cDNA clones are applied to a substrate in a dense array. At least probes specific for ASNS, CDK1, DNASE1L3, FBXL5, GOT2, GRHPR, IARS, LGALS3, LHFPL2, MFGE8, MKI67, PEBP1, TNFSF10, and UBB (and in some examples also GABARAPL3 and/or the housekeeping genes ACTB, B2M, EEF1A1, FTL, GUSB, and LDHA) nucleotide sequences are applied to the substrate, and the array can consist essentially of, or consist of these sequences. The microarrayed nucleic acids are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3). Microarray analysis can be performed by commercially available equipment, following manufacturer's protocols.

Serial analysis of gene expression (SAGE) allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-7, 1995; and Velculescu et al., *Cell* 88:243-51, 1997, herein incorporated by reference).

In situ hybridization (ISH) is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of TACE-associated genes.

Sample cells or tissues are treated to increase their permeability to allow a probe, such as a TACE-associated gene-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a non-cancerous, or HCC tumor sample. Since the sequences of the TACE-associated genes of interest are known, probes can be designed accordingly such that the probes specifically bind the gene of interest.

In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products can be achieved by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

Gene expression can also be detected and quantitated using the nCounter® technology developed by NanoString (Seattle, Wash.; see, for example, U.S. Pat. Nos. 7,473,767; 7,919,237; and 9,371,563, which are herein incorporated by reference in their entirety). The nCounter® analysis system utilizes a digital color-coded barcode technology that is based on direct multiplexed measurement of gene expression. The technology uses molecular "barcodes" and single molecule imaging to detect and count hundreds of unique transcripts in a single reaction. Each color-coded barcode is attached to a single target-specific probe corresponding to a gene of interest (such as a TACE-response gene). Mixed together with controls, they form a multiplexed CodeSet.

Each color-coded barcode represents a single target molecule. Barcodes hybridize directly to target molecules and can be individually counted without the need for amplification. The method includes three steps: (1) hybridization; (2) purification and immobilization; and (3) counting. The technology employs two approximately 50 base probes per mRNA that hybridize in solution. The reporter probe carries the signal; the capture probe allows the complex to be immobilized for data collection. After hybridization, the excess probes are removed and the probe/target complexes are aligned and immobilized in the nCounter® cartridge. Sample cartridges are placed in the digital analyzer for data collection. Color codes on the surface of the cartridge are counted and tabulated for each target molecule. This method is described in, for example, U.S. Pat. No. 7,919,237; and U.S. Patent Application Publication Nos. 20100015607; 20100112710; 20130017971, which are herein incorporated by reference in their entirety. Information on this technology can also be found on the company's website (nanostring.com).

2. Arrays for Profiling Tumor-Associated Gene Expression

In particular embodiments provided herein, arrays are provided that can be used to evaluate gene expression, for example to determine if a patient with HCC will respond to TACE. When describing an array that consists essentially of probes or primers specific for ASNS, CDK1, DNASE1L3, FBXL5, GOT2, GRHPR, IARS, LGALS3, LHFPL2, MFGE8, MKI67, PEBP1, TNFSF10, and UBB, such an array includes probes or primers specific for these 14 TACE-associated genes, and can further include control probes (for example to confirm the incubation conditions are sufficient). In some examples, the array may further include probes or primers specific for GABARAPL3. In some examples, the array may further comprise additional, such as 1, 2, 3, 4 or 5 additional tumor-associated genes. In other examples, the array may include fewer, such as 1, 2, 3, 4 or 5 fewer tumor-associated genes. In some examples, the array includes 1-10 housekeeping-specific probes or primers (such as those specific for ACTB, B2M, EEF1A1, FTL, GUSB, and LDHA. In one example, an array is a multi-well plate (e.g., 98 or 364 well plate).

In one example, the array includes, consists essentially of, or consists of probes or primers (such as an oligonucleotide or antibody) that can recognize ASNS, CDK1, DNASE1L3, FBXL5, GABARAPL3, GOT2, GRHPR, IARS, LGALS3, LHFPL2, MFGE8, MKI67, PEBP1, TNFSF10, and UBB (and in some examples also ACTB, B2M, EEF1A1, FTL, GUSB, and LDHA). In another example, the array includes, consists essentially of, or consists of probes or primers (such as an oligonucleotide or antibody) that can recognize ASNS, CDK1, DNASE1L3, FBXL5, GOT2, GRHPR, IARS, LGALS3, LHFPL2, MFGE8, MKI67, PEBP1, TNFSF10, and UBB (and in some examples also ACTB, B2M, EEF1A1, FTL, GUSB, and LDHA). The oligonucleotide probes or primers can further include one or more detectable labels, to permit detection of hybridization signals between the probe and target sequence (such as the 14 or 15 TACE-associated genes disclosed herein).

a. Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluoride, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567).

In one example, the solid support surface is polypropylene. In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

b. Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use. In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit a low background fluorescence.

The array formats of the present disclosure can be included in a variety of different types of formats. A "format" includes any format to which the solid support can be affixed, such as microtiter plates (e.g., multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant.

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known; a summary of suitable methods can be found in Matson et al., Anal. Biochem. 217:306-10, 1994. In one example, the oligonucleotides are synthesized onto the support using chemical techniques for preparing oligonucleotides on solid supports (such as see PCT applications WO 85/01051 and WO 89/10977, or U.S. Pat. No. 5,554,501).

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

3. Methods for Detection of Protein

In some examples, expression of ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3) proteins is analyzed. Suitable biological samples include samples containing protein obtained from an HCC of a subject, non-tumor tissue from the subject, and/or protein obtained from one or more samples of cancer-free subjects. An alteration in the amount of ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3) proteins in a tumor from the subject relative to a control, such as an increase or decrease in expression, indicates whether the HCC will respond to TACE, as described above.

Antibodies specific for ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3) proteins can be used for detection and quantification of TACE-associated proteins by one of a number of immunoassay methods that known in the art, such as those presented in Harlow and Lane (Antibodies, A Laboratory Manual, CSHL, New York, 1988). Methods of constructing such antibodies are known in the art.

Any standard immunoassay format (such as ELISA, Western blot, or RIA assay) can be used to measure protein levels. Thus, ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3) polypeptide levels in an HCC sample can readily be evaluated using these methods. Immunohistochemical techniques can also be utilized for tumor-associated gene detection and quantification. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantifying tumor-associated proteins, a biological sample of the subject that includes cellular proteins can be used. Quantification of ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3) protein can be achieved by immunoassay methods known in the art. The amount ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3) protein can be assessed in the tumor and optionally in the adjacent non-tumor tissue or in liver tissue from cancer-free subjects. The amounts of ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3) protein in the tumor can be compared to levels of the protein found in cells from a cancer-free subject or other control (such as a standard value or reference value). A significant increase or decrease in the amount can be evaluated using statistical methods disclosed herein and/or known in the art.

Quantitative spectroscopic approaches, such as SELDI, can be used to analyze ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3) expression in a sample (such as non-cancerous tissue, tumor tissue, and tissue from a cancer-free subject). In one example, surface-enhanced laser desorption-ionization time-of-flight (SELDI-TOF) mass spectrometry is used to detect protein expression, for example by using the ProteinChip™ (Ciphergen Biosystems, Palo Alto, Calif.). Such methods are well known in the art (for example see U.S. Pat. Nos. 5,719,060; 6,897,072; and 6,881,586). SELDI is a solid phase method for desorption in which the analyte is presented to the energy stream on a surface that enhances analyte capture or desorption.

The surface chemistry allows the bound analytes to be retained and unbound materials to be washed away. Subsequently, analytes bound to the surface (such as tumor-associated proteins) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection means can be implemented in series to fully interrogate the analyte components and function associated with retained molecules at each location in the array.

Therefore, in a particular example, the chromatographic surface includes antibodies that specifically bind ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3). In other examples, the chromatographic surface consists essentially of, or consists of, antibodies that specifically bind ASNS, CDK1, DNASE1L3, FBXL5, GOT2, GRHPR, IARS, LGALS3, LHFPL2, MFGE8, MKI67, PEBP1, TNFSF10, and UBB (and optionally GABARAPL3). In some examples, the chromatographic surface includes antibodies that bind other molecules, such as housekeeping proteins (e.g. ACTB, B2M, EEF1A1, FTL, GUSB, and LDHA).

In another example, antibodies are immobilized onto the surface using a bacterial Fc binding support. The chromatographic surface is incubated with a sample, such as a sample of a HCC tumor. The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

4. Method of Detecting Gene Deletions

Methods of detecting the presence or absence of a gene deletion are known in the art. For example, genomic DNA can be isolated from a subject, such as from a tumor sample or adjacent non-tumor sample and subjected to amplification by PCR using primers specific for genomic sequences of interest. In particular examples, the PCR primers are designed to amplify genomic regions corresponding to one or more TACE-associated genes, such as ASNS, CDK1, DNASE1L3, FBXL5, GABARAPL3, GOT2, GRHPR, IARS, LGALS3, LHFPL2, MFGE8, MKI67, PEBP1, TNFSF10, and/or UBB. Alternatively, DNA copy number can be assessed using a genomic array-based method.

B. Tumor and Non-Tumor Tissue Samples

The methods provided herein include detecting expression of the 15-TACE-associated genes in HCC and non-tumor tissue samples. In some embodiments, the tissue samples are obtained from subjects diagnosed with HCC and, in some cases, from healthy subjects or cadaveric donors. A "sample" refers to part of a tissue that is either the entire tissue, or a diseased or healthy portion of the tissue. As described herein, tumor tissue samples are compared to a control. In some embodiments, the control is non-tumor tissue sample obtained from the same subject, such as non-cancerous liver tissue surrounding the tumor. In other embodiments, the control is a standard or reference value based on an average of historical values. In some examples, the reference value is an average expression value in HCC obtained from a group of HCC patients who did or did not respond to TACE.

Tissue samples can be obtained from a subject using any method known in the art. For example, tissue samples can be obtained from HCC patients who have undergone tumor resection as a form of treatment. From these patients, both tumor tissue and surrounding non-cancerous colon tissue can be obtained. In some embodiments, the non-tumor tissue sample used as a control is obtained from a cadaver. In other embodiments, the non-cancerous tissue sample is obtained from a healthy liver donor (see Kim et al., *Hepatology* 39(2):518-527, 2004).

In some embodiments, tissue samples are obtained by biopsy. Biopsy samples can be fresh, frozen or fixed, such as formalin-fixed and paraffin embedded. Samples can be removed from a patient surgically, by extraction (for example by hypodermic or other types of needles), by microdissection, by laser capture, or by any other means known in the art.

C. Treatment

HCCs identified as those likely to respond to TACE, can receive TACE treatment. Thus, the disclosed methods can include administration of TACE therapy. Treatment of HCC can include reducing signs or symptoms associated with the presence of such a tumor (for example by reducing the size or volume of the tumor or a metastasis thereof). Such reduced growth can in some examples decrease or slow metastasis of the tumor, or reduce the size or volume of the tumor by at least 10%, at least 20%, at least 40%, at least 50%, at least 75%, or at least 90%. In some examples, the methods include measuring the size and/or volume of a tumor (such as before and after TACE). In some examples, the subject receives additional therapy, such as surgical resection of the tumor.

TACE procedures have been described (see, for example, Van Ha, *Semin Intervent Radiol* 26(3):270-275, 2009). TACE is a percutaneous technique, usually through the common femoral arterial approach, making use of fluoroscopic guidance and coaxial catheter system to deliver a local and concentrated dose of chemotherapeutic agents directly into the arterial feeding vessels of the tumor in conjunction with or followed by embolization using either permanent or temporary particulate materials. Though techniques can vary, the principles of TACE are consistent: to deliver a higher drug concentration into the tumor than possible by systemic therapy and prolonging drug dwell time within the tumor by reducing washout. Most of the drug is retained within the tumor, therefore another benefit of TACE is the reduction of systemic drug toxicity. TACE exploits the predominant hepatic arterial supply to HCC, with occasional parasitic siphoning from other arterial territories depending on tumor location such as the intercostal, lumbar, inferior phrenic, or internal mammary arteries. The normal liver parenchyma is supplied mostly by the portal vein and a much smaller percentage by the hepatic artery.

Typically, at the time of the TACE procedure, a routine abdominal aortogram is performed. This delineates visceral anatomy and can identify tumor parasitization from intercostal, phrenic, or lumbar arteries. The superior mesenteric artery (SMA) is then selected with a catheter and an arteriogram is performed with large contrast volume to assess for variant anatomy, unconventional feeding arteries to tumors, and in the venous phase, to assess for portal vein patency and flow. Next, the celiac artery is selected and a selective arteriogram is performed to look for arterial supply to the tumors and also to identify vessels that should not be embolized such as vessels to the gallbladder, stomach, and intestines. Vessels to the stomach or intestines should not be chemoembolized and may rarely need to be coil embolized prior to chemoembolization if they are at risk for reflux. Once the arterial feeding vessels to the tumor(s) are identified, they are super-selected for chemoembolization. Usually, due to small size of the tumor vessels, a microcatheter is used in a coaxial fashion. If super-selection is possible, the vessels are chemoembolized to stasis. Chemoembolization can be performed with ethiodol mixed with chemotherapeutic agents followed by embolization, with Gelfoam® (Pfizer Pharmaceuticals, New York, N.Y.) or polyvinyl alcohol (PVA) particles (Boston Scientific, Natick, Mass.). Alternatively, TACE can be performed using drug-eluting beads. If there is more than one feeding vessel, the dose is divided among feeder vessels using subjective approximation to the volume of tumor fed by each vessel during arteriogram. The same is used when there are multiple lesions. Unless tumor burden is large, there is usually enough chemo-agents to achieve near stasis or decreased flow, and stasis is achieved with Gelfoam® or particles. When using drug-eluting beads, larger tumor burden usually requires two vials of the beads instead of the usual one.

In some cases, a modified conventional TACE protocol using three chemotherapeutic agents in addition to drug-eluting beads is used. In other instances, TACE is carried out using drug-eluting beads with doxorubicin only. Exemplary preparations are listed below:

1. Conventional TACE (Triple Agent or Cisplatin, Adriamycin, and Mitomycin [CAM] Protocol)
   50 to 100 mg doxorubicin (Pharmacia & Upjohn, Kalamazoo, Mich.)
   50 mg cisplatin powder (Bristol Myers Squibb, Princeton, N.J.)
   10 mg mitomycin (Bedford Laboratories, Bedford, Ohio)
   These three drugs are reconstituted with a total of 10 mL of water soluble contrast material (Omnipaque 300; Winthrop Pharmaceuticals, New York, N.Y.). Prior to intraarterial administration, emulsify in 10 cc of iodized oil (Ethiodol; Savage Laboratories, Melville, N.Y.) for a total of volume of 20 cc. Additional particle or gel foam embolization can be used at the end to achieve stasis in tumor vessels.

2. Drug-Eluting Beads
   Two types of drug eluting beads are commercially available. They are used in conjunction with doxorubicin. For doxorubicin-loaded beads, the tumor vessels are selected and the drug-loaded beads are administered. Larger tumors may require more embolic (more than one vial). In cases where stasis is not achieved with the drug-loaded beads, PVA particles can be used to achieve stasis. With the triple CAM regimen, in addition to the doxorubicin-loaded beads, another syringe containing cisplatin and mitomycin is prepared and emulsified with iodized oil prior to intraarterial administration. Typically, the iodized oil preparation is used first until there is visible uptake of the oil and slowing of the flow in the feeder vessels. Then the doxorubicin loaded beads are infused until there is stasis. If there is no stasis after all the doxorubicin-loaded beads are used, then PVA particles are used to achieve stasis.

3. Quadrasphere® Microspheres (100 to 150 microns; Biosphere Medical, Rockland, Mass.)
   Single Agent: 50 to 100 mg of doxorubicin in 1 to 2 vials LC beads or Quadraspheres®. Mix with 10 cc of normal saline and set aside for at least one hour. When ready for intraarterial administration, decant and discard supernatant. Mix in equal amount of iso-osmolar nonionic contrast with bead solution.
   Triple Agent (CAM):
   Optional: 50 mg cisplatin and 10 mg mitomycin in 5 mL ethiodol
   Syringe 1: Reconstitute 50 mg doxorubicin with 10 cc normal saline. Mix well to obtain clear solution. Add the reconstituted doxorubicin to 1 to 2 vials of Quadraspheres®. Let sit for at least one hour. Draw out content and put into 10 cc syringe. Prior to intraarterial administration, decant and discard supernatant (~5 to 6 cc) and mix the remaining solution with 5 mL Visipaque™ (GE Healthcare, Chalfont St. Giles, UK).
   Syringe 2: Prepare cisplatin and mitomycin. Add 5 cc of normal saline to 10 mg vial of mitomycin. Agitate to mix solution. Withdraw entire content and add to 50 mg vial of cisplatin powder. Agitate to mix solution. Place the 5 cc solution in a 10 cc syringe. Prior to administration intraarterially, mix with 5 cc ethiodol.

4. LC Beads (300 to 500 microns; Angiodynamics, Queensbury, N.Y.)

Allow the vial of beads to stand and the beads will settle to the bottom. Aspirate as much of the saline as possible and discard. Reconstitute a vial of 50 mg doxorubicin powder with 2 cc sterile water and add to LC beads. The beads will turn from blue to red. Allow at least 30 minutes for the beads to adsorb the doxorubicin. Prior to use, get rid of as much supernatant as possible and add the same volume as the remaining bead solution of iso-osmolar nonionic contrast. For triple agent use, prepare another syringe with cisplatin and mitomycin as above.

V. Probes and Kits

Provided herein is a TACE Navigator Gene Signature Assay, which includes probe sets that include probes specific for each of the 14 TACE signature genes (and in some examples, 15 TACE signature genes) and 6 housekeeping control genes. In some embodiments, the probe set includes a nucleic acid probe specific for each of ASNS, CDK1, DNASE1L3, FBXL5, GOT2, GRHPR, IARS, LGALS3, LHFPL2, MFGE8, MKI67, PEBP1, TNFSF10, and UBB. In other embodiments, the probe set includes a nucleic acid probe specific for each of ASNS, CDK1, DNASE1L3, FBXL5, GABARAPL3, GOT2, GRHPR, IARS, LGALS3, LHFPL2, MFGE8, MKI67, PEBP1, TNFSF10, and UBB. In some examples, the probe set further includes nucleic acid probes specific for at least 1, 2, 3, 4, 5, 6, 7, 8, 9 or 10, such as about 1 to about 10, or about 1 to about 6, housekeeping genes. In specific non-limiting examples, the housekeeping genes include 1, 2, 3, 4, 5 or 6 of ACTB, B2M, EEF1A1, FTL, GUSB and LDHA. In one specific example, the probe set includes a nucleic acid probe specific for each of ASNS, CDK1, DNASE1L3, FBXL5, GOT2, GRHPR, IARS, LGALS3, LHFPL2, MFGE8, MKI67, PEBP1, TNFSF10, UBB, ACTB, B2M, EEF1A1, FTL, GUSB, and LDHA. In another specific example, the probe set includes a nucleic acid probe specific for each of ASNS, CDK1, DNASE1L3, FBXL5, GABARAPL3, GOT2, GRHPR, IARS, LGALS3, LHFPL2, MFGE8, MKI67, PEBP1, TNFSF10, UBB, ACTB, B2M, EEF1A1, FTL, GUSB, and LDHA.

In some examples, the probes are ones that can be used with the nCounter® Analysis System from NanoString Technologies (Seattle, Wash.). For example, the probes can include a capture probe and a reporter probe, wherein the reporter probe comprises one or more detectable labels. In some examples, the capture probe includes a molecule that allows immobilization of target:probe complexes. In some examples, the nucleic acid probe is at least 30, at least 35, at least 40, at least 45, at least 50, at least 55 or at least 60 nucleotides in length. In specific non-limiting examples, the probe is about 20 to about 60, about 30 to about 55, or about 40 to about 50 nucleotides in length. In particular examples, the capture probe and the reporter probe are each about 50 nucleotides in length. In specific non-limiting examples, the capture probe and reporter probe each hybridize to a portion of a target sequence set forth herein as any one of SEQ ID NOs: 1-21.

Further provided herein are kits that include a probe set disclosed herein, such as a probe set that includes a nucleic acid probe specific for each of ASNS, CDK1, DNASE1L3, FBXL5, GOT2, GRHPR, IARS, LGALS3, LHFPL2, MFGE8, MKI67, PEBP1, TNFSF10, and UBB; for each of ASNS, CDK1, DNASE1L3, FBXL5, GABARAPL3, GOT2, GRHPR, IARS, LGALS3, LHFPL2, MFGE8, MKI67, PEBP1, TNFSF10, and UBB; or for each of ASNS, CDK1, DNASE1L3, FBXL5, GABARAPL3, GOT2, GRHPR, IARS, LGALS3, LHFPL2, MFGE8, MKI67, PEBP1, TNFSF10, UBB, ACTB, B2M, EEF1A1, FTL, GUSB, and LDHA. In some examples, the kit further includes a buffer, such as a hybridization buffer.

The present disclosure further provides a device for carrying out the TACE Navigator Gene Signature Assay. In some embodiments, the device includes a probe set disclosed herein, such as a probe set that includes a nucleic acid probe specific for each of ASNS, CDK1, DNASE1L3, FBXL5, GOT2, GRHPR, IARS, LGALS3, LHFPL2, MFGE8, MKI67, PEBP1, TNFSF10, and UBB; for each of ASNS, CDK1, DNASE1L3, FBXL5, GABARAPL3, GOT2, GRHPR, IARS, LGALS3, LHFPL2, MFGE8, MKI67, PEBP1, TNFSF10, and UBB; or for each of ASNS, CDK1, DNASE1L3, FBXL5, GABARAPL3, GOT2, GRHPR, IARS, LGALS3, LHFPL2, MFGE8, MKI67, PEBP1, TNFSF10, UBB, ACTB, B2M, EEF1A1, FTL, GUSB, and LDHA.

The following examples are provided to illustrate certain particular features and/or embodiments. These examples should not be construed to limit the disclosure to the particular features or embodiments described.

EXAMPLES

Example 1: Materials and Methods

This example describes the materials and experimental methods used for the studies described in Example 2.

Clinical Specimens

A previously-described cohort, the LCI Cohort, in which gene expression had been measured by AFFYMETRIX™ platform (NCBI GEO accession number GSE14520), was retrospectively analyzed. This cohort consisted of treatment-naïve, snap-frozen tumor tissue from 247 patients who underwent radical resection at the Liver Cancer Institute of Fudan University (Roessler et al., *Cancer Res* 70:10202-10212, 2010). Of these 247 patients, 105 received TACE as part of their therapy, either as adjuvant therapy or post-relapse; 52 received other forms of adjuvant therapy, not including TACE; and 90 received no additional therapy. Bioinformatic analyses, including class comparison and survival risk prediction algorithms, were used to identify genes that were predictive of overall survival, independent of other clinical variables, in the group of 105 patients receiving TACE, but not in other patients who received other adjuvant therapies (n=52) or no adjuvant therapy (n=90).

A custom nCounter Gene Expression CodeSet was developed that consisted of a 15-gene TACE signature and 6 control genes, which was re-evaluated in 93 TACE patients from the LCI Cohort using the NANOSTRING™ platform. A prognostic index equation prediction module was then developed based on the expression of each signature gene, which was referred to as the TACE Navigator gene signature. The validation cohort, the Hong Kong Cohort, consisted of formalin fixed, paraffin embedded tumor samples that were obtained from 49 patients with HCC who underwent radical resection at the University of Hong Kong Medical Centre in Hong Kong, and then received adjuvant TACE as part of their treatment. All patients were coded before NANOSTRING™ was performed, and the expression of each TACE Navigator signature gene was measured by NANOSTRING™. At the completion of data collection, patients were subsequently decoded and clinical data for each patient was obtained. The ability of the prognostic index equation to assign patients into groups with differential overall survival was evaluated.

Bioinformatic Analyses

Microarray profiling of gene expression of flash-frozen tumor tissue previously profiled using AFFYMETRIX™ Human Genome U133 2.0 microarray platform was previously described (Roessler et al., Cancer Res 70:10202-10212, 2010). The BRB-ArrayTools software 4.5.0 was used for all bioinformatics analyses. When examining most variable genes, a most variable gene filter was used that excluded genes with: less than 20% of expression data values having a least a 2-fold change in either direction from the gene's median value; a log intensity variation with a p-value >0.01; and percent missing data exceeding 50%. Of 13,101 global genes, 1,292 genes passed the most variable filter. Hierarchical clustering was performed with centered correlation and average linkage. Genes were centered for the analysis. For principal component analysis, the three principal components were calculated from global gene expression of tumor samples by the prcomp( ) function in stats package in R version 3.2.3. 3D PCA scatter plot was generated by Plotly R API (Plotly Technologies Inc., Montreal, QC). Global class comparison was performed using multivariate permutations tests with 1000 permutations, and a maximum proportion of false discoveries of 0.1 at a 90% confidence level. Survival risk prediction was performed using 2-risk groups with a prognostic index percentile of 50%. Cross validation was performed using 10-fold cross validation, and 1000 permutations based on log rank statistic were performed. Gene lists were determined using 2 principal components.

To analyze gene networks, differentially expressed genes between TACE Responders and Non-Responders were determined using global class comparison as described above. All differentially expressed genes were input into Gene Set Enrichment Analysis (Broad Institute, Cambridge, Mass.). Overlaps were computed using the Hallmark gene sets. All differentially expressed genes and fold-changes were also uploaded into Ingenuity Pathway Analysis (Qiagen), and a core analysis was performed. The results of the Upstream Analysis were examined Hong Kong Cohort RNA Isolation Patient samples were formalin fixed and paraffin embedded. The presence of tumor vs. non-tumor tissue was verified by H&E staining, and tumor tissue was collected by scraping five 5 μm tumor sections for each patient. Total RNA was isolated using the High Pure FFPET RNA Isolation Kit (Roche, Indianapolis, Ind.) according to the manufacturer's instructions. RNA concentration was measured using NANODROP™ (ThermoFisher Scientific, Waltham, Mass.), and RNA quality was evaluated using a 2100 Bioanalyzer and RNA 6000 Nano Kit according to the manufacturer's instructions (Agilent, Santa Clara, Calif.).

NANOSTRING™ Analysis

A custom nCounter Gene Expression CodeSet was manufactured by NanoString Technologies (Seattle, Wash.), which contained the 15 chosen signature genes and 6 additional housekeeping genes. Probes for each gene were designed by NANOSTRING™. Housekeeping genes were chosen from a list of 54 suggested housekeeping genes from NANOSTRING™ plus 49 genes from the LCI patient cohort with median Log 2 intensity of >12. Genes were evaluated using 488 tumor and non-tumor samples from the LCI cohort, and were narrowed down using the following criteria: housekeeping genes must have little change in expression between tumor and non-tumor tissue (0.85≤Fold Change≤1.15); a median Log 2 intensity >8; and <7.5% of samples outside Tukey variation (within 1.5 interquartile range of the lower or upper quartile). A total of five genes met the criteria, and were chosen as housekeeping genes (FTL, EEF1A1, GUSB, B2M, LDHA). In addition, a "classic" housekeeping gene, ACTB, was added, which met all criteria except fold change between tumor and non-tumor (fold change=1.28). All housekeeping genes were verified in an independent cohort of HCC patients, with a total of 121 tumor and non/tumor samples. All housekeeping genes met all criteria in the independent cohort.

The protocol for preparing samples with the nCounter CodeSet was according to instructions provided by NANOSTRING™. Each final hybridization reaction contained 100 ng of RNA from each patient sample in 5 μL of water, 10 μL Reporter CodeSet, 10 μL hybridization buffer, and 5 μL Capture ProbeSet, for a total volume of 30 μL. Hybridization reactions were incubated for at least 12 hours (but no more than 30 hours) at 65° C. Reactions were kept at 65° C. until analysis. NANOSTRING™ Digital Gene Expression Analysis was then performed. In total, gene expression was measured in 93 TACE patients from the LCI Cohort in order to ensure that gene expression as measured by AFFYMETRIX™ chip or NANOSTRING™ were correlated. Gene expression was then measured by NANOSTRING™ in 49 patients from the Hong Kong Cohort for validation.

Gene expression was analyzed using nSolver Analysis Software 2.5, provided by NANOSTRING™. Background correction was performed by subtracting the maximum count value of 8 negative control probes included in the CodeSet. The data was then normalized by using the geometric mean of 6 positive control probes included in the CodeSet to compute a normalization factor. Samples were flagged if the normalization factor was outside the 0.3-3 range. The data was also normalized using the geometric mean of the 6 housekeeping genes to compute a normalization factor. Samples were flagged if the normalization factor was outside the 0.1-10 range. All default quality control (QC) measures provided by the nSolver software were used for each sample. All samples included in subsequent analyses passed all QC measures. Following background subtraction and normalization, the count values measured were log 2 transformed and then data was exported.

Prognostic Index Equation

The Log 2 expression of all signature genes as measured by AFFYMETRIX™ chip and NANOSTRING™ were evaluated in LCI cohort patients, and correlation was examined. The expression of all genes as measured by either method was statistically significantly correlated in all but one gene, GABARAPL3. This gene was subsequently removed from the gene signature for further analysis due to lack of correlation. Log 2 expression scores were then Z-score corrected within each cohort, and the corrected expression of each gene was compared between each cohort. No statistically significant differences in Z-score-corrected expression were noted for any gene.

Z-score corrected data for the LCI Cohort was imported into BRB-ArrayTools. To create a prognostic index equation, survival risk prediction was performed in the LCI Cohort of patients using 2-risk groups with a prognostic index percentile of 50%. Cross validation was performed using 10-fold cross validation, and 1000 permutations based on log rank statistic were performed. The significance threshold of the Cox Model was set to 0.999 to ensure that all signature genes were included in the model. The analysis yielded gene weights and a simple formula to compute prognostic index using gene weights and gene expression, output by BRB-ArrayTools. A prognostic index threshold for determining if a new sample would be predicted to be high risk (worse overall survival) or low risk (better overall survival) was also determined by the analysis. This equation was then used to predict whether patients in the Hong Kong Cohort would be likely to have better or worse overall survival based on gene expression.

Statistical Analysis

In all statistical analyses for this study, $p<0.05$ was considered statistically significant. Clinical data was evaluated using chi-square test, Fisher's exact test, ordinary one-way ANOVA, or 2-tailed Student's t-test. Patient survival was evaluated using Kaplan-Meier survival analysis with log-rank test. Correlation comparing AFFYMETRIX™ gene expression and NANOSTRING™ gene expression was evaluated using Pearson correlation, and Z-score corrected gene expression for each signature gene was compared between the LCI and Hong Kong Cohorts using non-parametric Mann-Whitney test. All statistics were calculated using GraphPad Prism 6.0 (GraphPad, San Diego, Calif.).

Univariable and multivariable analyses were performed with Cox proportional hazards regression analysis using STATA 14.0 (College Station, Tex.). The association of each clinical variable on survival was first evaluated with univariable analysis, followed by multivariable analysis, which included clinical variables that were significantly associated with survival in the univariable analysis. No multicollinearity of covariates was found, and the proportional hazards assumption was met in the final models.

Example 2: Identification of a Gene Signature Predictive of HCC Patient Response to TACE This example describes the identification of a gene signature (TACE Navigator gene signature) that is predictive of response versus non-response to TACE, as measured by overall survival, independent of other clinical variables.

Clinical Characteristics of the Patients

For the study described in this example, 247 patients from the previously described LCI cohort were assigned to one of three groups based on the therapy each patient received during the course of their treatment following surgical resection: patients who received TACE as part of their treatment (TACE, n=105); patients who received other forms of adjuvant therapy except for TACE (Other Therapy, n=52); and patients who received no additional therapy (No Therapy, n=90). Each therapy group had similar clinical characteristics, with the exception of overall survival, in which the Other Therapy group had significantly better overall survival compared to the TACE and No Therapy groups (FIG. 1 and Table 1). A validation cohort, consisting of 49 patients from Hong Kong who had undergone surgical resection with adjuvant TACE performed at the time of surgery, was obtained for this study. LCI test cohort and Hong Kong validation cohort patients who received TACE had similar clinical characteristics, with the exception of the Hong Kong cohort having more patients with the presence of microvascular invasion and higher tumor-node-metastasis (TNM) staging, indicating more patients with advanced disease. However, overall survival between these two cohorts was not statistically different (Table 2).

TABLE 1

Clinical characteristics of LCI Cohort treatment groups

| Variable | TACE† (N = 105) | Other Therapy‡ (N = 52) | No Therapy# (N = 90) | P Value* |
|---|---|---|---|---|
| Age-year | | | | 0.94 |
| Median | 50 | 50 | 50 | |
| Range | 27-73 | 25-70 | 21-77 | |
| Sex-no. (%) | | | | 0.047 |
| Female | 8 (7.6) | 11 (21.2) | 12 (1.3) | |
| Male | 97 (92.4) | 40 (76.9) | 75 (83.3) | |
| Missing data | 0 | 1 (1.9) | 3 (3.4) | |
| HBV-no. (%) | | | | 0.92 |
| Chronic carrier | 71 (67.6) | 37 (71.2) | 63 (70.0) | |
| Active virus | 28 (26.7) | 13 (25.0) | 22 (24.4) | |
| Negative/ Missing data | 6 (5.7) | 2 (3.8) | 5 (5.6) | |
| Cirrhosis-no. (%) | | | | 0.10 |
| No | 12 (11.4) | 6 (11.5) | 3 (3.3) | |
| Yes | 93 (88.6) | 45 (86.5) | 84 (93.4) | |
| Missing data | 0 | 1 (2.0) | 3 (3.3) | |
| Alanine aminotransferase-no. (%) | | | | 0.26 |
| Normal (≤50 U/L) | 56 (53.3) | 32 (61.5) | 56 (62.2) | |
| Elevated (>50 U/L) | 49 (46.7) | 19 (36.5) | 31 (34.4) | |
| Missing Data | 0 | 1 (2.0) | 3 (3.4) | |
| Alpha-fetoprotein-no. (%) | | | | 0.40 |
| Negative (≤20 ng/mL) | 27 (25.7) | 17 (32.7) | 29 (32.2) | |
| Positive (>20 ng/mL) | 77 (73.3) | 32 (61.5) | 57 (63.3) | |
| Missing Data | 1 (1.0) | 3 (3.8) | 4 (4.5) | |
| Tumor Size-no. (%) | | | | 0.26 |
| ≤3 cm | 30 (28.6) | 20 (38.5) | 24 (26.7) | |
| >3 cm | 75 (71.4) | 30 (57.7) | 63 (70.0) | |
| Missing data | 0 | 2 (3.8) | 3 (3.3) | |
| Microvascular Invasion-no. (%) | | | | 0.29 |
| No | 68 (64.8) | 35 (67.3) | 49 (54.4) | |
| Yes | 37 (35.2) | 16 (30.8) | 38 (42.2) | |
| Missing data | 0 | 1 (1.9) | 3 (3.4) | |
| Multinodular Tumor-no. (%) | | | | 0.29 |
| No | 84 (80.0) | 39 (75.0) | 67 (74.4) | |
| Yes | 21 (20.0) | 12 (23.1) | 20 (22.2) | |
| Missing data | 0 | 1 (1.9) | 3 (3.4) | |
| TNM Stage-no. (%) | | | | 0.57 |
| I | 44 (41.9) | 22 (42.3) | 30 (33.3) | |
| II + III | 56 (53.3) | 25 (48.1) | 49 (54.4) | |

TABLE 1-continued

Clinical characteristics of LCI Cohort treatment groups

| Variable | TACE† (N = 105) | Other Therapy‡ (N = 52) | No Therapy# (N = 90) | P Value* |
|---|---|---|---|---|
| Missing Data | 5 (4.8) | 5 (9.6) | 11 (12.2) | |
| Survival (mo) | | | | 0.0018 |
| Median | >67 | >67 | 54.8 | |
| Range | 2.5->67.3 | 3->67.4 | 1.8->67.1 | |

†Patients designated as "TACE" received TACE at any time during their treatment following surgical resection. "TACE" patients may have also received additional adjuvant therapy during their treatment.
‡Patients designated as "other therapy" did not receive TACE during their treatment. Following surgical resection, "other therapy" patients received chemotherapy, interferon alfa therapy, radiofrequency ablation, percutaneous ethanol injection, or traditional Chinese medicine, or a combination thereof.
Patients as "no therapy" received no additional therapy following surgical resection.
*A P value of less than 0.05 was considered to indicate statistical significance. P values were calculated with the use of chi-square tests, except for age, which was calculated with ordinary one-way ANOVA, and survival, which was calculated with the log-rank test.

TABLE 2

Clinical characteristics of LCI cohort TACE patients and Hong Kong cohort TACE patients

| Variable | LCI Cohort (TACE) (N = 105) | Hong Kong Cohort (N = 49) | P Value* |
|---|---|---|---|
| Age-year | | | 0.29 |
| Median | 50 | 54 | |
| Range | 27-73 | 24-74 | |
| Sex-no. (%) | | | 0.24 |
| Female | 97 (92.4) | 42 (85.7) | |
| Male | 8 (7.6) | 7 (14.3) | |
| HBV-no. (%) | | | 0.41 |
| Chronic carrier | 71 (67.6) | 34 (69.4) | |
| Active virus | 28 (26.7) | 9 (18.4) | |
| Negative/Missing data | 6 (5.7) | 6 (12.2) | |
| Alpha-fetoprotein-no. (%) | | | 0.70 |
| Negative (≤20 ng/mL) | 27 (25.7) | 14 (28.6) | |
| Positive (>20 ng/mL) | 77 (73.3) | 34 (69.4) | |
| Missing Data | 1 (1.0) | 1 (2.0) | |
| Tumor Size-no. (%) | | | 0.11 |
| ≤3 cm | 30 (28.6) | 8 (16.3) | |
| >3 cm | 75 (71.4) | 41 (83.7) | |
| Microvascular Invasion-no. (%) | | | 0.02 |
| No | 68 (64.8) | 22 (44.9) | |
| Yes | 37 (35.2) | 27 (55.1) | |
| TNM Stage-no. (%) | | | 0.01 |
| I | 44 (41.9) | 11 (22.4) | |
| II + III | 56 (53.3) | 38 (77.6) | |
| Missing Data | 5 (4.8) | 0 | |
| Survival (mo) | | | 0.34 |
| Median | >67 | 44.1 | |
| Range | 2.5->67.3 | 4.8->60 | |

*A P value of less than 0.05 was considered to indicate statistical significance. P values were calculated with the use of Fisher's exact tests, except for age, which was calculated with a 2-tailed Student's t-test, and survival, which was calculated with the log-rank test.

Association of Gene Expression with Clinical Outcome in TACE Patients

Figure 1A:
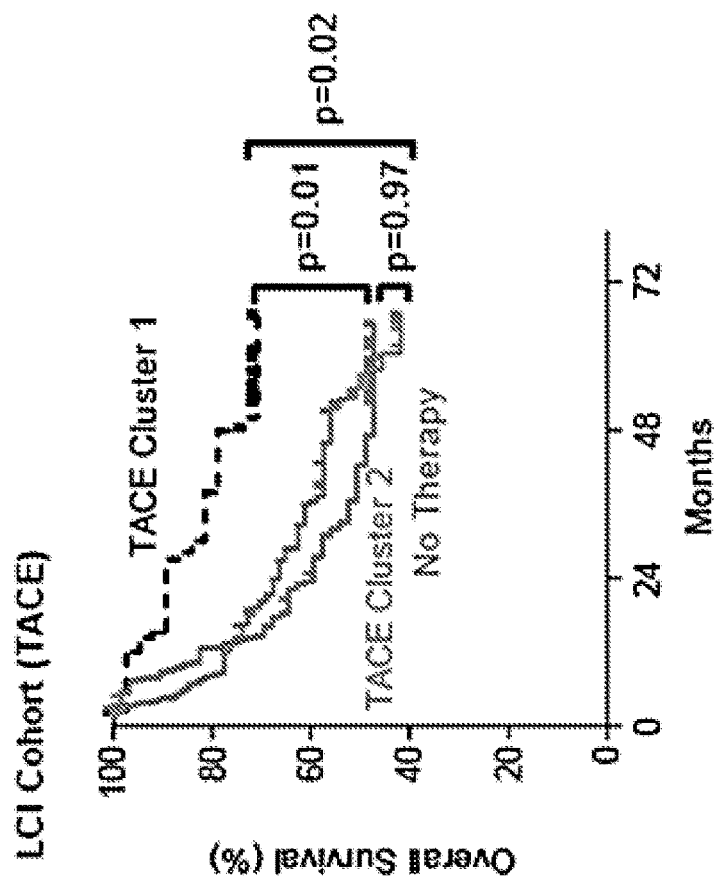

First, tumor gene expression data was examined from the LCI cohort, in which the expression of 13,101 genes had been previously measured by the AFFYMETRIX™ platform. Patients in the TACE group and Other Therapy group were subgrouped by hierarchical clustering using 1,292 "most variable genes". The 39 patients assigned to TACE cluster 1 had significantly longer overall survival compared to the 66 patients assigned to TACE cluster 2, but there was no statistically significant difference in overall survival between patients in TACE cluster 2 and the 90 patients receiving no therapy (FIG. 1A). However, when patients in the Other Therapy group were subjected to subgrouping by hierarchical clustering of the same most variable genes, there was no statistically significant difference in overall survival in the 28 patients assigned to Other Therapy cluster 1 and the 23 patients assigned to Other Therapy cluster 2 (FIG. 1B). These results indicated that differences in tumor gene expression may be associated with response vs. non-response to TACE, and may have utility in predicting which patients are most likely to respond to TACE treatment. Consistently, principal component analysis based on global expression patterns of all 13,101 genes revealed patients in TACE cluster 1 and TACE cluster 2 as two distinct molecular groups.

Figure 2A:
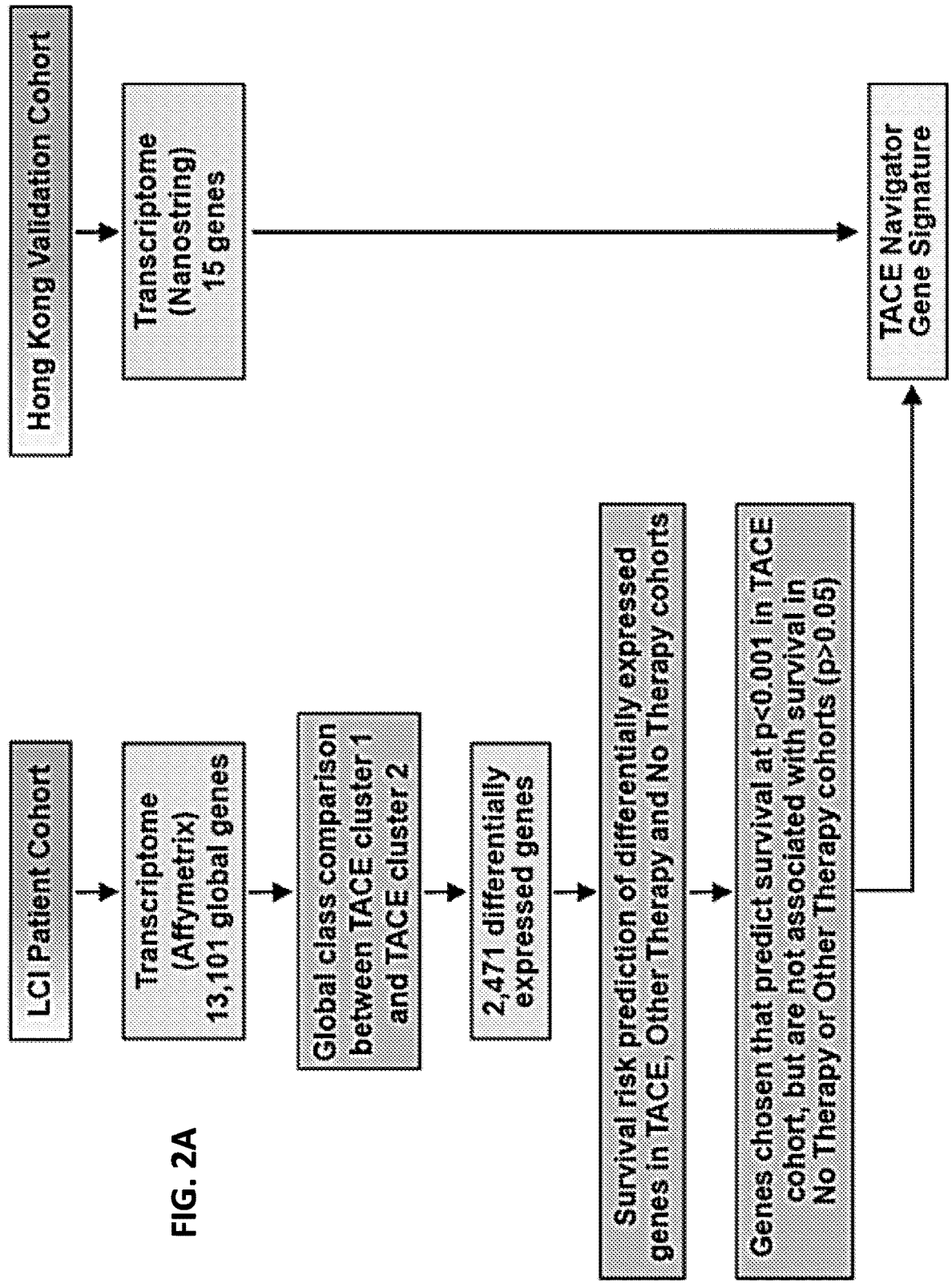
FIG. 2A is a schematic showing the process that was used to determine the genes that were included in the TACE Navigator gene signature.

Development of a Gene Signature Predictive of Overall Survival Following TACE Treatment To develop a gene signature that may be predictive of TACE response, a systematic approach was used (FIG. 2A). First, class comparison with global gene expression between TACE cluster 1 and TACE cluster 2 (FIG. 1A) was performed to find differentially expressed genes between the two groups. Of 13,101 global genes, 2,471 genes were found to have differential expression between TACE cluster 1 and TACE cluster 2. Then, survival risk prediction of the 2,471 differentially expressed genes in the TACE, Other Therapy and No Therapy cohorts was performed to determine which genes were statistically associated with survival in each cohort. Finally, in order to choose genes that would be most likely to be linked to TACE treatment, all genes that were associated with survival in the TACE cohort with a significance of p<0.001, but were not statistically associated with survival in the Other Therapy and No Therapy cohorts (p>0.05) (FIG. 2A), were selected. This process yielded 15 genes, which formed the basis of the gene signature (Table 3).

TABLE 3

15 TACE Navigator genes

| Gene Symbol | Description | Fold Change Responders vs. Non-Responders | Parametric p-value |
|---|---|---|---|
| ASNS | Asparagine synthetase | 0.33 | $<1 \times 10^{-7}$ |
| CDK1 | Cyclin-dependent kinase 1 | 0.54 | $3.4 \times 10^{-6}$ |
| DNASE1L3 | Deoxyribonuclease I-like 3 (DNase) | 2.91 | $<1 \times 10^{-7}$ |
| FBXL5 | F-box and leucine-rick repeat protein 5 | 1.52 | $1.8 \times 10^{-6}$ |
| GABARAPL3 | GABA(A) receptors associated protein like 3 | 1.41 | $8.5 \times 10^{-6}$ |
| GOT2 | Glutamic-oxaloacetic transaminase 2, mitochondrial | 1.92 | $1 \times 10^{-7}$ |
| GRHPR | Glyoxylate reductase/hydroxypyruvate reductase | 2.20 | $<1 \times 10^{-7}$ |
| IARS | Isoleucyl-tRNA synthetase | 0.64 | $4 \times 10^{-7}$ |
| LGALS3 | Lectin, galactoside-binding, soluble 3 | 0.35 | $<1 \times 10^{-7}$ |
| LHFPL2 | Lipoma HMGIC fusion partner-like 2 protein | 0.57 | $<1 \times 10^{-7}$ |
| MFGE8 | Milk fat globule-EGF factor 8 protein | 0.80 | $8.16 \times 10^{-5}$ |
| MKI67 | Antigen Ki-67 | 0.63 | $<1 \times 10^{-7}$ |
| PEBP1 | Phosphatidylethanolamine binding protein 1 | 1.74 | $<1 \times 10^{-7}$ |
| TNFSF10 | Tumor necrosis factor superfamily, member 10 (TRAIL) | 2.05 | $1.7 \times 10^{-6}$ |
| UBB | Ubiquitin B | 1.23 | $6.8 \times 10^{-6}$ |

Figure 2B:
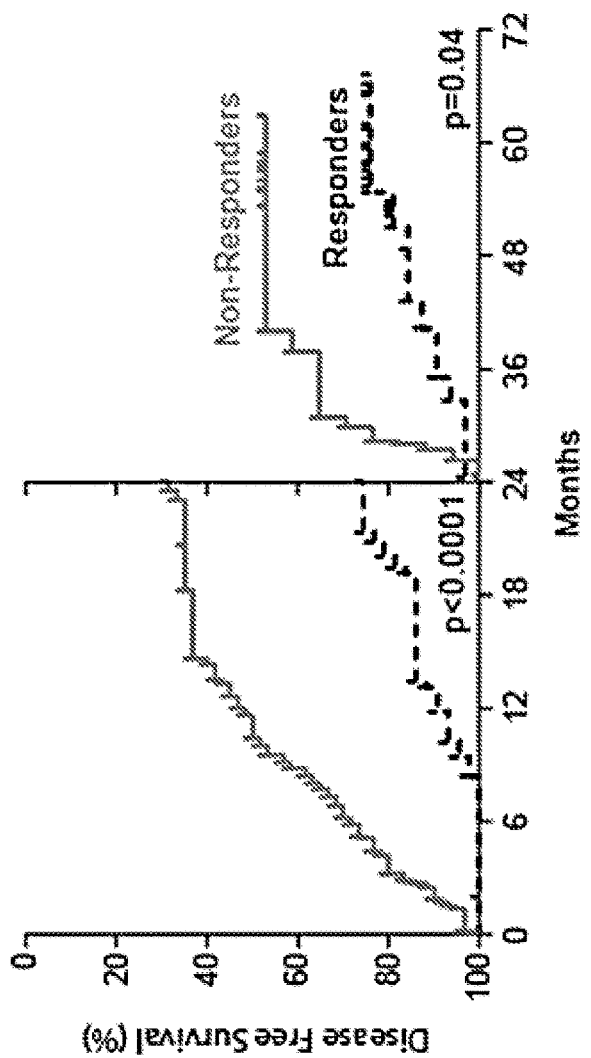
FIG. 2B is a pair of graphs demonstrating that the 45 TACE patients assigned to the "responder" cluster had significantly better overall survival and early (<24 months) or late (>24 months) disease-free survival compared to the 60 patients assigned to the "nonresponder" cluster. P values were calculated by log-rank test.
Figure 2B:
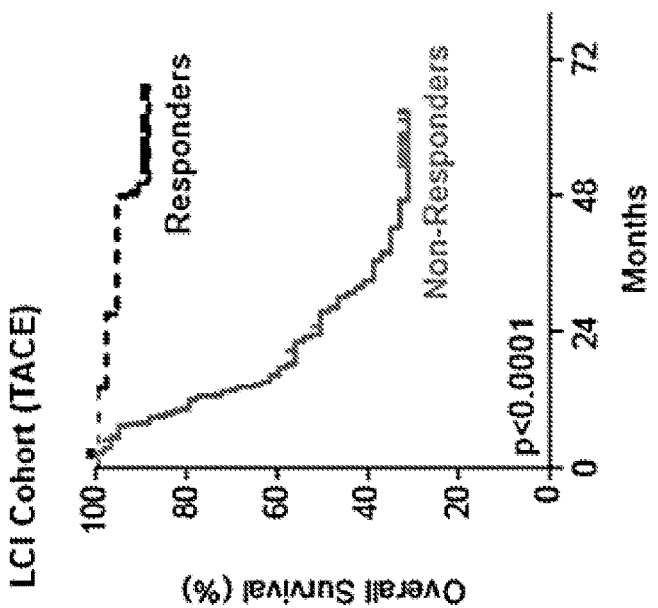
Figure 5:
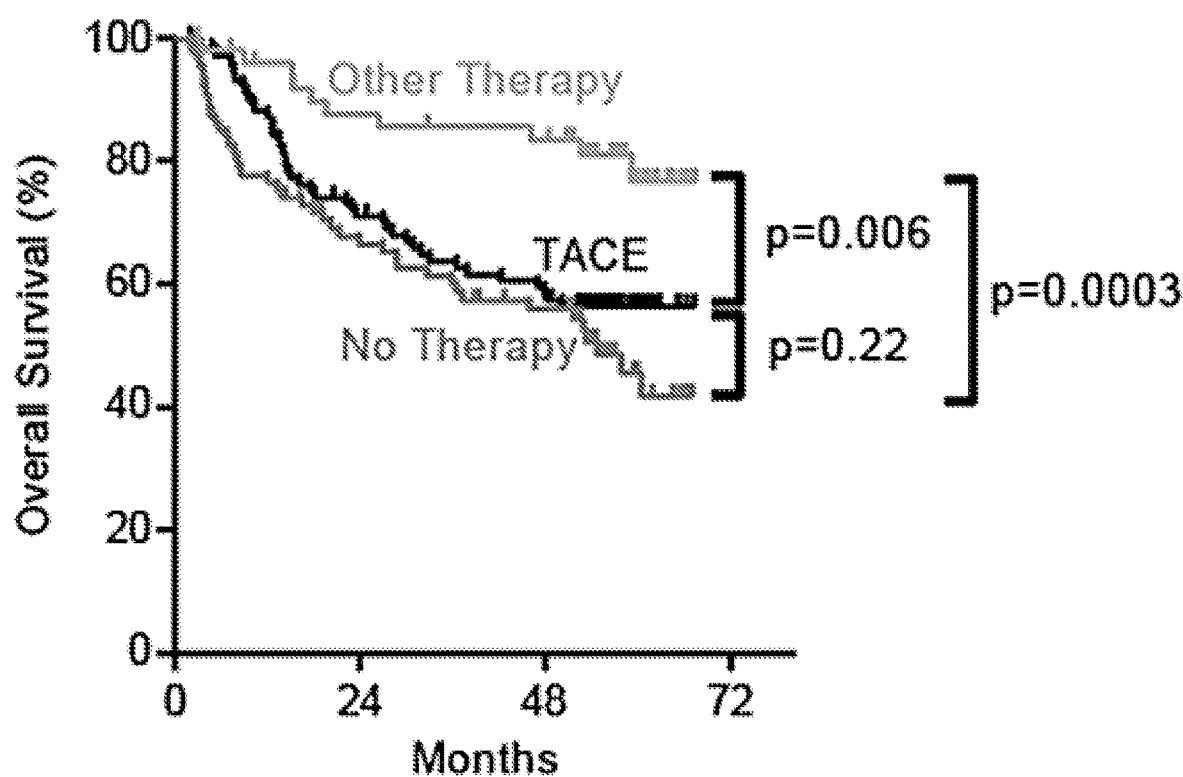
FIG. 5 is a graph showing Kaplan-Meier survival curves comparing overall survival for TACE, Other Therapy and No Therapy patient groups.
Figure 6:
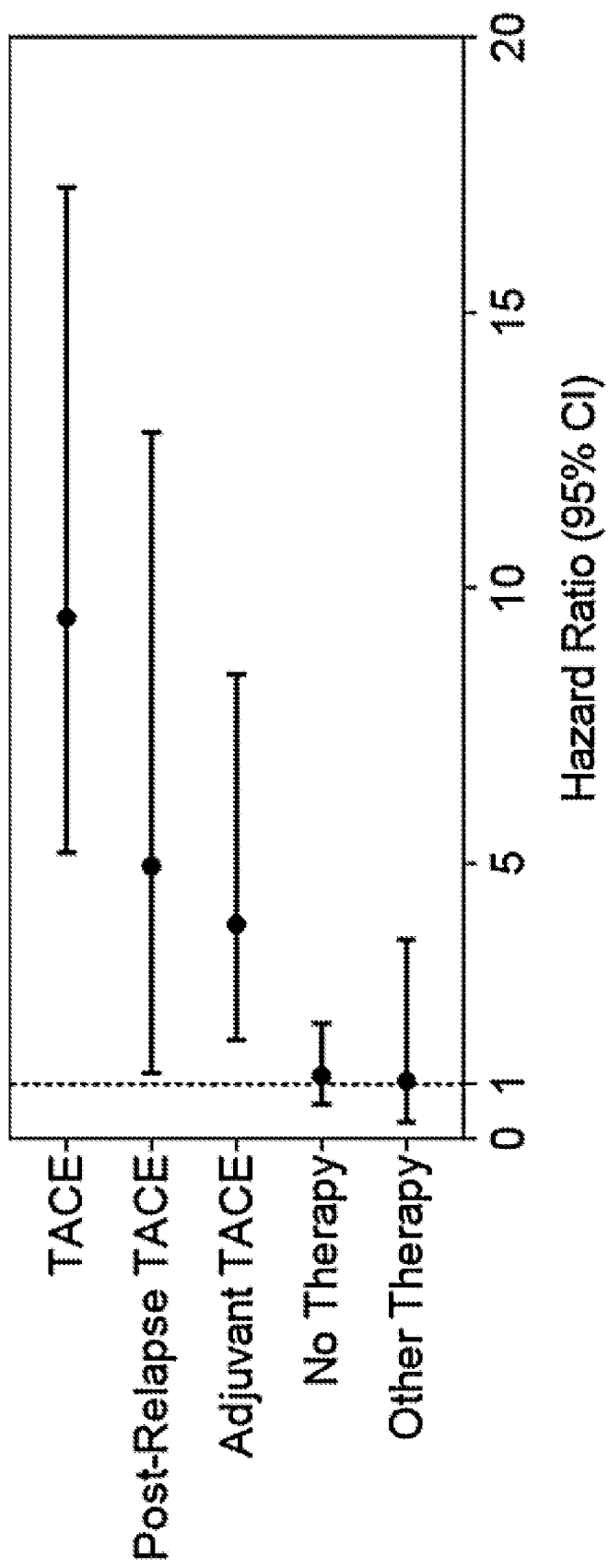
FIG. 6 is a Forest plot showing hazard ratios (dots) and 95% confidence intervals (whiskers) for each group of patients, following hierarchical clustering into two clusters by TACE Navigator gene signature.
Figure 7A:
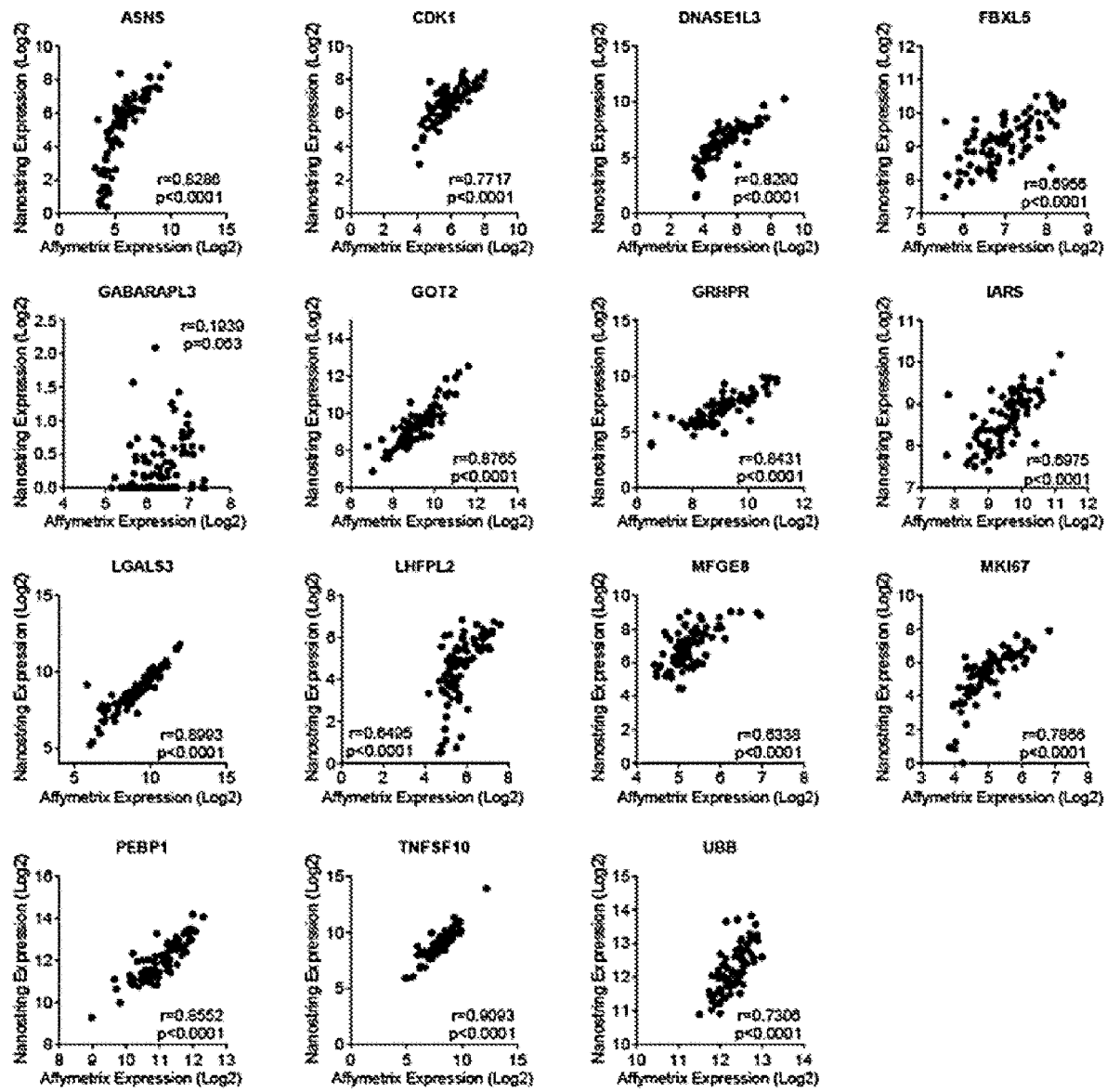

To examine the ability of the 15-gene signature to separate patients by outcome following treatment, as measured by overall survival, hierarchical clustering using these 15 genes in the TACE, Other Therapy and No Therapy cohorts was performed. In the TACE cohort, clustering revealed a subset of 45 patients, designated TACE Responders, and 60 patients, designated TACE Non-Responders, with a highly significant difference in overall survival (FIG. 2B). In addition, TACE Responders and Non-Responders exhibited a highly significant difference in early disease-free survival ($\leq 24$ months), as well as significantly different late disease-free survival ($\geq 24$ months). In addition, this 15-gene signature was predictive of survival when the TACE patient cohort was sub-divided into patients who received adjuvant TACE (n=75, p=0.0015) or received TACE post-relapse (n=30, p=0.0042). However, as expected, these 15 genes were not able to separate patients into clusters with different overall survival in the Other Therapy (p=0.67) or No Therapy (p=0.94) cohorts (FIG. 5).

To ensure that this 15-gene signature was able to predict outcome following TACE independent of other clinical variables, univariable analysis with Cox proportional-hazards regression was performed to determine the clinical variables that were significantly associated with survival in the TACE patient cohort. In addition to the assigned clinical group, cirrhosis status, tumor size, presence of microvascular invasion and TNM stage were each significantly associated with prognosis. The final multivariable model showed that only the clinical group as assigned by the TACE gene signature was independently associated with survival (Table 4). Thus, further analysis was carried out with this 15-gene signature, which was termed TACE Navigator.

TABLE 4

Hazard ratios for death among patients designated as TACE Responders or Non-Responders by the TACE Navigator Gene Signature, within the LCI cohort, according to univariable and multivariable analysis

| Variable | Hazard Ratio (95% CI) | P Value |
|---|---|---|
| Univariable Analysis | | |
| TACE Signature (Responder vs. Non-Responder) | 10.11 (3.95-25.86) | <0.001 |
| Age ($\leq 50$ yr vs. >50 yr) | 0.93 (0.50-1.71) | 0.813 |
| Sex (male vs. female) | 1.27 (0.40-4.14) | 0.680 |
| HBV (chronic carrier vs. active virus) | 1.54 (0.80-2.94) | 0.196 |
| Cirrhosis (no vs. yes) | 7.81 (1.07-56.82) | 0.042 |
| Alanine aminotransferase ($\leq 50$ U/L vs >50 U/L) | 0.87 (0.48-1.59) | 0.649 |
| Alpha-fetoprotein ($\leq 20$ ng/mL vs. >20 ng/mL) | 0.98 (0.50-1.89) | 0.931 |
| TNM Stage (I vs. II + III) | 2.98 (1.44-5.76) | 0.003 |
| Additional Therapy (no vs. yes) | 1.02 (0.56-1.86) | 0.948 |
| Multivariable Analysis | | |
| TACE Clinical Group | 10.02 (3.80-26.39) | <0.001 |
| Cirrhosis | 6.69 (0.89-50.25) | 0.065 |
| TNM Stage | 1.42 (0.69-2.91) | 0.344 |

Validation of TACE Navigator Gene Signature

Figure 3A:
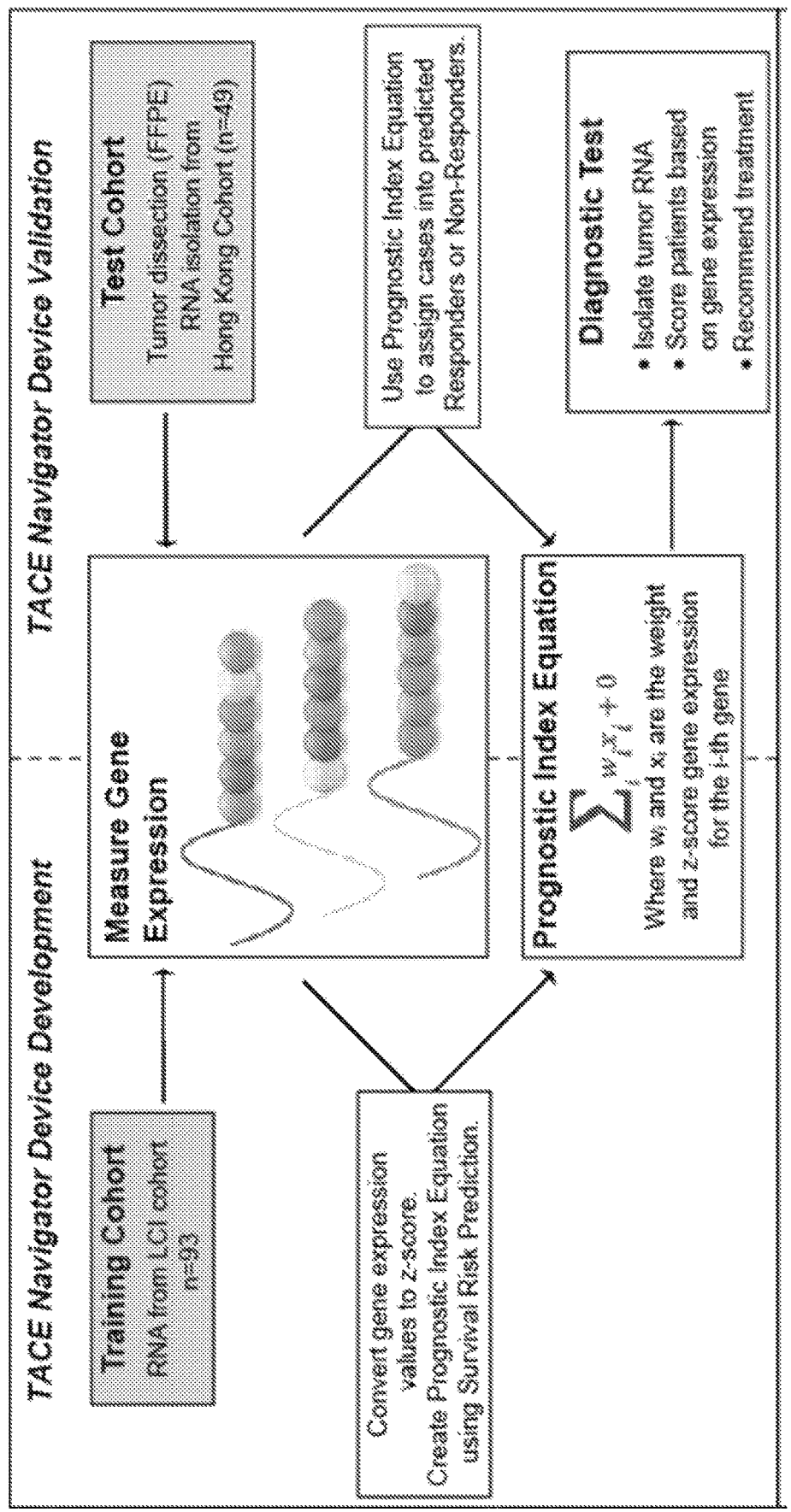
FIG. 3A is a schematic that depicts the procedure for developing and validating the TACE navigator diagnostic device, and shows how the device can be applied in a clinical setting.

In order to develop the TACE Navigator gene signature as a diagnostic device, a pipeline in which to test and validate the findings was created (FIG. 3A). Since the validation samples were from FFPE tumor tissue, which are known to have significant RNA degradation, the gene signature was validated using the NANOSTRING™ platform, which is optimized for use with heavily degraded samples. The creation of a custom NANOSTRING™ nCounter CodeSet, containing probes for each of the 15 genes of the signature, was commissioned. First, archived RNA for all available LCI TACE patients (n=93) was obtained, and gene expression was measured using the CodeSet, to ensure that gene expression as measured by AFFYMETRIX™ was correlated to gene expression as measured by NANOSTRING™. Indeed, expression was highly correlated for all genes except for GABARAPL3, which was subsequently dropped from the signature. Gene expression was then normalized by z-score, to correct for differences in gene expression measured in RNA from frozen tissue or FFPE tissue.

Figure 3B:
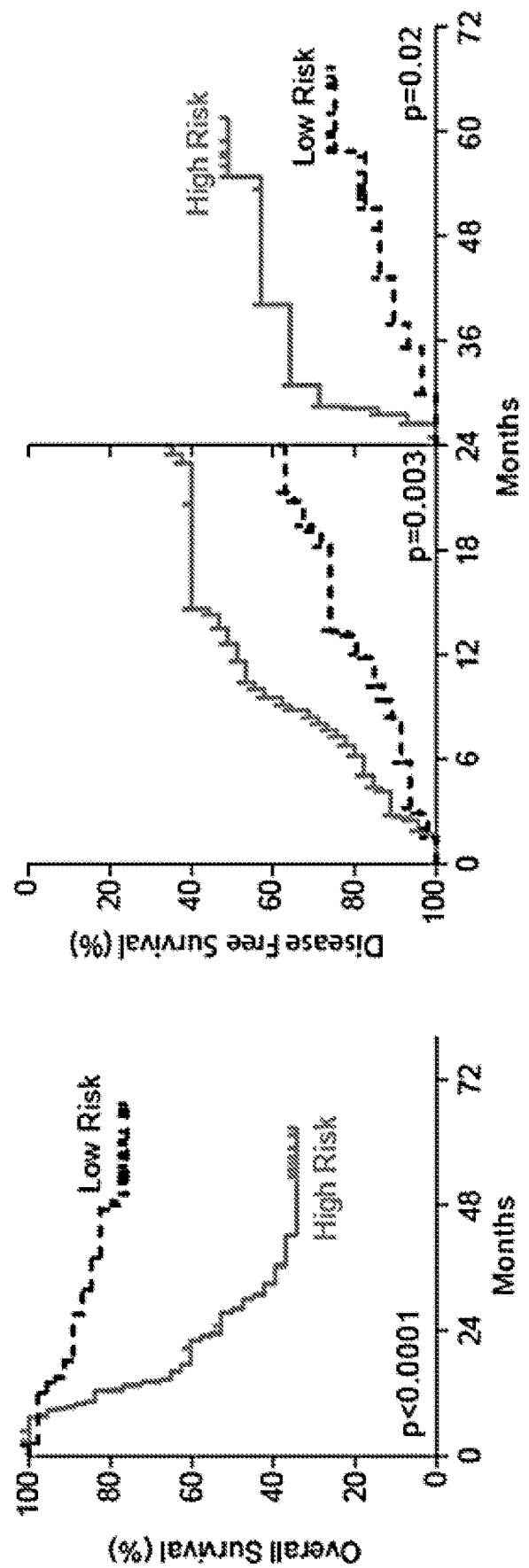
FIG. 3B is a pair of graphs demonstrating that the 47 TACE patients assigned as "low risk" experienced significantly better overall survival, as well as early (<24 months) or late (>24 months) disease-free survival, compared to the 46 TACE patients assigned as "high risk" by survival risk prediction using the TACE Navigator prognostic device.
Figure 3C:
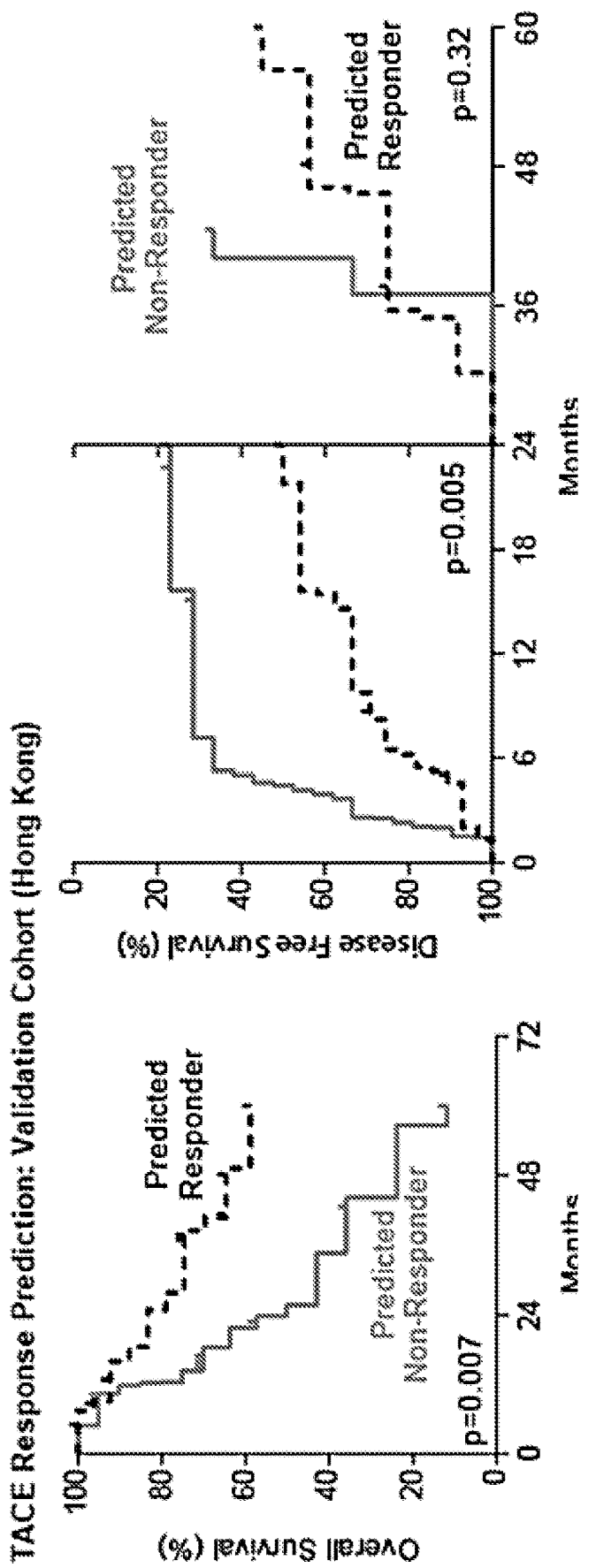
FIG. 3C is a pair of graphs demonstrating that when the device was used to predict TACE patient responders or non-responders in the Hong Kong validation cohort, the 28 patients predicted as "responders" experienced significantly better overall survival and early recurrence-free survival than the 21 patients predicted to be "non-responders." P values were calculated by log-rank test.

Using the LCI TACE patients as a test cohort, survival risk prediction using the 14 signature genes was performed to assign patients into low- and high-risk groups, demonstrating that the TACE Navigator device is able to predict overall survival and disease-free survival when gene expression is measured by NANOSTRING™ (FIG. 3B). In addition, survival risk prediction is used to create a Prognostic Index Equation and prognostic threshold (FIG. 3A), which can then be applied to new samples that are measured. After isolating RNA from coded FFPE tissue from the validation cohort, measuring gene expression using the CodeSet, and converting gene expression data to z-score, the gene expression data was input into the Prognostic Index Equation, and patients were assigned as predicted Responders or predicted Non-Responders, based on the threshold that was determined in the previous step. These samples were then decoded and were subjected to survival analysis. The 28 patients assigned to the predicted Responder group had significantly better overall survival and early disease-free survival compared to the 21 patients assigned to the predicted Non-Responder group (FIG. 3B). Univariable and multivariable analysis demonstrated that the TACE Navigator gene signature was able to predict overall survival in the Hong Kong cohort, independent of other clinical variables (Table 5).

TABLE 5

Hazard ratios for death among patients designated as TACE Responders or Non-Responders by the TACE Navigator Gene Signature, within the Hong Kong cohort, according to univariable and multivariable analysis

| Variable | Hazard Ratio (95% CI) | P Value |
|---|---|---|
| Univariable Analysis | | |
| TACE Signature (Responder vs. Non-Responder) | 3.16 (1.32-7.56) | 0.010 |

TABLE 5-continued

Hazard ratios for death among patients designated as TACE Responders or Non-Responders by the TACE Navigator Gene Signature, within the Hong Kong cohort, according to univariable and multivariable analysis

| Variable | Hazard Ratio (95% CI) | P Value |
|---|---|---|
| Age (≤50 yr vs. >50 yr) | 2.25 (0.86-5.91) | 0.100 |
| Sex (male vs. female) | 0.94 (0.28-3.20) | 0.922 |
| HBV (chronic carrier vs. active virus) | 0.84 (0.31-2.32) | 0.743 |
| Cirrhosis (no vs. yes) | 0.59 (0.26-1.36) | 0.215 |
| Alpha-fetoprotein (≤20 ng/mL vs. >20 ng/mL) | 1.25 (0.48-3.22) | 0.646 |
| TNM Stage (I vs. II + III) | 2.60 (1.39-8.62) | 0.128 |
| Multivariable Analysis | | |
| TACE Clinical Group | 3.21 (1.31-7.83) | 0.011 |
| Cirrhosis | 0.52 (0.23-1.23) | 0.138 |
| TNM Stage | 2.33 (0.67-8.05) | 0.181 |

Molecular Signaling Associated with TACE Response

Figure 4A:
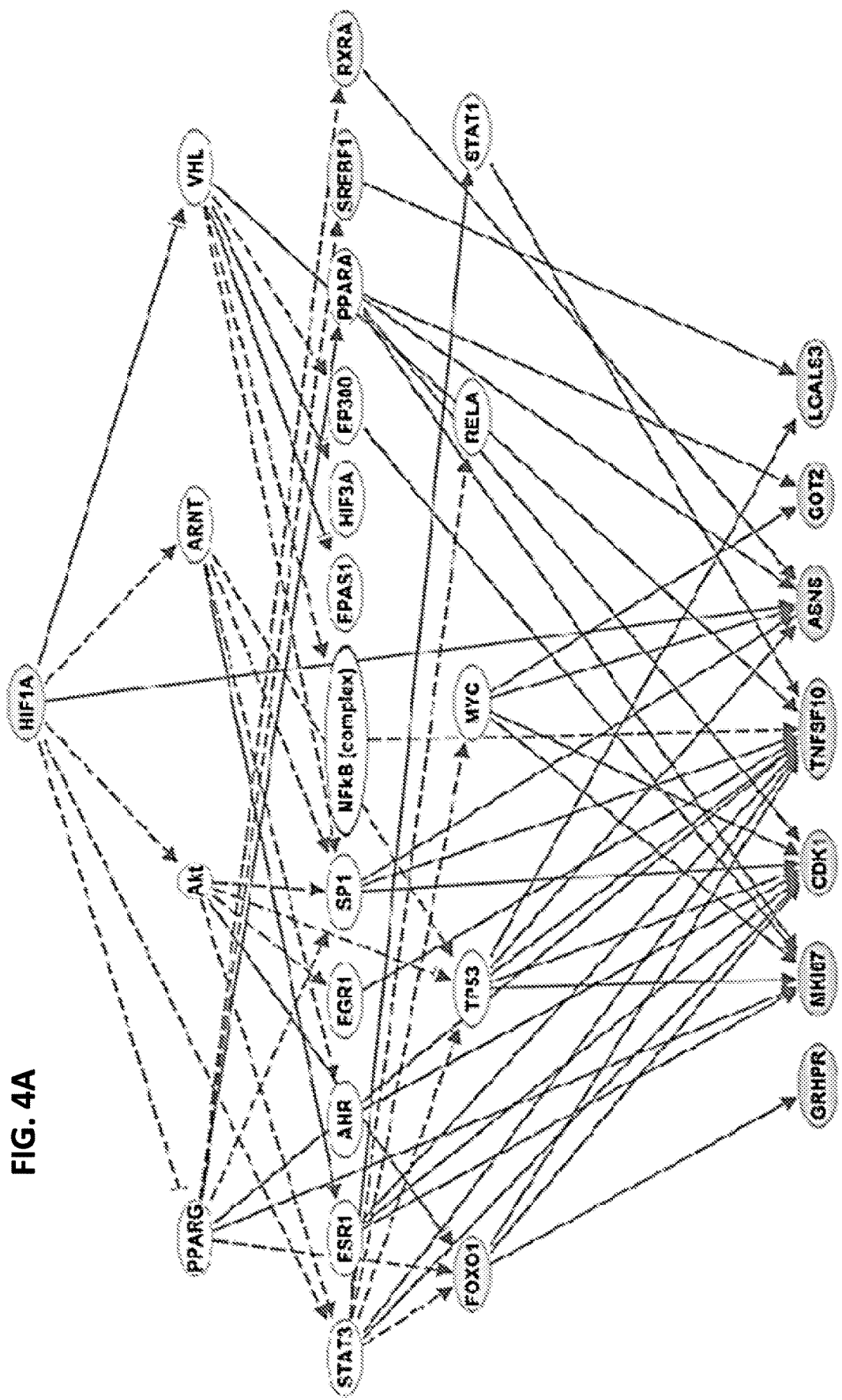
FIGS. 4A-4C show that the hypoxia response may be linked to TACE treatment resistance. When differentially expressed genes between TACE Responders and Non-Responders were analyzed by Ingenuity Pathway Analysis and Gene Set Enrichment Analysis, master hypoxia regulator HIF-1α was predicted to be directly upstream of seven TACE Navigator genes, as shown in FIG. 4A, and genes known to be up-regulated in response to hypoxia were enriched among differentially expressed genes, as shown in FIG. 4B. When examined directly, HIF-1α and target gene VEGF were up-regulated in TACE Non-Responders, compared to Responders (FIG. 4C). Box plots contain boxes extending from $25^{th}$ percentile to $75^{th}$ percentile, with the median value depicted by the line in the middle of the box, and Tukey whiskers (1.5 times Interquartile Range), with dots representing samples outside the Tukey variation. P values were calculated by Mann-Whitney U test.
Figure 4C:
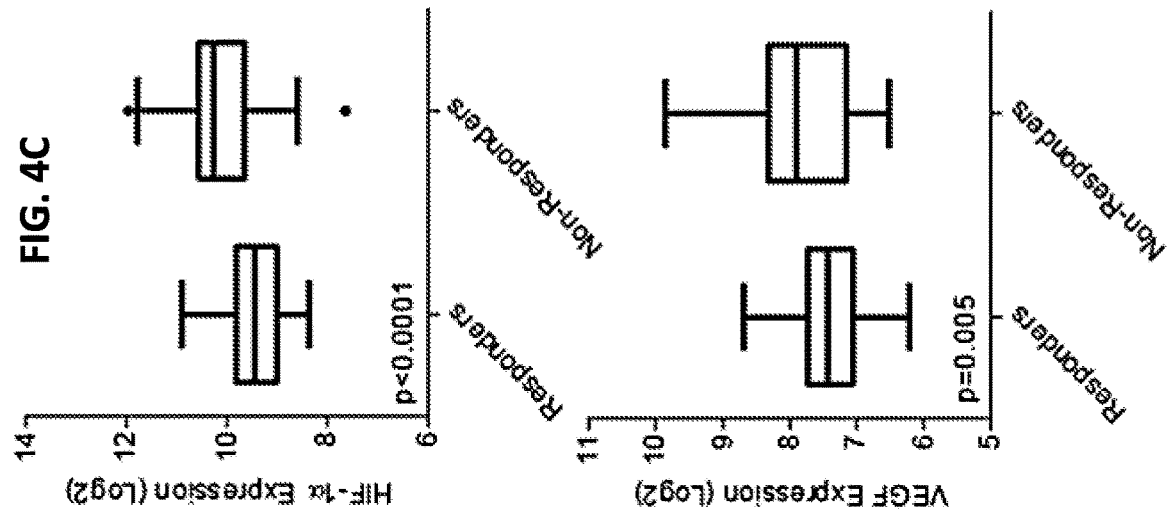
Figure 4B:
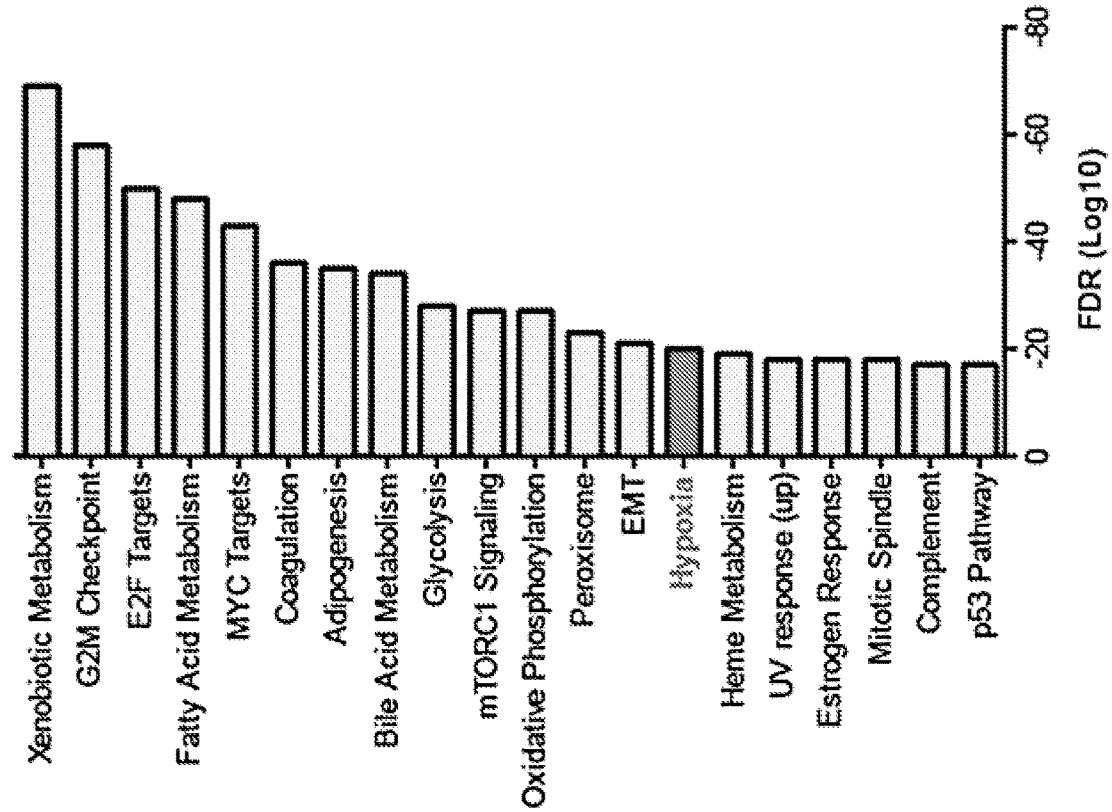

To examine potential mechanisms of TACE resistance in non-responder patients, the genes that were differentially expressed between TACE Responders and Non-Responders in the LCI cohort were examined, and these 1,726 differentially expressed genes were input into Ingenuity Pathway Analysis (IPA) and Gene Set Enrichment Analysis (GSEA). IPA analysis revealed that HIF-1α ranked as one of the top "upstream regulators" of genes that are differentially expressed between TACE Responders and Non-Responders (Table 6), and that 7 of the 15 TACE Navigator signature genes are downstream of HIF-1α signaling (FIG. 4A), suggesting a potential connection between hypoxia signaling and TACE response. Consistently, genes that are known to be upregulated in response to hypoxia were enriched in this gene set, as shown by GSEA (FIG. 4B). Indeed, when HIF-1α and hypoxia target gene VEGF were examined individually, both were significantly down-regulated in TACE Responders compared to Non-Responders, indicating that the tumor microenvironment in Non-Responders may already be hypoxic prior to TACE treatment, or may lead to an enhanced response to hypoxia induced during the TACE procedure.

TABLE 6

Results of Upstream Analysis by Ingenuity Pathway Analysis for differentially expressed genes between TACE Responders and Non-Responders

| Upstream Regulator[a] | Experiment Fold Change[b] | Molecule Type | Predicted Activation State[c] | Activation z-score[d] | P-value of Overlap[e] |
|---|---|---|---|---|---|
| TGFB1 | −1.266 | growth factor | Inhibited | −4.682 | 4.75E−45 |
| MYC | | transcription regulator | Inhibited | −6.552 | 2.83E−44 |
| ERBB2 | | kinase | Inhibited | −4.427 | 1.41E−38 |
| TNF | | cytokine | Inhibited | −4.292 | 1.82E−28 |
| MYCN | −1.19 | transcription regulator | Inhibited | −4.777 | 2.85E−27 |
| ESR1 | | ligand-dependent nuclear receptor | Inhibited | −2.367 | 6.12E−27 |
| E2F1 | | transcription regulator | Inhibited | −2.901 | 1.62E−22 |
| HGF | | growth factor | Inhibited | −3.82 | 7.29E−22 |
| VEGF | | group | Inhibited | −3.732 | 1.15E−21 |
| EGF | | growth factor | Inhibited | −4.46 | 4.77E−20 |
| RABL6 | | other | Inhibited | −5.209 | 1.65E−19 |
| IL1B | | cytokine | Inhibited | −3.866 | 7.25E−19 |
| HRAS | | enzyme | Inhibited | −2.783 | 3.23E−18 |
| OSM | | cytokine | Inhibited | −2.304 | 1.74E−17 |
| TBX2 | | transcription regulator | Inhibited | −4.386 | 2.74E−16 |
| AKT1 | | kinase | Inhibited | −2.727 | 3.35E−15 |
| PTGER2 | | g-protein coupled receptor | Inhibited | −4.36 | 5.24E−15 |

TABLE 6-continued

Results of Upstream Analysis by Ingenuity Pathway Analysis for differentially expressed genes between TACE Responders and Non-Responders

| Upstream Regulator[a] | Experiment Fold Change[b] | Molecule Type | Predicted Activation State[c] | Activation z-score[d] | P-value of Overlap[e] |
|---|---|---|---|---|---|
| INS | | other | Inhibited | −2.574 | 6.48E−14 |
| IL5 | | cytokine | Inhibited | −2.483 | 6.82E−14 |
| MAP4K4 | | kinase | Inhibited | −3.459 | 8.03E−14 |
| Cg | | complex | Inhibited | −2.455 | 9.60E−14 |
| E2F3 | −1.429 | transcription regulator | Inhibited | −2.794 | 1.08E−13 |
| E2f | | group | Inhibited | −4.019 | 2.15E−13 |
| FOXM1 | −1.562 | transcription regulator | Inhibited | −4.192 | 8.13E−13 |
| HIF1A | −1.667 | transcription regulator | Inhibited | −2.747 | 9.38E−13 |
| PDGF BB | | complex | Inhibited | −3.493 | 4.47E−12 |
| IGF2 | | growth factor | Inhibited | −2.433 | 1.59E−11 |
| ATF4 | −1.449 | transcription regulator | Inhibited | −2.766 | 1.98E−11 |
| NR0B2 | | ligand-dependent nuclear receptor | Inhibited | −2.737 | 2.01E−11 |
| CSF2 | | cytokine | Inhibited | −4.84 | 2.15E−11 |
| CCND1 | | transcription regulator | Inhibited | −4.354 | 1.62E−10 |
| NFYA | | transcription regulator | Inhibited | −2.198 | 5.49E−10 |
| KRAS | | enzyme | Inhibited | −2.268 | 5.71E−10 |
| EGFR | 1.18 | kinase | Inhibited | −3.858 | 6.26E−10 |
| MITF | | transcription regulator | Inhibited | −3.343 | 8.19E−10 |
| E2F2 | | transcription regulator | Inhibited | −2.828 | 8.70E−10 |
| F2 | 1.43 | peptidase | Inhibited | −2.571 | 2.85E−09 |
| ERK1/2 | | group | Inhibited | −3.315 | 3.76E−09 |
| PCK1 | 5.27 | kinase | Inhibited | −2.158 | 5.48E−09 |
| ERK | | group | Inhibited | −3.413 | 1.53E−08 |
| RAF1 | | kinase | Inhibited | −3.11 | 3.44E−08 |
| TAL1 | | transcription regulator | Inhibited | −2.077 | 3.86E−08 |
| IL2 | | cytokine | Inhibited | −2.583 | 4.62E−08 |
| AGT | | growth factor | Inhibited | −3.808 | 6.15E−08 |
| Akt | | group | Inhibited | −2.724 | 6.63E−08 |
| IGF1 | 1.61 | growth factor | Inhibited | −4.183 | 8.07E−08 |
| PI3K (family) | | group | Inhibited | −2.067 | 1.08E−07 |
| EP400 | −1.282 | other | Inhibited | −3.45 | 1.81E−07 |
| MAP2K1 | | kinase | Inhibited | −2.905 | 1.93E−07 |
| NRG1 | | growth factor | Inhibited | −3.746 | 3.50E−07 |
| PI3K (complex) | | complex | Inhibited | −3.122 | 4.75E−07 |
| SMOC2 | | other | Inhibited | −2.449 | 6.41E−07 |
| PLIN5 | | other | Inhibited | −2.728 | 9.98E−07 |
| PDGF (complex) | | complex | Inhibited | −2.601 | 1.22E−06 |
| NFκB (complex) | | complex | Inhibited | −2.275 | 1.81E−06 |
| ADORA2B | | g-protein coupled receptor | Inhibited | −2.164 | 3.46E−06 |
| TGFB3 | | growth factor | Inhibited | −2.822 | 4.10E−06 |
| Mek | | group | Inhibited | −3.137 | 5.95E−06 |
| EGR1 | | transcription regulator | Inhibited | −2.094 | 7.00E−06 |
| MAPK1 | | kinase | Inhibited | −2.509 | 7.26E−06 |
| Jnk | | group | Inhibited | −3.742 | 9.15E−06 |
| IL1A | | cytokine | Inhibited | −3.244 | 1.36E−05 |
| GAST | | other | Inhibited | −2.123 | 1.51E−05 |
| PDX1 | | transcription regulator | Inhibited | −2.483 | 1.96E−05 |
| EHHADH | 3.04 | enzyme | Inhibited | −2.63 | 2.60E−05 |
| NRIP1 | | transcription regulator | Inhibited | −2.309 | 4.57E−05 |
| FGF7 | | growth factor | Inhibited | −2.006 | 4.87E−05 |

[a]Genes shown in bold are directly regulated by HIF-1α, according to IPA
[b]Fold change of genes between TACE Responders and Non-Responders that appear in the list of differentially expressed genes between the two groups
[c]Only genes that were predicted to be inhibited in TACE Responders were examined
[d]Activation z-score was calculated by IPA, which infers the state of predicted regulators of transcription
[e]P-value of overlap, as calculated by Fisher's Exact Test by IPA, indicating a statistically significant overlap between differentially expressed genes and genes that are regulated by a candidate transcriptional regulator. Only genes with a p < 0.0001 were considered.

To further examine the possible connection of the hypoxia response to TACE resistance, survival risk prediction was performed using a list of 155 validated and predicted HIF-1a targets that form the core response to hypoxia, as determined by Benita et al. (*Nucleic Acids Res* 37:4587-4602, 2009). It was found that when these 155 genes were used to separate patients into high- and low-risk groups, a survival difference was seen only in patients who received TACE, but not in patients who received Other Therapy or No Therapy. Indeed, when class prediction algorithms were used to assign TACE patients into Responder or Non-Responder groups, all classification methods had p-values of less than 0.001. The Baysian Compound Covariate Predictor had the best classification performance, with 91% of patients classified correctly. These results indicate that there is a likely difference in the activation of HIF-1a signaling between the two groups.

Clinical Applications

HCC is a highly heterogeneous disease, with noted differences in angiogenesis; immune and cancer stem cell populations; and in the tumor microenvironment and extracellular milieu of individual tumors (Jeng et al., *Crit Rev Oncol Hematol* 94(3):337-347, 2015). The development of HCC is caused by a number of different etiologies including alcohol use and cirrhosis; chronic HBV or HCV infection; or nonalcoholic fatty liver disease and nonalcoholic steatohepatitis (Sanyal et al., *Oncologist* 15(Suppl 4):14-22, 2010), and these varying etiologies contribute to the high tumor heterogeneity observed in HCC.

Current recommendations for HCC treatment are driven by clinical practice guidelines, which differ across the globe. The Barcelona-Clinic Liver Cancer (BCLC) staging guidelines are commonly used in North America and Europe (*J Hepatol* 56:908-943, 2012), whereas in Asia, several other guideline systems are in place including the Chinese University Prognostic Index (CUPI score) (Leung et al., *Cancer* 94:1760-1769, 2002) and Japan Integrated Staging (JIS) (Kudo et al., *J Gastroenterol* 38:207-215, 2003). Although there are variations among the number of different scoring and guideline systems, all drive treatment decisions that are based mainly on tumor staging and liver function, with little focus on molecular tumor biology or individualized tumor features. JIS is an exception, which was recently updated to include three tumor biomarkers in its classification system (Kitai et al., *Oncology* 75(Suppl 1):83-90, 2008).

Orthotopic liver transplantation, local ablation or surgical resection are considered to be potentially curative HCC treatments, leading to a 70-75% 5-year survival rate for eligible patients (Raza and Sood, *World J Gastroenterol* 20:4115-4127, 2014). However, most HCC patients are considered to be ineligible for curative therapies, due to advanced tumor stage and liver function impairment, and instead rely on palliative treatments such as TACE (Villanueva et al., *Nat Rev Gastroenterol Hepatol* 10:34-42, 2013), yet these treatments often fail due to tumor recurrence (Lin et al., *Liver Cancer* 1:144-158, 2012). For patients with advanced HCC, multi-kinase inhibitor sorafenib is the only approved systemic therapy, however, only a modest survival benefit of <3 months has been demonstrated (Llovet et al., *N Engl J Med* 359:378-390, 2008). In the era of personalized medicine, in which predictive and prognostic biomarkers guide treatment modalities based on molecular tumor features, advances for HCC treatment have lagged behind other cancer types. Thus, new methods to determine the optimal treatment for HCC patients represent a great need.

To date, there are currently no gene signatures or biomarkers that are used to predict HCC patient response to TACE. To this end, the goal of the study disclosed herein was to create a clinically-relevant prognostic device, based on gene expression, that could classify HCC patients into two groups: those who were predicted to be more or less responsive to TACE. The studies disclosed herein led to the discovery and validation of a 14-gene signature, TACE Navigator, that independently predicted overall survival and early disease-free in two cohorts of HCC patients from Asia. The gene signature was not predictive of overall survival in patients who did not receive adjuvant therapy, or received other forms of adjuvant therapy, following surgical resection, indicating that the gene signature is specific to TACE treatment response, and not gross differences in tumor biology.

Examining differences in gene expression between TACE Responders and Non-Responders prior to treatment revealed that the hypoxia response may be a potential mechanism of resistance due to differences in HIF-1α signaling activation between TACE Responders and Non-Responders. TACE is known to induce changes in hypoxia master regulator HIF-1 and target gene VEGF, caused by occlusion of the hepatic artery during the procedure (Jia et al., Chin Med Sci J 26:158-162, 2011; Liu et al., *J Clin Med Res* 8:297-302, 2016). Several members of the gene signature were also connected directly to HIF-1α via downstream pathways, providing further evidence that the hypoxia response during the TACE procedure may play a role in TACE treatment resistance.

Example 3: TACE Navigator Gene Signature Assay

A custom and unique device can be engineered, which includes agents that permit detection of expression of the 15 signature genes (Table 3) and six housekeeping genes (chosen based on high gene expression, similar expression in tumor and non-tumor tissues, and a low amount of variation between tumor and non-tumor tissue in the LCI cohort). These housekeeping genes were also verified in an independent Asian cohort, the TIGER-LC cohort consisting of patients from Thailand (FIGS. SA and 8B).

In one example, the probes for the 14 or 15 signature genes and six housekeeping genes are from NanoString Technologies (e.g., NanoString nCounter® Analysis System). Thus, such probes can be used in the methods provided herein.

TABLE 7 nCounter® CodeSet Design

| Gene Name | Accession | Target Position | Target Sequence | SEQ ID NO: | Tm CP | Tm RP |
|---|---|---|---|---|---|---|
| ACTB | NM_001101.2 | 1011-1110 | TGCAGAAGGAGATCAC TGCCCTGGCACCCAGC ACAATGAAGATCAAGA TCATTGCTCCTCCTGAG CGCAAGTACTCCGTGT GGATCGGCGGCTCCAT CCT | 1 | 87 | 87 |
| ASNS | NM_183356.2 | 1645-1744 | GGGTTACATATATTTC ACAAGGCTCCTTCTCCT GAAAAAGCCGAGGAGG AGAGTGAGAGGCTTCT | 2 | 81 | 80 |

TABLE 7-continued

| | | nCounter® CodeSet Design | | | | |
|---|---|---|---|---|---|---|
| Gene Name | Accession | Target Position | Target Sequence | SEQ ID NO: | Tm CP | Tm RP |
| | | | GAGGGAACTCTATTTGT TTGATGTTCTCCGCGCA | | | |
| B2M | NM_004048.2 | 26-125 | CGGGCATTCCTGAAGC TGACAGCATTCGGGCC GAGATGTCTCGCTCCGT GGCCTTAGCTGTGCTCG CGCTACTCTCTCTTTCT GGCCTGGAGGCTATCC A | 3 | 82 | 81 |
| CDK1 | NM_001786.4 | 179-278 | GGTACCTATGGAGTTGT GTATAAGGGTAGACAC AAAACTACAGGTCAAG TGGTAGCCATGAAAAA AATCAGACTAGAAAGT GAAGAGGAAGGGGTTC CTA | 4 | 84 | 85 |
| DNASE1L3 | NM_001256560.1 | 479-578 | CCAGAGACATCCGTTA AGGAGATCGATGAGTT GGTTGAGGTCTACACG GACGTGAAACACCGCT GGAAGGCGGAGAATTT CATTTTCATGGGTGACT TCA | 5 | 83 | 80 |
| EEF1A1 | NM_001402.5 | 791-890 | ACAAGCCCTTGCGCCT GCCTCTCCAGGATGTCT ACAAAATTGGTGGTAT TGGTACTGTTCCTGTTG GCCGAGTGGAGACTGG TGTTCTCAAACCCGGTA T | 6 | 80 | 82 |
| FBXL5 | NM_001193534.1 | 1181-1280 | GCTTTGTCCTAACCTGG AGCATCTGGATCTTACC CAGACTGACATTTCAG ATTCTGCATTTGACAGT TGGTCTTGGCTTGGTTG CTGCCAGAGTCTTCGG | 7 | 82 | 78 |
| FTL | NM_000146.3 | 86-185 | CGCCCTCCGATTTCCTC TCCGCTTGCAACCTCCG GGACCATCTTCTCGGCC ATCTCCTGCTTCTGGGA CCTGCCAGCACCGTTTT TGTGGTTAGCTCCTT | 8 | 83 | 81 |
| GABARAPL3 | NR_028287.1 | 93-192 | TGCCCTCCCGCACACTT GGACCAGTGCTGTTGA CCCGGAAGCGGACATT TCTGCAGCTATTCTAAG CACACGTCGGCGGAGG GAGCGGGACGTGGCCA GC | 9 | 83 | 84 |
| GOT2 | NM_002080.2 | 2146-2245 | GGAGAGTAGGAAACTG TACTTTATCTCGGCATC CTCTTGAATGATAGTGC AAGTTTCTCCAGTTGGG ATGTTGTCTCTGCCCGG TTGGACCTCCTCCCTT | 10 | 81 | 81 |
| GRHPR | NM_012203.1 | 363-462 | ACAGATACCACCGCCG AACTCGCAGTCTCCCTG CTACTTACCACCTGCCG CCGGTTGCCGGAGGCC ATCGAGGAAGTGAAGA ATGGTGGCTGGACCTC GT | 11 | 83 | 84 |
| GUSB | NM_000181.1 | 1351-1450 | CGGTCGTGATGTGGTCT GTGGCCAACGAGCCTG CGTCCCACCTAGAATCT | 12 | 82 | 81 |

TABLE 7-continued nCounter® CodeSet Design

| Gene Name | Accession | Target Position | Target Sequence | SEQ ID NO: | Tm CP | Tm RP |
|---|---|---|---|---|---|---|
| | | | GCTGGCTACTACTTGAA GATGGTGATCGCTCAC ACCAAATCCTTGGACC C | | | |
| IARS | NM_002161.3 | 3953-4052 | ATGTTGTTCGGTCAGCC CTTCCCTAATTACACCT ATCCCCTACACATACAT GCACATAGACACACAC ATGAACACACTGAAGA TATTTCCTTCAGGTGTG | 13 | 79 | 82 |
| LDHA | NM_001165414.1 | 1691-1790 | AACTTCCTGGCTCCTTC ACTGAACATGCCTAGT CCAACATTTTTTCCCAG TGAGTCACATCCTGGG ATCCAGTGTATAAATCC AATATCATGTCTTGTGC | 14 | 78 | 79 |
| LGALS3 | NM_001177388.1 | 496-595 | CACGGTGAAGCCCAAT GCAAACAGAATTGCTT TAGATTTCCAAAGAGG GAATGATGTTGCCTTCC ACTTTAACCCACGCTTC AATGAGAACAACAGGA GA | 15 | 81 | 81 |
| LHFPL2 | NM_005779.2 | 629-728 | TGATTAACTCCGTGGAC TCCTGACTCTTTCTTCG CCCGGAACATCAATAT GTGTCATGTCATTGTCA CCTGTCGCTCGATGCTC TGGACCTTGCTGAGTA | 16 | 79 | 82 |
| MFGE8 | NM_001114614.1 | 329-428 | GCCACTGGGCCTGGAG AATGGGAACATTGCCA ACTCACAGATCGCCGC CTCGTCTGTGCGTGTGA CCTTCTTGGGTTTGCAG CATTGGGTCCCGGAGC TG | 17 | 83 | 84 |
| MKI67 | NM_002417.2 | 4021-4120 | AGCAGATGTAGAGGGA GAACTCTTAGCGTGCA GGAATCTAATGCCATC AGCAGGCAAAGCCATG CACACGCCTAAACCAT CAGTAGGTGAAGAGAA AGAC | 18 | 81 | 82 |
| PEBP1 | NM_002567.2 | 1336-1435 | CAGCGCTCGCTGACAG CTTGGGAGGAAACCTG AGATCTGTGTTTTTTAA ATTGATCGTTCTTCATG GGGGTAAGAAAAGCTG GTCTGGAGTTGCTGAAT G | 19 | 81 | 81 |
| TNFSF10 | NM_003810.2 | 116-215 | GGGGGGACCCAGCCTG GGACAGACCTGCGTGC TGATCGTGATCTTCACA GTGCTCCTGCAGTCTCT CTGTGTGGCTGTAACTT ACGTGTACTTTACCAAC | 20 | 82 | 79 |
| UBB | NM_018955.2 | 796-895 | CACCTGGTCCTGCGCCT GAGGGGTGGCTGTTAA TTCTTCAGTCATGGCAT TCGCAGTGCCCAGTGA TGGCATTACTCTGCACT ATAGCCATTTGCCCCAA | 21 | 86 | 85 |

TABLE 8 nCounter ® CodeSet Isoform Coverage

| Gene Name | Total Isoforms | Isoforms Hit by Probe | # Hit by Probe | Isoforms Not Hit by Probe |
|---|---|---|---|---|
| ACTB | 2 | NM_001101; XM_006715764 | 2 | |
| ASNS | 6 | NM_183356; NM_001673; NM_001178075; NM_001178077; NM_133436; NM_001178076 | 6 | |
| B2M | 3 | NM_004048; XM_006725182; XM_005254549 | 3 | |
| CDK1 | 6 | NM_001786; NM_001170407; XM_005270303; NM_033379; NM_001170406; XM_006718082 | 6 | |
| DNASE1L3 | 2 | NM_001256560; NM_004944 | 2 | |
| EEF1A1 | 2 | NM_001402; XM_011535514 | 2 | |
| FBXL5 | 8 | NM_001193534; NM_012161; XM_011513831; XM_011513832; XM_011513833; NM_001193535; XM_006713959; NR_036464 | 8 | |
| FTL | 1 | NM_000146 | 1 | |
| GABARAPL3 | 1 | NR_028287 | 1 | |
| GOT2 | 2 | NM_002080; NM_001286220 | 2 | |
| GRHPR | 4 | NM_012203; XM_011518073; XR_929374 | 3 | XM_005251631 |
| GUSB | 9 | NM_000181; XM_011516113; XM_011516114; XR_927461; XM_005250297; NM_001284290; NM_001293104; NM_001293105 | 8 | NR_120531 |
| IARS | 3 | NM_002161; NR_073446; NM_013417 | 3 | |
| LDHA | 6 | NM_001165414; NM_005566; NR_028500; NM_001165416; NM_001165415; NM_001135239 | 6 | |
| LGALS3 | 4 | NM_001177388; XM_011536759; NR_003225; NM_002306 | 4 | |
| LHFPL2 | 5 | NM_005779; XM_011543092; XR_948225; XM_006714515; XR_948226 | 5 | |
| MFGE8 | 4 | NM_001114614; XM_005254921; XR_931838; NM_005928 | 4 | |
| MKI67 | 4 | NM_002417; XM_011539818; XM_006717864; NM_001145966 | 4 | |
| PEBP1 | 1 | NM_002567 | 1 | |
| TNFSF10 | 4 | NM_003810; NM_001190943; NM_001190942; NR_033994 | 4 | |
| UBB | 6 | NM_018955; NM_001281716; NM_001281720; NM_001281717; NM_001281718; NM_001281719 | 6 | |

In view of the many possible embodiments to which the principles of the disclosure may be applied, it should be recognized that the illustrated embodiments are only examples of the invention and should not be taken as limiting the scope of the invention. Rather, the scope of invention is defined by the following claims. We therefore claim as our invention all that comes within the scope and spirit of these claims.

The invention claimed is:

1. A method of detecting expression of a plurality of genes, comprising:

detecting an increase in expression of asparagine synthetase (ASNS), cyclin-dependent kinase 1 (CDK1), F-box and leucine-rich repeat protein 5 (FBXL5), isoleucyl-tRNA synthetase (TARS), lectin, galactoside-binding, soluble 3 (LGALS3), lipoma HMGIC fusion partner-like 2 protein (LHFPL2), antigen Ki-67 (MKI67), and ubiquitin B (UBB) and a decrease in expression of deoxyribonuclease I-like 3 (DNASE1L3), glutamic-oxaloacetic transaminase 2, mitochondrial (GOT2), glyoxylate-reductase/hydroxy-pyruvate reductase (GRHPR), milk fat globule-EGF factor 8 protein (MFGE8), phosphatidylethanolamine binding protein 1 (PEBP1), and tumor necrosis factor superfamily, member 10 (TNFSF10), in a hepatocellular carcinoma (HCC) sample obtained from a subject diagnosed with HCC, relative to a control.

2. The method of claim 1, further comprising detecting a decrease in expression of GABA(A) receptors associated protein like 3, pseudogene (GABARAPL3) in an HCC sample obtained from a subject diagnosed with HCC, relative to a control.

3. The method of claim 1, further comprising detecting expression of 1 to 10 housekeeping genes or proteins.

4. The method of claim 1, wherein the subject diagnosed with HCC has a chronic viral infection or cirrhosis of the liver.

5. The method of claim 1, wherein detecting an increase or decrease in gene expression comprises detecting a level of ASNS, CDK1, DNASE1L3, FBXL5, GOT2, GRHPR, IARS, LGALS3, LHFPL2, MFGE8, MKI67, PEBP1, TNFSF10, and UBB mRNA using a microscope device.

6. The method of claim 5, further comprising detecting a level of GABARAPL3 mRNA using a microscope device.

7. The method of claim 1, further comprising converting gene expression values to a z-score and administering transarterial chemoembolization (TACE) to the subject.

8. The method of claim 7, further comprising applying a prognostic index equation to predict whether the HCC will respond to TACE.

9. A method of detecting expression of a plurality of genes, comprising:
  detecting an increase in expression of asparagine synthetase (ASNS), cyclin-dependent kinase 1 (CDK1), F-box and leucine-rich repeat protein 5 (FBXL5), isoleucyl-tRNA synthetase (TARS), lectin, galactoside-binding, soluble 3 (LGALS3), lipoma HMGIC fusion partner-like 2 protein (LHFPL2), antigen Ki-67 (MKI67), and ubiquitin B (UBB) and a decrease in expression of deoxyribonuclease I-like 3 (DNASE1L3), glutamic-oxaloacetic transaminase 2, mitochondrial (GOT2), glyoxylate-reductase/hydroxypyruvate reductase (GRHPR), milk fat globule-EGF factor 8 protein (MFGE8), phosphatidylethanolamine binding protein 1 (PEBP1), and tumor necrosis factor superfamily, member 10 (TNFSF10), in a hepatocellular carcinoma (HCC) sample obtained from a subject diagnosed with HCC, relative to a control using a probe set comprising a nucleic acid probe specific for each of ASNS, CDK1, DNASE1L3, FBXL5, GOT2, GRHPR, IARS, LGALS3, LHFPL2, MFGE8, MKI67, PEBP1, TNFSF10, and UBB.

10. The method of claim 9, further comprising detecting a decrease in expression of GABA(A) receptors associated protein like 3, pseudogene (GABARAPL3) in an HCC sample obtained from a subject diagnosed with HCC, relative to a control.

11. A method of treating a hepatocellular carcinoma (HCC) in a subject, comprising:
  determining that the HCC will respond to transarterial chemoembolization (TACE) by detecting an increase in expression of asparagine synthetase (ASNS), cyclin-dependent kinase 1 (CDK1), F-box and leucine-rich repeat protein 5 (FBXL5), isoleucyl-tRNA synthetase (TARS), lectin, galactoside-binding, soluble 3 (LGALS3), lipoma HMGIC fusion partner-like 2 protein (LHFPL2), antigen Ki-67 (MKI67), and ubiquitin B (UBB) and a decrease in expression of deoxyribonuclease I-like 3 (DNASE1L3), glutamic-oxaloacetic transaminase 2, mitochondrial (GOT2), glyoxylate-reductase/hydroxypyruvate reductase (GRHPR), milk fat globule-EGF factor 8 protein (MFGE8), phosphatidylethanolamine binding protein 1 (PEBP1), and tumor necrosis factor superfamily, member 10 (TNFSF10), relative to a control; and
  administering TACE to the subject.

12. The method of claim 11, further comprising detecting a decrease in expression of GABA(A) receptors associated protein like 3, pseudogene (GABARAPL3) relative to a control.

13. A method of treating hepatocellular carcinoma (HCC), comprising:
  measuring increased expression of asparagine synthetase (ASNS), cyclin-dependent kinase 1 (CDK1), F-box and leucine-rich repeat protein 5 (FBXL5), isoleucyl-tRNA synthetase (TARS), lectin, galactoside-binding, soluble 3 (LGALS3), lipoma HMGIC fusion partner-like 2 protein (LHFPL2), antigen Ki-67 (MKI67), and ubiquitin B (UBB) in an HCC sample from a subject relative to a control;
  measuring decreased expression of deoxyribonuclease I-like 3 (DNASE1L3), glutamic-oxaloacetic transaminase 2, mitochondrial (GOT2), glyoxylate-reductase/ hydroxypyruvate reductase (GRHPR), milk fat globule-EGF factor 8 protein (MFGE8), phosphatidylethanolamine binding protein 1 (PEBP1), and tumor necrosis factor superfamily, member 10 (TNFSF10) in an HCC sample from a subject relative to a control; and
  treating the subject with transarterial chemoembolization (TACE), thereby treating the HCC.

14. The method of claim 13, wherein the TACE comprises one or more of cisplatin, adriamycin, mitomycin, and doxorubicin.

15. The method of claim 13, further comprising measuring alphafetoprotein (AFP) in a blood sample from the subject.

16. The method of claim 1, further comprising detecting expression of 1 to 6 housekeeping genes or proteins.

17. The method of claim 9, wherein the subject diagnosed with HCC has a chronic viral infection or cirrhosis of the liver.

18. The method of claim 11, wherein the subject diagnosed with HCC has a chronic viral infection or cirrhosis of the liver.

19. The method of claim 13, wherein the subject diagnosed with HCC has a chronic viral infection or cirrhosis of the liver.

* * * * *

SEQUENCE LISTING

```
<160> NUMBER OF SEQ ID NOS: 21

<210> SEQ ID NO 1
<211> LENGTH: 100
<212> TYPE: DNA
<213> ORGANISM: Homo sapiens

<400> SEQUENCE: 1
tgcagaagga gatcactgcc ctggcaccca gcacaatgaa gatcaagatc attgctcctc     60
ctgagcgcaa gtactccgtg tggatcggcg gctccatcct                          100

<210> SEQ ID NO 2
<211> LENGTH: 100
<212> TYPE: DNA
<213> ORGANISM: Homo sapiens

<400> SEQUENCE: 2
gggttacata tattttcaca aggctccttc tcctgaaaaa gccgaggagg agagtgagag     60
gcttctgagg gaactctatt tgtttgatgt tctccgcgca                          100
```

```
<210> SEQ ID NO 3
<211> LENGTH: 100
<212> TYPE: DNA
<213> ORGANISM: Homo sapiens

<400> SEQUENCE: 3
cgggcattcc tgaagctgac agcattcggg ccgagatgtc tcgctccgtg gccttagctg      60
tgctcgcgct actctctctt tctggcctgg aggctatcca                          100

<210> SEQ ID NO 4
<211> LENGTH: 100
<212> TYPE: DNA
<213> ORGANISM: Homo sapiens

<400> SEQUENCE: 4
ggtacctatg gagttgtgta taagggtaga cacaaaacta caggtcaagt ggtagccatg      60
aaaaaaatca gactagaaag tgaagaggaa ggggttccta                          100

<210> SEQ ID NO 5
<211> LENGTH: 100
<212> TYPE: DNA
<213> ORGANISM: Homo sapiens

<400> SEQUENCE: 5
ccagagacat ccgttaagga gatcgatgag ttggttgagg tctacacgga cgtgaaacac      60
cgctggaagg cggagaattt cattttcatg ggtgacttca                          100

<210> SEQ ID NO 6
<211> LENGTH: 100
<212> TYPE: DNA
<213> ORGANISM: Homo sapiens

<400> SEQUENCE: 6
acaagccctt gcgcctgcct ctccaggatg tctacaaaat tggtggtatt ggtactgttc      60
ctgttggccg agtggagact ggtgttctca aacccggtat                          100

<210> SEQ ID NO 7
<211> LENGTH: 100
<212> TYPE: DNA
<213> ORGANISM: Homo sapiens

<400> SEQUENCE: 7
gctttgtcct aacctggagc atctggatct tacccagact gacatttcag attctgcatt      60
tgacagttgg tcttggcttg gttgctgcca gagtcttcgg                          100

<210> SEQ ID NO 8
<211> LENGTH: 100
<212> TYPE: DNA
<213> ORGANISM: Homo sapiens

<400> SEQUENCE: 8
cgccctccga tttcctctcc gcttgcaacc tccgggacca tcttctcggc catctcctgc      60
ttctgggacc tgccagcacc gtttttgtgg ttagctcctt                          100

<210> SEQ ID NO 9
<211> LENGTH: 100
<212> TYPE: DNA
<213> ORGANISM: Homo sapiens

<400> SEQUENCE: 9
```

```
tgccctcccg cacacttgga ccagtgctgt tgacccggaa gcggacattt ctgcagctat    60
tctaagcaca cgtcggcgga gggagcggga cgtggccagc                        100
```

<210> SEQ ID NO 10
<211> LENGTH: 100
<212> TYPE: DNA
<213> ORGANISM: Homo sapiens

<400> SEQUENCE: 10

```
ggagagtagg aaactgtact ttatctcggc atcctcttga atgatagtgc aagtttctcc    60
agttgggatg ttgtctctgc ccggttggac ctcctccctt                        100
```

<210> SEQ ID NO 11
<211> LENGTH: 100
<212> TYPE: DNA
<213> ORGANISM: Homo sapiens

<400> SEQUENCE: 11

```
acagatacca ccgccgaact cgcagtctcc ctgctactta ccacctgccg ccggttgccg    60
gaggccatcg aggaagtgaa gaatggtggc tggacctcgt                        100
```

<210> SEQ ID NO 12
<211> LENGTH: 100
<212> TYPE: DNA
<213> ORGANISM: Homo sapiens

<400> SEQUENCE: 12

```
cggtcgtgat gtggtctgtg gccaacgagc ctgcgtccca cctagaatct gctggctact    60
acttgaagat ggtgatcgct cacaccaaat ccttggaccc                        100
```

<210> SEQ ID NO 13
<211> LENGTH: 100
<212> TYPE: DNA
<213> ORGANISM: Homo sapiens

<400> SEQUENCE: 13

```
atgttgttcg gtcagccctt ccctaattac acctatcccc tacacataca tgcacataga    60
cacacacatg aacacactga agatatttcc ttcaggtgtg                        100
```

<210> SEQ ID NO 14
<211> LENGTH: 100
<212> TYPE: DNA
<213> ORGANISM: Homo sapiens

<400> SEQUENCE: 14

```
aacttcctgg ctccttcact gaacatgcct agtccaacat tttttcccag tgagtcacat    60
cctgggatcc agtgtataaa tccaatatca tgtcttgtgc                        100
```

<210> SEQ ID NO 15
<211> LENGTH: 100
<212> TYPE: DNA
<213> ORGANISM: Homo sapiens

<400> SEQUENCE: 15

```
cacggtgaag cccaatgcaa acagaattgc tttagatttc caaagaggga atgatgttgc    60
cttccacttt aacccacgct tcaatgagaa caacaggaga                        100
```

<210> SEQ ID NO 16
<211> LENGTH: 100

```
<212> TYPE: DNA
<213> ORGANISM: Homo sapiens

<400> SEQUENCE: 16
tgattaactc cgtggactcc tgactctttc ttcgcccgga acatcaatat gtgtcatgtc      60
attgtcacct gtcgctcgat gctctggacc ttgctgagta                          100

<210> SEQ ID NO 17
<211> LENGTH: 100
<212> TYPE: DNA
<213> ORGANISM: Homo sapiens

<400> SEQUENCE: 17
gccactgggc ctggagaatg ggaacattgc caactcacag atcgccgcct cgtctgtgcg      60
tgtgaccttc ttgggtttgc agcattgggt cccggagctg                          100

<210> SEQ ID NO 18
<211> LENGTH: 100
<212> TYPE: DNA
<213> ORGANISM: Homo sapiens

<400> SEQUENCE: 18
agcagatgta gagggagaac tcttagcgtg caggaatcta atgccatcag caggcaaagc      60
catgcacacg cctaaaccat cagtaggtga agagaaagac                          100

<210> SEQ ID NO 19
<211> LENGTH: 100
<212> TYPE: DNA
<213> ORGANISM: Homo sapiens

<400> SEQUENCE: 19
cagcgctcgc tgacagcttg ggaggaaacc tgagatctgt gttttttaaa ttgatcgttc      60
ttcatggggg taagaaaagc tggtctggag ttgctgaatg                          100

<210> SEQ ID NO 20
<211> LENGTH: 100
<212> TYPE: DNA
<213> ORGANISM: Homo sapiens

<400> SEQUENCE: 20 gggggggaccc agcctgggac agacctgcgt gctgatcgtg atcttcacag tgctcctgca     60
gtctctctgt gtggctgtaa cttacgtgta ctttaccaac                          100

<210> SEQ ID NO 21
<211> LENGTH: 100
<212> TYPE: DNA
<213> ORGANISM: Homo sapiens

<400> SEQUENCE: 21
cacctggtcc tgcgcctgag gggtggctgt taattcttca gtcatggcat tcgcagtgcc      60
cagtgatggc attactctgc actatagcca tttgccccaa                          100
```